(12) United States Patent
Baxter, III et al.

(10) Patent No.: US 7,832,612 B2
(45) Date of Patent: Nov. 16, 2010

(54) LOCKOUT ARRANGEMENT FOR A SURGICAL STAPLER

(75) Inventors: Chester O. Baxter, III, Loveland, OH (US); James J. Bedi, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 148 days.

(21) Appl. No.: 12/234,113

(22) Filed: Sep. 19, 2008

(65) Prior Publication Data

US 2010/0072251 A1 Mar. 25, 2010

(51) Int. Cl.
*A61B 17/68* (2006.01)
(52) U.S. Cl. .................. 227/175.2; 227/19; 227/175.1; 227/175.4; 227/180.1
(58) Field of Classification Search .............. 227/175.2, 227/19, 175.1, 175.4, 180.1
See application file for complete search history.

(56) References Cited

U.S. PATENT DOCUMENTS

| | | | |
|---|---|---|---|
| 3,490,675 A | 1/1970 | Green et at | |
| 3,499,591 A | 3/1970 | Green | |
| 3,643,851 A | 2/1972 | Green et al. | |
| 3,662,939 A | 5/1972 | Bryan | |
| 3,717,294 A | 2/1973 | Green | |
| 3,819,100 A | 6/1974 | Noiles et al. | |
| 4,296,881 A | 10/1981 | Lee | |
| 4,304,236 A | 12/1981 | Conta et al. | |
| 4,331,277 A | 5/1982 | Green | |
| 4,383,634 A | 5/1983 | Green | |
| 4,396,139 A | 8/1983 | Hall et al. | |
| 4,402,445 A | 9/1983 | Green | |
| 4,415,112 A | 11/1983 | Green | |
| 4,429,695 A | 2/1984 | Green | |
| 4,475,679 A | 10/1984 | Fleury, Jr. | |
| 4,489,875 A | 12/1984 | Crawford et al. | |
| 4,500,024 A | 2/1985 | DiGiovanni et al. | |
| 4,505,414 A | 3/1985 | Filipi | |
| 4,520,817 A | 6/1985 | Green | |
| 4,522,327 A | 6/1985 | Korthoff et al. | |
| 4,527,724 A | 7/1985 | Chow et al. | |
| 4,530,453 A | 7/1985 | Green | |

(Continued)

FOREIGN PATENT DOCUMENTS

CA 2458946 A1 3/2003

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner*—Brian D Nash

(57) ABSTRACT

A surgical stapling instrument including a latch for securing first and second jaw members together, a cutting member which can be advanced and/or retracted relative to first and second jaw members, and, in addition, a lock which can prevent, or at least inhibit, the cutting member from being moved, or at least advanced, relative to the first and second jaw members before the latch has been closed. In at least one embodiment, the latch can be configured to engage the lock as the latch is moved from a fully open position to a fully closed position and operably disengage the lock from the cutting member.

43 Claims, 31 Drawing Sheets

U.S. PATENT DOCUMENTS

| | | | |
|---|---|---|---|
| 4,566,620 A | 1/1986 | Green et al. | |
| 4,573,622 A | 3/1986 | Green et al. | |
| 4,580,712 A | 4/1986 | Green | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,629,107 A | 12/1986 | Fedotov et al. | |
| 4,633,874 A | 1/1987 | Chow et al. | |
| 4,664,305 A | 5/1987 | Blake, III et al. | |
| 4,671,445 A | 6/1987 | Barker et al. | |
| 4,715,520 A | 12/1987 | Roehr, Jr. et al. | |
| 4,728,020 A | 3/1988 | Green et al. | |
| 4,752,024 A | 6/1988 | Green et al. | |
| 4,754,909 A | 7/1988 | Barker et al. | |
| 4,767,044 A | 8/1988 | Green | |
| 4,805,823 A | 2/1989 | Rothfuss | |
| 4,809,695 A | 3/1989 | Gwathmey et al. | |
| 4,817,847 A | 4/1989 | Redtenbacher et al. | |
| 4,819,853 A | 4/1989 | Green | |
| 4,821,939 A | 4/1989 | Green | |
| 4,869,414 A | 9/1989 | Green et al. | |
| 4,869,415 A | 9/1989 | Fox | |
| 4,892,244 A | 1/1990 | Fox et al. | |
| 4,938,408 A * | 7/1990 | Bedi et al. | 227/8 |
| 4,941,623 A | 7/1990 | Pruitt | |
| 4,944,443 A | 7/1990 | Oddsen et al. | |
| 4,978,049 A | 12/1990 | Green | |
| 5,065,929 A | 11/1991 | Schulze et al. | |
| 5,129,570 A | 7/1992 | Schulze et al. | |
| 5,137,198 A * | 8/1992 | Nobis et al. | 227/175.3 |
| 5,173,133 A | 12/1992 | Morin et al. | |
| 5,219,111 A | 6/1993 | Bilotti et al. | |
| 5,221,036 A | 6/1993 | Takase | |
| 5,417,361 A | 5/1995 | Williamson, IV | |
| 5,445,304 A | 8/1995 | Plyley et al. | |
| 5,447,265 A | 9/1995 | Vidal et al. | |
| 5,480,089 A | 1/1996 | Blewett | |
| 5,484,451 A * | 1/1996 | Akopov et al. | 606/139 |
| 5,485,947 A | 1/1996 | Olson et al. | |
| 5,487,499 A | 1/1996 | Sorrentino et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,509,596 A | 4/1996 | Green et al. | |
| 5,529,235 A | 6/1996 | Boiarski et al. | |
| 5,535,934 A | 7/1996 | Boiarski et al. | |
| 5,535,935 A | 7/1996 | Vidal et al. | |
| 5,547,117 A | 8/1996 | Hamblin et al. | |
| 5,553,765 A | 9/1996 | Knodel et al. | |
| 5,560,530 A | 10/1996 | Bolanos et al. | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,564,615 A | 10/1996 | Bishop et al. | |
| 5,577,654 A | 11/1996 | Bishop | |
| 5,580,067 A | 12/1996 | Hamblin et al. | |
| 5,584,425 A | 12/1996 | Savage et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,597,107 A * | 1/1997 | Knodel et al. | 227/175.2 |
| 5,601,224 A | 2/1997 | Bishop et al. | |
| 5,605,272 A | 2/1997 | Witt et al. | |
| 5,605,273 A | 2/1997 | Hamblin et al. | |
| 5,607,094 A | 3/1997 | Clark et al. | |
| 5,628,446 A | 5/1997 | Geiste et al. | |
| 5,630,539 A | 5/1997 | Plyley et al. | |
| 5,630,540 A | 5/1997 | Blewett | |
| 5,632,432 A | 5/1997 | Schulze et al. | |
| 5,634,584 A | 6/1997 | Okorocha et al. | |
| 5,636,779 A | 6/1997 | Palmer | |
| 5,636,780 A | 6/1997 | Green et al. | |
| 5,639,008 A | 6/1997 | Gallagher et al. | |
| 5,645,209 A | 7/1997 | Green et al. | |
| 5,647,526 A | 7/1997 | Green et al. | |
| 5,651,491 A | 7/1997 | Heaton et al. | |
| 5,653,373 A | 8/1997 | Green et al. | |
| 5,653,374 A | 8/1997 | Young et al. | |
| 5,655,698 A | 8/1997 | Yoon | |
| 5,657,921 A | 8/1997 | Young et al. | |
| 5,662,258 A | 9/1997 | Knodel et al. | |
| 5,662,260 A | 9/1997 | Yoon | |
| 5,669,544 A | 9/1997 | Schulze et al. | |
| 5,673,840 A | 10/1997 | Schulze et al. | |
| 5,673,841 A * | 10/1997 | Schulze et al. | 227/175.1 |
| 5,673,842 A | 10/1997 | Bittner et al. | |
| 5,678,748 A | 10/1997 | Plyley et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,690,269 A | 11/1997 | Bolanos et al. | |
| 5,692,668 A | 12/1997 | Schulze et al. | |
| 5,697,543 A | 12/1997 | Burdorff | |
| 5,704,534 A | 1/1998 | Huitema et al. | |
| 5,706,997 A | 1/1998 | Green et al. | |
| 5,711,472 A | 1/1998 | Bryan | |
| 5,715,987 A | 2/1998 | Kelley et al. | |
| 5,715,988 A | 2/1998 | Palmer | |
| 5,718,359 A | 2/1998 | Palmer et al. | |
| 5,732,871 A | 3/1998 | Clark et al. | |
| 5,732,872 A | 3/1998 | Bolduc et al. | |
| 5,735,445 A | 4/1998 | Vidal et al. | |
| 5,743,456 A | 4/1998 | Jones et al. | |
| 5,752,644 A | 5/1998 | Bolanos et al. | |
| 5,758,814 A | 6/1998 | Gallagher et al. | |
| 5,762,255 A | 6/1998 | Chrisman et al. | |
| 5,762,256 A | 6/1998 | Mastri et al. | |
| 5,779,130 A | 7/1998 | Alesi et al. | |
| 5,779,131 A | 7/1998 | Knodel et al. | |
| 5,779,132 A | 7/1998 | Knodel et al. | |
| 5,782,397 A | 7/1998 | Koukline | |
| 5,785,232 A | 7/1998 | Vidal et al. | |
| 5,794,834 A | 8/1998 | Hamblin et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,820,009 A | 10/1998 | Melling et al. | |
| 5,826,776 A | 10/1998 | Schulze et al. | |
| 5,836,503 A | 11/1998 | Ehrenfels et al. | |
| 5,839,639 A | 11/1998 | Sauer et al. | |
| 5,855,311 A | 1/1999 | Hamblin et al. | |
| 5,865,361 A | 2/1999 | Milliman et al. | |
| 5,878,937 A | 3/1999 | Green et al. | |
| 5,878,938 A | 3/1999 | Bittner et al. | |
| 5,894,979 A | 4/1999 | Powell | |
| 5,901,895 A | 5/1999 | Heaton et al. | |
| 5,911,353 A | 6/1999 | Bolanos et al. | |
| 5,941,442 A | 8/1999 | Geiste et al. | |
| 5,954,259 A | 9/1999 | Viola et al. | |
| 5,988,479 A | 11/1999 | Palmer | |
| 6,010,054 A | 1/2000 | Johnson et al. | |
| 6,032,849 A | 3/2000 | Mastri et al. | |
| 6,050,472 A * | 4/2000 | Shibata | 227/175.2 |
| 6,079,606 A | 6/2000 | Milliman et al. | |
| 6,102,271 A | 8/2000 | Longo et al. | |
| 6,109,500 A | 8/2000 | Alli et al. | |
| 6,119,913 A | 9/2000 | Adams et al. | |
| 6,126,058 A | 10/2000 | Adams et al. | |
| 6,131,789 A | 10/2000 | Schulze et al. | |
| 6,155,473 A | 12/2000 | Tompkins et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |

| | | |
|---|---|---|
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,330,965 B1 | 12/2001 | Milliman et al. |
| 6,488,197 B1 | 12/2002 | Whitman |
| 6,491,201 B1 | 12/2002 | Whitman |
| 6,505,768 B2 | 1/2003 | Whitman |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,619,529 B2 | 9/2003 | Green et al. |
| 6,644,532 B2 | 11/2003 | Green et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,755,338 B2 | 6/2004 | Hahnen et al. |
| 6,773,438 B1 * | 8/2004 | Knodel et al. ............... 606/139 |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,830,174 B2 | 12/2004 | Hillstead et al. |
| 6,843,403 B2 | 1/2005 | Whitman |
| RE38,708 E | 3/2005 | Bolanos et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,080,769 B2 | 7/2006 | Vresh et al. |
| 7,083,075 B2 | 8/2006 | Swayze et al. |
| 7,097,089 B2 | 8/2006 | Marczyk |
| 7,114,642 B2 | 10/2006 | Whitman |
| 7,121,446 B2 | 10/2006 | Arad et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,210,609 B2 | 5/2007 | Leiboff et |
| 7,213,736 B2 | 5/2007 | Wales et al. |
| 7,225,964 B2 | 6/2007 | Mastri et al. |
| 7,246,734 B2 | 7/2007 | Shelton, IV |
| 7,258,262 B2 | 8/2007 | Mastri et al. |
| 7,278,563 B1 | 10/2007 | Green |
| 7,296,724 B2 | 11/2007 | Green et al. |
| 7,303,106 B2 | 12/2007 | Milliman et al. |
| 7,303,107 B2 | 12/2007 | Milliman et al. |
| 7,328,828 B2 | 2/2008 | Ortiz et al. |
| 7,328,829 B2 | 2/2008 | Arad et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,847 B2 | 12/2008 | Viola et al. |
| 7,481,347 B2 | 1/2009 | Roy |
| 7,494,039 B2 | 2/2009 | Racenet et al. |
| 7,506,790 B2 | 3/2009 | Shelton, IV |
| 7,510,107 B2 | 3/2009 | Timm et al. |
| 7,546,940 B2 | 6/2009 | Milliman et al. |
| 7,549,564 B2 | 6/2009 | Boudreaux |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,631,793 B2 | 12/2009 | Rethy et al. |
| 7,641,093 B2 | 1/2010 | Doll et al. |
| 7,658,311 B2 | 2/2010 | Boudreaux |
| 7,665,646 B2 | 2/2010 | Prommersberger |
| 7,669,747 B2 | 3/2010 | Weisenburgh, II et al. |
| 7,673,782 B2 | 3/2010 | Hess et al. |
| 7,731,072 B2 | 6/2010 | Timm et al. |
| 7,735,703 B2 | 6/2010 | Morgan et al. |
| 2002/0117534 A1 | 8/2002 | Green et al. |
| 2004/0094597 A1 | 5/2004 | Whitman et al. |
| 2004/0108357 A1 | 6/2004 | Milliman et al. |
| 2004/0164123 A1 | 8/2004 | Racenet et al. |
| 2004/0173659 A1 | 9/2004 | Green et al. |
| 2004/0222268 A1 | 11/2004 | Bilotti et al. |
| 2004/0232201 A1 | 11/2004 | Wenchell et al. |
| 2005/0103819 A1 | 5/2005 | Racenet et al. |
| 2005/0184121 A1 | 8/2005 | Heinrich |
| 2005/0189397 A1 | 9/2005 | Jankowski |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0025816 A1 * | 2/2006 | Shelton ............... 606/215 |
| 2006/0049229 A1 | 3/2006 | Milliman et al. |
| 2006/0060630 A1 | 3/2006 | Shelton, IV et al. |
| 2006/0180634 A1 | 8/2006 | Shelton, IV et al. |
| 2006/0226196 A1 | 10/2006 | Hueil et al. |
| 2006/0273135 A1 * | 12/2006 | Beetel ............... 227/175.1 |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0045379 A1 | 3/2007 | Shelton, IV |
| 2007/0073340 A1 | 3/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |

| | | |
|---|---|---|
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0246505 A1 | 10/2007 | Pace-Floridia et al. |
| 2007/0262116 A1 | 11/2007 | Hueil et al. |
| 2007/0278277 A1* | 12/2007 | Wixey et al. ............. 227/175.2 |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0237298 A1 | 10/2008 | Schall et al. |
| 2008/0251568 A1 | 10/2008 | Zemlok et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314955 A1 | 12/2008 | Boudreaux et al. |
| 2008/0314957 A1 | 12/2008 | Boudreaux |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0090763 A1 | 4/2009 | Zemlok et al. |
| 2009/0200355 A1 | 8/2009 | Baxter, III et al. |
| 2009/0206123 A1 | 8/2009 | Doll et al. |
| 2009/0206124 A1 | 8/2009 | Hall et al. |
| 2009/0206125 A1 | 8/2009 | Huitema et al. |
| 2009/0206126 A1 | 8/2009 | Huitema et al. |
| 2009/0206128 A1 | 8/2009 | Hueil et al. |
| 2009/0206129 A1 | 8/2009 | Doll et al. |
| 2009/0206130 A1 | 8/2009 | Hall et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206134 A1 | 8/2009 | Swayze et al. |
| 2009/0206135 A1 | 8/2009 | Hall et al. |
| 2009/0206136 A1 | 8/2009 | Moore et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0206144 A1 | 8/2009 | Doll et al. |
| 2009/0209946 A1 | 8/2009 | Swayze et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255978 A1 | 10/2009 | Viola et al. |
| 2009/0289096 A1 | 11/2009 | Shelton, IV et al. |
| 2010/0023024 A1* | 1/2010 | Zeiner et al. ................. 606/144 |
| 2010/0032470 A1 | 2/2010 | Hess et al. |
| 2010/0065605 A1 | 3/2010 | Shelton, IV et al. |
| 2010/0065609 A1 | 3/2010 | Schwemberger |
| 2010/0069942 A1 | 3/2010 | Shelton, IV |
| 2010/0072252 A1 | 3/2010 | Baxter, III et al. |
| 2010/0072253 A1 | 3/2010 | Baxter, III et al. |
| 2010/0072256 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0096435 A1 | 4/2010 | Fuchs et al. |
| 2010/0133317 A1 | 6/2010 | Shelton, IV et al. |
| 2010/0133318 A1 | 6/2010 | Boudreaux |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 1775926 A | 1/1972 |
| DE | 9412228 U | 9/1994 |
| DE | 19924311 A1 | 11/2000 |

| | | | | | | |
|---|---|---|---|---|---|---|
| DE | 69328576 T2 | 1/2001 | | EP | 1652481 A2 | 5/2006 |
| DE | 20112837 U1 | 10/2001 | | EP | 1382303 B1 | 6/2006 |
| DE | 20121753 U1 | 4/2003 | | EP | 1045672 B1 | 8/2006 |
| DE | 10314072 A1 | 10/2004 | | EP | 1617768 B1 | 8/2006 |
| EP | 0122046 A1 | 10/1984 | | EP | 1702567 A2 | 9/2006 |
| EP | 0070230 B1 | 10/1985 | | EP | 1129665 B1 | 11/2006 |
| EP | 0033548 B1 | 5/1986 | | EP | 1256317 B1 | 12/2006 |
| EP | 0276104 A2 | 7/1988 | | EP | 1728473 A1 | 12/2006 |
| EP | 0639349 A2 | 2/1994 | | EP | 1728475 A2 | 12/2006 |
| EP | 0324636 B1 | 3/1994 | | EP | 1479346 B1 | 1/2007 |
| EP | 0593920 A1 | 4/1994 | | EP | 1484024 B1 | 1/2007 |
| EP | 0600182 A2 | 6/1994 | | EP | 1754445 A2 | 2/2007 |
| EP | 0630612 A1 | 12/1994 | | EP | 1759812 A1 | 3/2007 |
| EP | 0634144 A1 | 1/1995 | | EP | 1769756 A1 | 4/2007 |
| EP | 0646356 A2 | 4/1995 | | EP | 1769758 A1 | 4/2007 |
| EP | 0646357 A1 | 4/1995 | | EP | 1785097 A1 | 5/2007 |
| EP | 0653189 A2 | 5/1995 | | EP | 1790293 A2 | 5/2007 |
| EP | 0669104 A1 | 8/1995 | | EP | 1800610 A1 | 6/2007 |
| EP | 0511470 B1 | 10/1995 | | EP | 1300117 B1 | 8/2007 |
| EP | 0679367 A2 | 11/1995 | | EP | 1813199 A1 | 8/2007 |
| EP | 0392547 B1 | 12/1995 | | EP | 1813201 A1 | 8/2007 |
| EP | 0685204 A1 | 12/1995 | | EP | 1813203 A2 | 8/2007 |
| EP | 0699418 A1 | 3/1996 | | EP | 1813207 A1 | 8/2007 |
| EP | 0702937 A1 | 3/1996 | | EP | 1813209 A1 | 8/2007 |
| EP | 0705571 A1 | 4/1996 | | EP | 1839596 A1 | 10/2007 |
| EP | 0484677 B2 | 6/1996 | | EP | 1402821 B1 | 12/2007 |
| EP | 0541987 B1 | 7/1996 | | EP | 1872727 A1 | 1/2008 |
| EP | 0667119 B1 | 7/1996 | | EP | 1897502 A1 | 3/2008 |
| EP | 0770355 A1 | 5/1997 | | EP | 1702568 B1 | 7/2008 |
| EP | 0503662 B1 | 6/1997 | | EP | 1970014 A1 | 9/2008 |
| EP | 0578425 B1 | 9/1997 | | EP | 1980213 A2 | 10/2008 |
| EP | 0625335 B1 | 11/1997 | | EP | 1759645 B1 | 11/2008 |
| EP | 0552423 B1 | 1/1998 | | EP | 1693008 B1 | 12/2008 |
| EP | 0592244 B1 | 1/1998 | | EP | 2000102 A2 | 12/2008 |
| EP | 0648476 B1 | 1/1998 | | EP | 1749486 B1 | 3/2009 |
| EP | 0676173 B1 | 9/1998 | | EP | 2090256 A2 | 8/2009 |
| EP | 0603472 B1 | 11/1998 | | EP | 1813206 B1 | 4/2010 |
| EP | 0605351 B1 | 11/1998 | | FR | 999646 A | 2/1954 |
| EP | 0878169 A1 | 11/1998 | | FR | 1112936 A | 3/1956 |
| EP | 0879742 A1 | 11/1998 | | FR | 2765794 A | 1/1999 |
| EP | 0760230 B1 | 2/1999 | | GB | 939929 A | 10/1963 |
| EP | 0537572 B1 | 6/1999 | | GB | 1210522 A | 10/1970 |
| EP | 0552050 | 5/2000 | | GB | 2336214 A | 10/1999 |
| EP | 1090592 A1 | 4/2001 | | JP | 6007357 A | 1/1994 |
| EP | 1256318 B1 | 5/2001 | | JP | 7051273 A | 2/1995 |
| EP | 0908152 B1 | 1/2002 | | JP | 8033641 A | 2/1996 |
| EP | 0872213 B1 | 5/2002 | | JP | 8229050 A | 9/1996 |
| EP | 1238634 A2 | 9/2002 | | JP | 2000287987 A | 10/2000 |
| EP | 0656188 B1 | 1/2003 | | JP | 2001286477 A | 10/2001 |
| EP | 0829235 B1 | 6/2003 | | JP | 2002369820 A | 12/2002 |
| EP | 0813843 B1 | 10/2003 | | JP | 2005505322 T | 2/2005 |
| EP | 0741996 B1 | 2/2004 | | JP | 2005103293 A | 4/2005 |
| EP | 0705570 B1 | 4/2004 | | RU | 2187249 C2 | 8/2002 |
| EP | 1086713 B1 | 5/2004 | | RU | 2225170 C2 | 3/2004 |
| EP | 1426012 A1 | 6/2004 | | SU | 1377053 A1 | 2/1988 |
| EP | 0888749 B1 | 9/2004 | | SU | 1561964 A1 | 5/1990 |
| EP | 1477119 A1 | 11/2004 | | SU | 1722476 A1 | 3/1992 |
| EP | 1479345 A1 | 11/2004 | | WO | WO 93/08755 A1 | 5/1993 |
| EP | 1479347 A1 | 11/2004 | | WO | WO 95/18572 A1 | 7/1995 |
| EP | 1479348 A1 | 11/2004 | | WO | WO 95/23557 A1 | 9/1995 |
| EP | 1520521 A1 | 4/2005 | | WO | WO 95/29639 A1 | 11/1995 |
| EP | 1520523 A1 | 4/2005 | | WO | WO 96/22055 A1 | 7/1996 |
| EP | 1520525 A1 | 4/2005 | | WO | WO 96/35464 A1 | 11/1996 |
| EP | 1522264 A1 | 4/2005 | | WO | WO 97/34533 A1 | 9/1997 |
| EP | 1550408 A1 | 7/2005 | | WO | WO 97/39688 A2 | 10/1997 |
| EP | 1557129 A1 | 7/2005 | | WO | WO 98/17180 A1 | 4/1998 |
| EP | 1064883 B1 | 8/2005 | | WO | WO 98/30153 A1 | 7/1998 |
| EP | 1157666 B1 | 9/2005 | | WO | WO 99/12483 A1 | 3/1999 |
| EP | 1621138 A2 | 2/2006 | | WO | WO 99/15086 A1 | 4/1999 |
| EP | 1621139 A2 | 2/2006 | | WO | WO 99/34744 A1 | 7/1999 |
| EP | 1621141 A2 | 2/2006 | | WO | WO 99/45849 A1 | 9/1999 |
| EP | 1621145 A2 | 2/2006 | | WO | WO 00/24322 A1 | 5/2000 |
| EP | 1621151 A2 | 2/2006 | | WO | WO 00/57796 A1 | 10/2000 |

| | | | |
|---|---|---|---|
| WO | WO 00/64365 A1 | 11/2000 |
| WO | WO 00/72762 A1 | 12/2000 |
| WO | WO 00/72765 A1 | 12/2000 |
| WO | WO 01/05072 A1 | 1/2001 |
| WO | WO 01/10482 A1 | 2/2001 |
| WO | WO 01/54594 A1 | 8/2001 |
| WO | WO 01/62158 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/020139 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A2 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
U.S. Appl. No. 12/030,424, filed Feb. 13, 2008.
U.S. Appl. No. 12/234,149, filed Sep. 19, 2008.
U.S. Appl. No. 12/234,143, filed Sep. 19, 2008.
U.S. Appl. No. 12/234,133, filed Sep. 19, 2008.
The Sodem Aseptic Battery Transfer Kit, Sodem Systems, 2000, 3 pages.
"Biomedical Coatings," Fort Wayne Metals, Research Products Corporation, obtained online at www.fwmetals.com on Jun. 21, 2010 (1 page).
U.S. Appl. No. 12/622,099, filed Nov. 19, 2009.
U.S. Appl. No. 12/622,113, filed Nov. 19, 2009.
U.S. Appl. No. 12/622,130, filed Nov. 19, 2009.

* cited by examiner

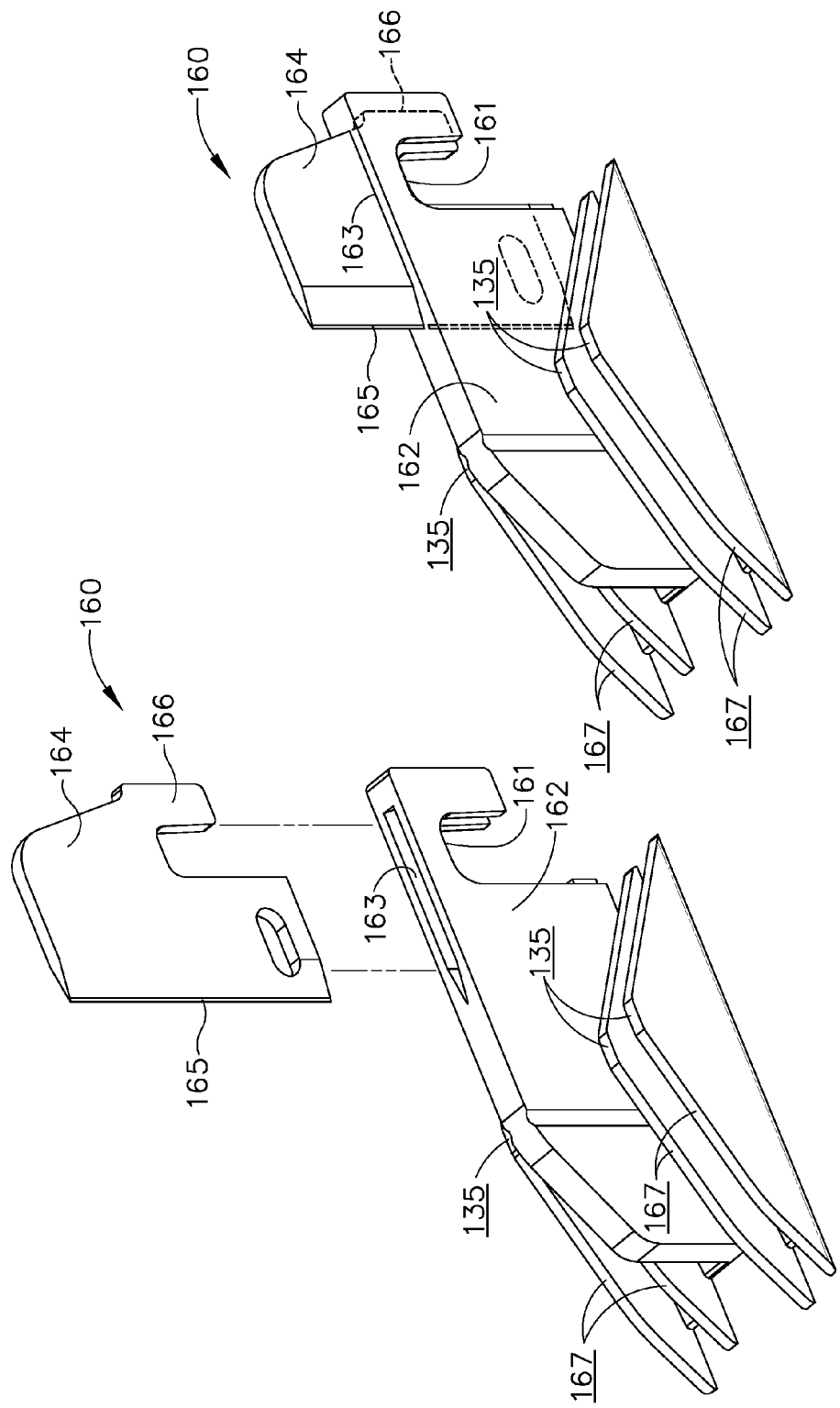

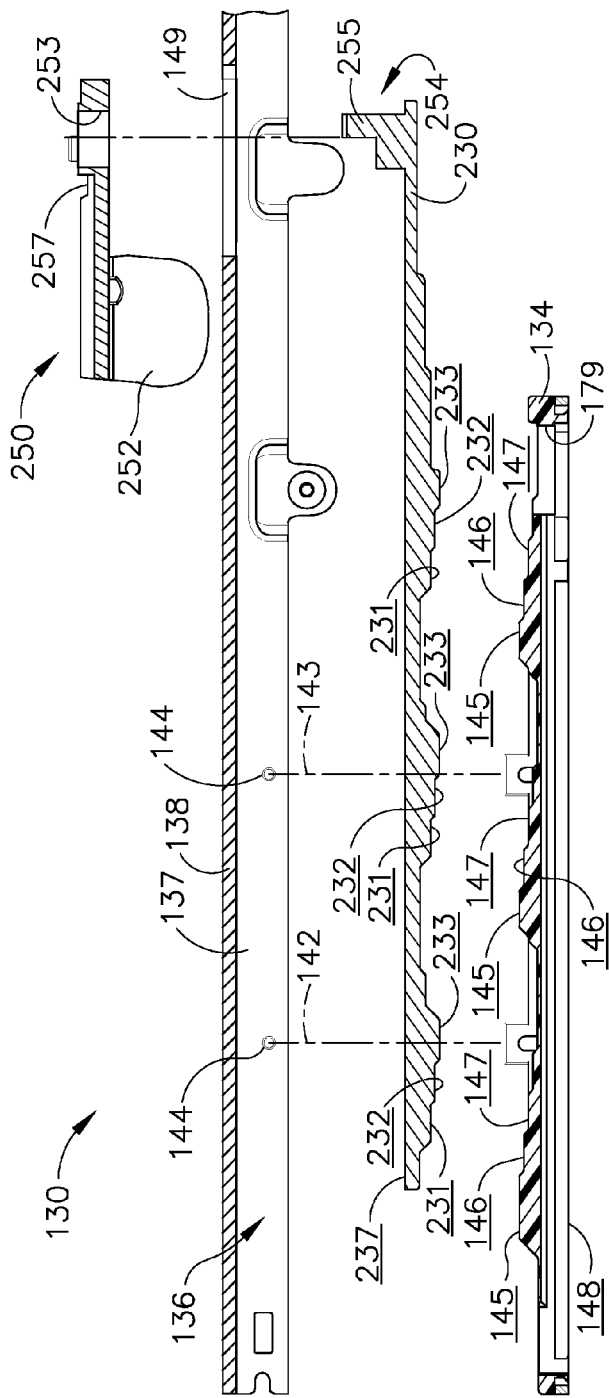
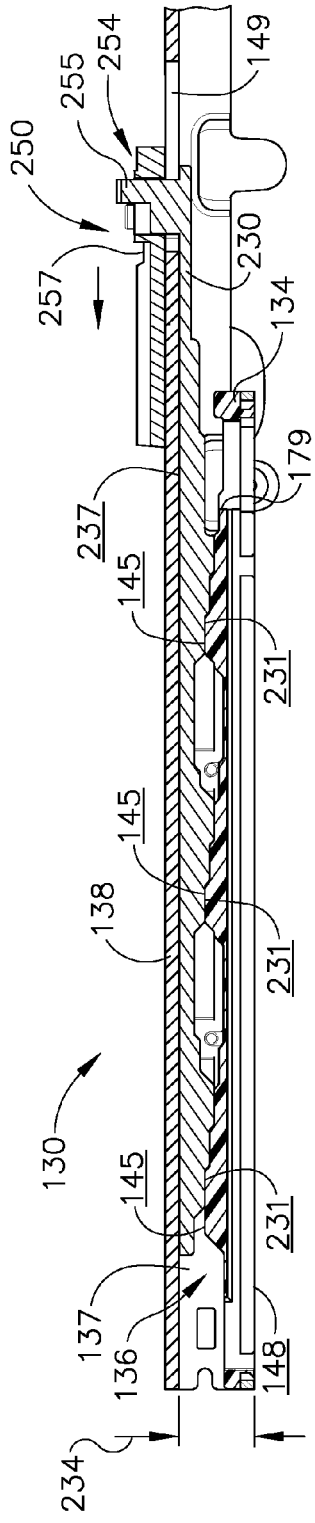
FIG. 20
FIG. 21

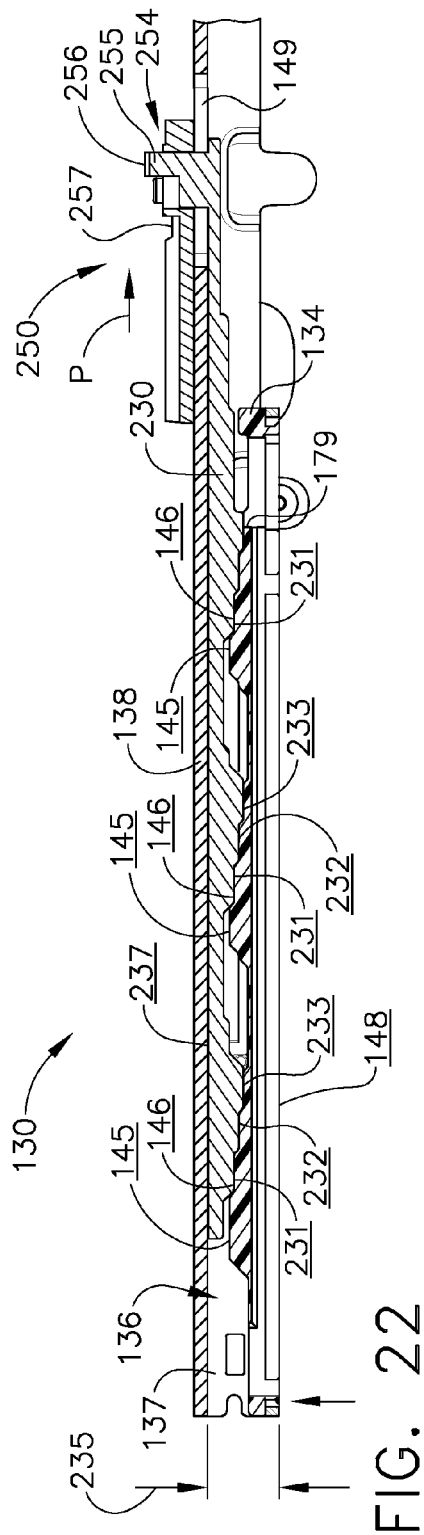
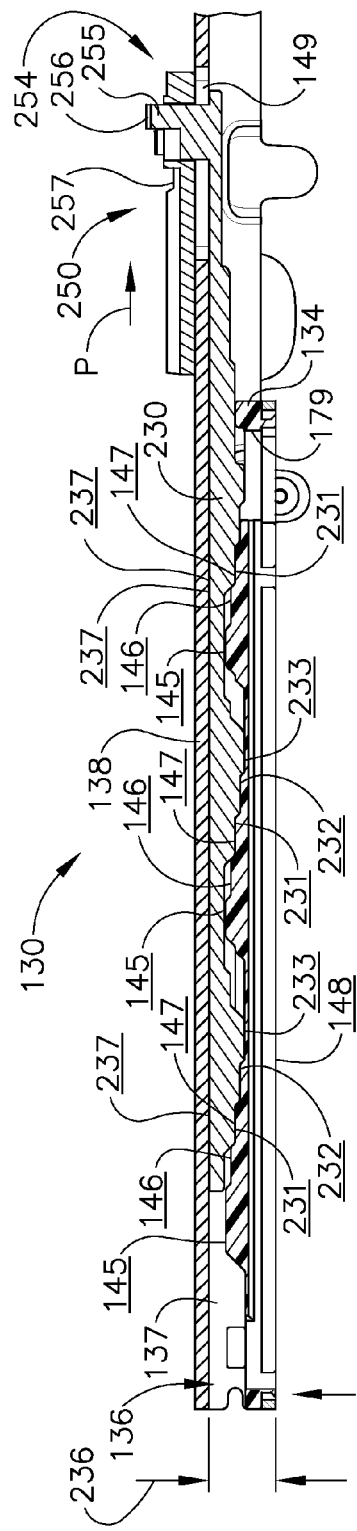

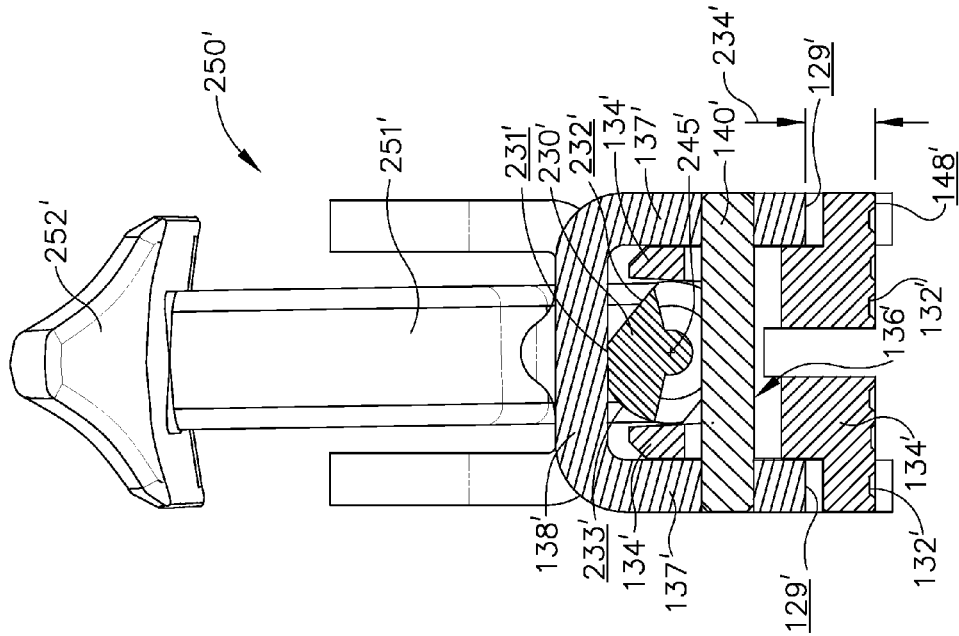
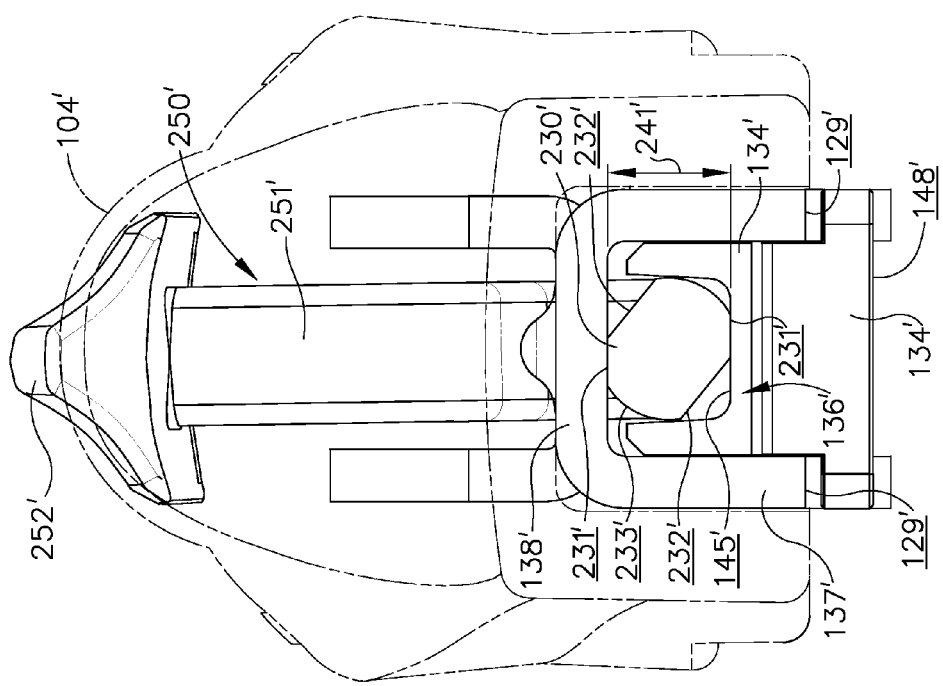

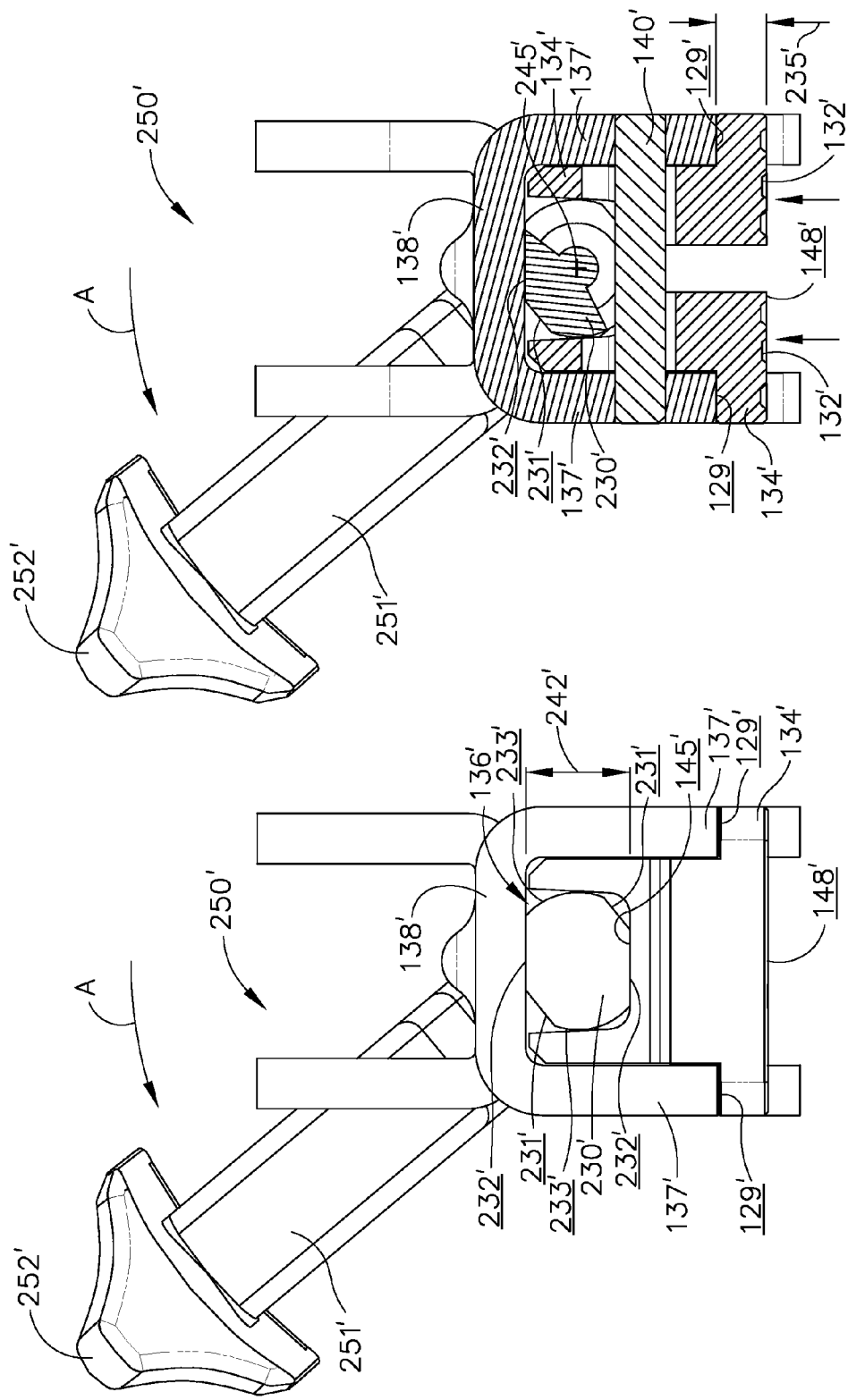

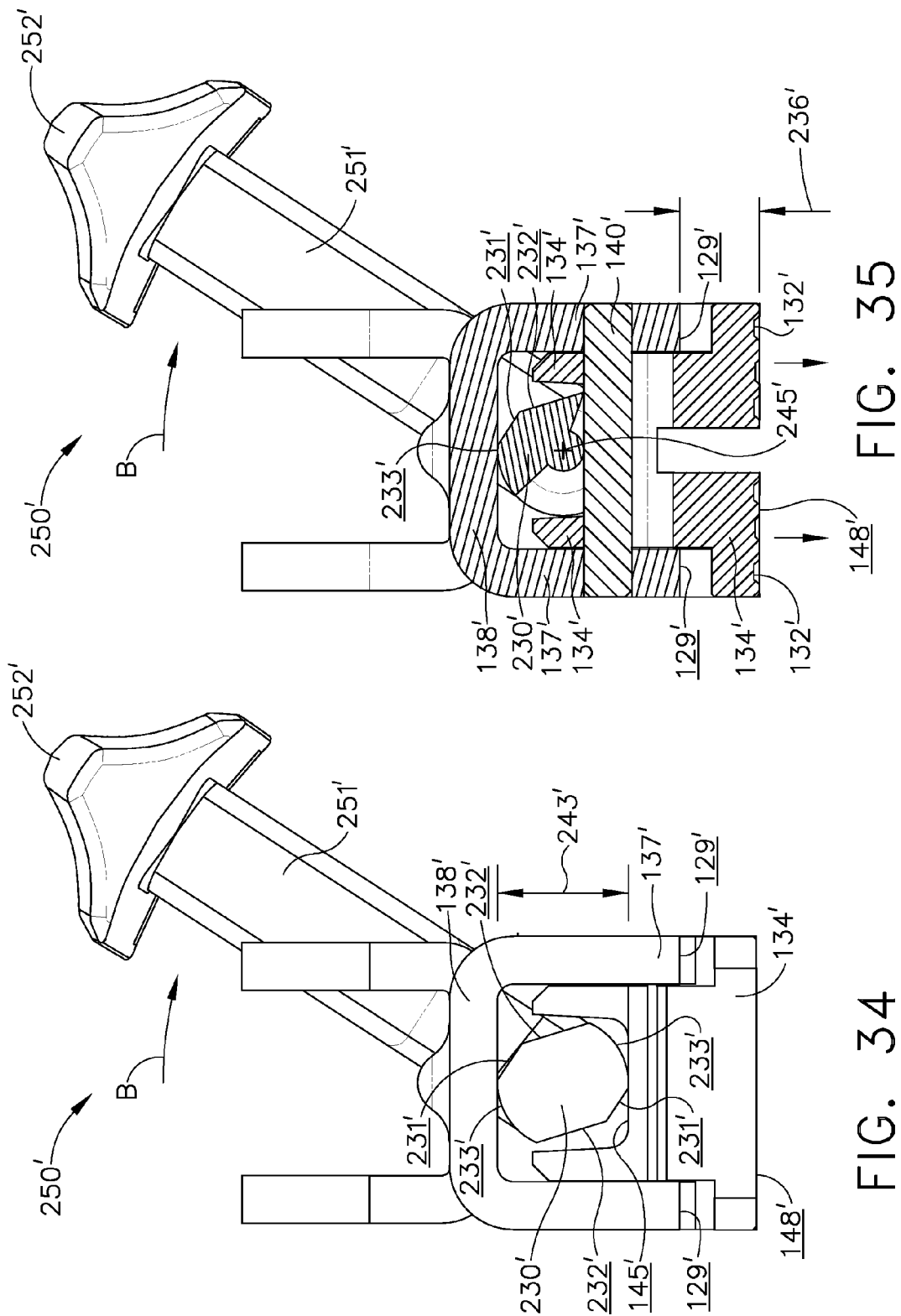

LOCKOUT ARRANGEMENT FOR A SURGICAL STAPLER

BACKGROUND i. Technical Field

The present invention relates to stapling instruments and, in various embodiments, to a surgical stapling instrument for producing one or more rows of staples.

ii. Background of the Related Art

In recent years, there has been an increasing tendency for surgeons to use stapling instruments to suture body tissues such as a lung, an esophagus, a stomach, a duodenum and/or other organs in the intestinal tract. The use of an appropriate stapling instrument in many instances may perform a better job in less time and simplify previously difficult surgical procedures such as gastrointestinal anastomoses. Previous linear two and four row cutting staplers comprised cartridge-less instruments into which staples were individually hand-loaded. Other previous devices have included a presterilized disposable staple loading unit and a cutting member which could be utilized for dividing the tissue and forming the rows of staples simultaneously. An example of such a surgical stapler is disclosed in U.S. Pat. No. 3,499,591, entitled INSTRUMENT FOR PLACING LATERAL GASTROINTESTINAL ANASTOMOSES, which issued on Mar. 10, 1970, the entire disclosure of which is hereby incorporated by reference herein.

A stapling instrument can include a pair of cooperating elongate jaw members, wherein each jaw member can be adapted to be inserted into an internal, tubular body organ to be anastomosed. In various embodiments, one of the jaw members can support a staple cartridge with at least two laterally spaced rows of staples, and the other jaw member can support an anvil with staple-forming pockets aligned with the rows of staples in the staple cartridge. Generally, the stapling instrument can further include a pusher bar and knife blade which are slidable relative to the jaw members to sequentially eject staples from the staple cartridge via camming surfaces on the pusher bar. In at least one embodiment, the camming surfaces can be configured to activate a plurality of staple drivers carried by the cartridge and associated with the individual staples to push the staples against the anvil and form laterally spaced rows of deformed staples in the tissue gripped between the jaw members. In typical stapling instruments, however, the anvil is unmovable relative to the staple cartridge once the jaw members have been assembled together and the formed height of the staples cannot be adjusted. In at least one embodiment, the knife blade can trail the pusher bar and cut the tissue along a line between the staple rows. Examples of such stapling instruments are disclosed in U.S. Pat. No. 4,429,695, entitled SURGICAL INSTRUMENTS, which issued on Feb. 7, 1984, the entire disclosure of which is hereby incorporated by reference herein.

In various embodiments, a typical stapling instrument can include first and second jaw members which can be secured together by a latch, wherein the latch can be moved between an open position, a partially-closed position, and a closed position. In the open and partially-closed positions of the latch, however, the first and second jaw members of a typical stapling instrument can be unintentionally detached from each other, thereby requiring additional time to reassemble the jaw members. In certain circumstances, the detachment of the first and second jaw members may expose a knife blade. In various circumstances, further to the above, a stapling instrument can include an actuator knob extending from the pusher bar which can be configured to be grasped by a surgeon and advanced distally to advance the pusher bar and knife blade within the staple cartridge. In certain circumstances, however, the actuator knob can be advanced relative to a jaw member eventhough the first and second jaw members have not been assembled. Once assembled, in at least one circumstance, the actuator knob, as it can extend outwardly from the surgical instrument, can unintentionally contact tissue surrounding the surgical site and, as a result, the tissue may impede the advancement of the actuator knob. In such circumstances, a surgeon may have to force the actuator knob past the tissue and/or re-position the stapling instrument which can increase the time needed to complete the surgery. What is needed is an improvement over the foregoing.

SUMMARY

In at least one form of the present invention, a surgical stapling instrument can include first and second jaw members which can be pivotably connected to each other and secured in position relative to each other by a latch. In various embodiments, the first and second jaw members can include first and second locking members which can allow the first and second jaw members to be rotated relative to one another but prevent, or at least inhibit, the first and second jaw members from being separated from one another. Such embodiments may be particularly useful in circumstances when the latch is in a partially-closed position and the first and second jaw members are being manipulated to position tissue therebetween. In at least one such embodiment, the first and second jaw members can be sufficiently connected together in order to prevent, or at least reduce the possibility of, the first and second jaw members from becoming detached from one another and exposing a cutting member. In at least one form of the present invention, a surgical stapling instrument can include a housing which can extend at least partially over and/or around the cutting member. In various embodiments, the housing can at least partially cover the cutting member when the first and second jaw members are detached from one another, yet permit the cutting member to be moved relative to the first and second jaw members during use.

In various embodiments, the surgical stapling instrument can further include a cutting member and/or staple sled which can be advanced and/or retracted relative to the first and second jaw members. In certain embodiments, the staple sled can be advanced by, and/or along with, the cutting member in order to deploy staples from a staple cartridge in one of the first and second jaw members. In at least one form of the present invention, a surgical stapling instrument can include a lock which can prevent, or at least inhibit, the cutting member and/or staple sled from being moved, or at least advanced, relative to the first and second jaw members before the latch has been closed. In at least one embodiment, the latch can be configured to engage the lock as the latch is moved from a fully open position to a fully closed position and operably disengage the lock from the cutting member and/or staple sled. In at least one embodiment, one of the first and second jaw members can include an anvil having at least one forming surface which can be configured to deform the staples as they are deployed from the staple cartridge. In at least one form of the present invention, the anvil can be movably adjustable relative to the staple cartridge in order to adjust the amount in which the staples are deformed. In various embodiments, the anvil can be adjusted by a slidable adjusting plate and/or a rotatable cam.

BRIEF DESCRIPTION OF DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 11 is an exploded view of a staple sled and cutting member assembly of the staple cartridge assembly of FIG. 8;

FIG. 12 is a perspective view of the staple sled and cutting member assembly of FIG. 11;

FIG. 20 is an exploded cross-sectional elevational view of the anvil assembly of FIG. 17;

FIG. 21 is a cross-sectional assembly view of the anvil assembly of FIG. 17 illustrating an anvil adjustment member in a first position;

FIG. 22 is a cross-sectional assembly view of the anvil assembly of FIG. 17 illustrating the anvil adjustment member of FIG. 21 in a second position;

FIG. 23 is a cross-sectional assembly view of the anvil assembly of FIG. 17 illustrating the anvil adjustment member of FIG. 21 in a third position;

FIG. 30 is an end view of the surgical stapling instrument of FIG. 24 with some components removed and others shown in dashed lines illustrating the rotatable anvil adjustment member in the first orientation of FIG. 28;

FIG. 31 is a cross-sectional end view of the surgical stapling instrument of FIG. 24 taken along line 31-31 in FIG. 24;

FIG. 32 is an end view of the surgical stapling instrument of FIG. 24 illustrating the rotatable anvil adjustment member of FIG. 28 rotated in a first direction into a second orientation;

FIG. 33 is a cross-sectional end view of the surgical stapling instrument of FIG. 24 illustrating the anvil adjustment member in the second orientation of FIG. 32;

FIG. 34 is an end view of the surgical stapling instrument of FIG. 24 illustrating the rotatable anvil adjustment member of FIG. 28 rotated in a second direction into a third orientation;

FIG. 35 is a cross-sectional end view of the surgical stapling instrument of FIG. 24 illustrating the anvil adjustment member in the third orientation of FIG. 34;

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings.

Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Three commonly-owned, non-provisional United States patent applications have been filed contemporaneously with the present application. At the time of filing, these three applications were identifiable as:

U.S. application Ser. No. 12/234,149, now U.S. Publication No. 2010/0072256, entitled SURGICAL STAPLING INSTRUMENT WITH CUTTING MEMBER ARRANGEMENT, U.S. application Ser. No. 12/234,143, now U.S. Publication No. 2010/0072253, entitled SURGICAL STAPLER HAVING AN INTERMEDIATE CLOSING POSITION, and U.S. application Ser. No. 12/234,133, now U.S. Publication No. 2010/0072252, entitled SURGICAL STAPLER WITH APPARATUS FOR ADJUSTING STAPLE HEIGHT, the entire disclosures of which are hereby incorporated by reference herein.

Figure 1:
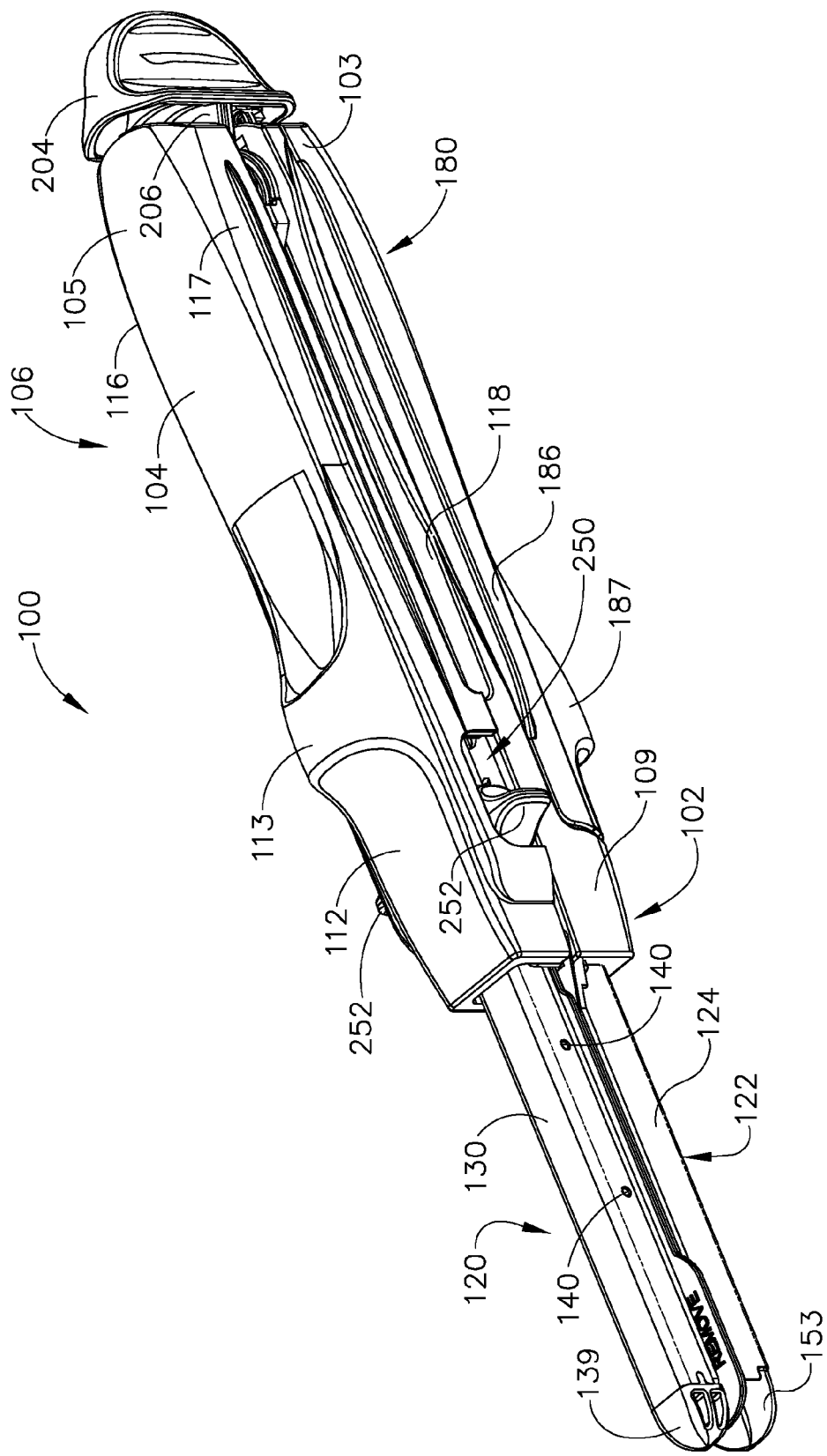
FIG. 1 is a perspective view of a surgical stapling instrument in accordance with at least one embodiment of the present invention.

Referring to FIG. 1, a surgical stapling instrument, generally 100, can comprise a first handle portion 102 and a second handle portion 104. In various embodiments, first handle portion 102 and second handle portion 104 can be configured to be grasped by a surgeon, for example, and can comprise hand grip portion 106. In at least one embodiment, first handle portion 102, referring to FIGS. 2 and 3, can include a first cover 108 attached to a first frame 110 and, similarly, second handle portion 104 can include a second cover 112 attached to a second frame 114. Covers 108 and 112 can be ergonomically contoured, or otherwise suitably contoured, to assist a surgeon in manipulating stapling instrument 100 within a surgical site. In various embodiments, handle covers 108 and 112, for example, can include enlarged protrusions 109 and 113, respectively, which can facilitate the insertion of stapling instrument 100 into a surgical site. In various embodiments, handle covers 108 and 112 can be made of plastic, lightweight materials, and/or any other suitable material, for example, while handle frames 110 and 114 can be made of stainless steel, titanium, and/or any other suitable material, for example.

Figure 2:
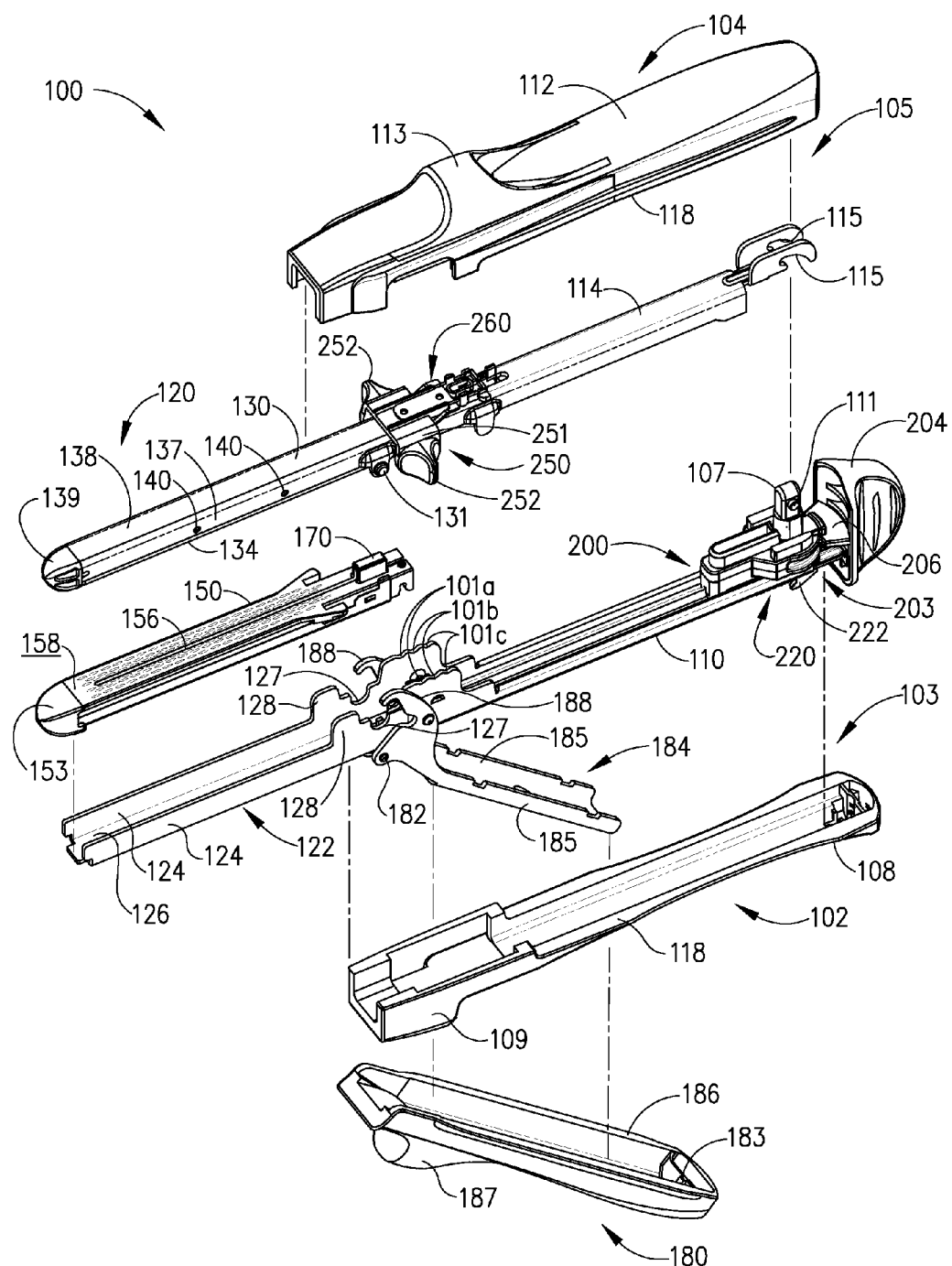
FIG. 2 is an exploded perspective view of the surgical stapling instrument of FIG. 1.

In various embodiments, referring again to FIGS. 1-3, the distal ends of handle portions 102 and 104 can comprise an end-effector 120 which can be configured to treat tissue within a surgical site, for example. In at least one such embodiment, end-effector 120 can include a staple cartridge channel 122 configured to receive and/or retain a staple cartridge as described in greater detail further below. In certain embodiments, staple cartridge channel 122 can comprise a one-piece elongated channel-shaped frame extending from first handle portion frame 110. In at least one embodiment, staple cartridge channel 122 can include a pair of opposed, elongated side walls 124 connected by a bottom wall 126. Along the rearward, or proximal, portion of staple cartridge channel 122, a pair of spaced, upstanding side flanges 128 can extend upwardly from opposed side walls 124. In various embodiments, the width of staple cartridge channel 122 between side flanges 128 can be greater than the width of the upper jaw member, or anvil, 130 extending from second handle portion 104. In at least one embodiment, the distance between flanges 128 can be configured to permit at least a portion of anvil 130 to be received between side flanges 128 when the stapling instrument is assembled for operation. As shown in FIG. 2, each side flange 128 of can include a notch, or recess, 127, for example, which can be configured to receive one or more latch projections 131, for example, extending from anvil 130, and/or any other suitable portion of second handle portion 104, as described in greater detail further below.

Figure 9:
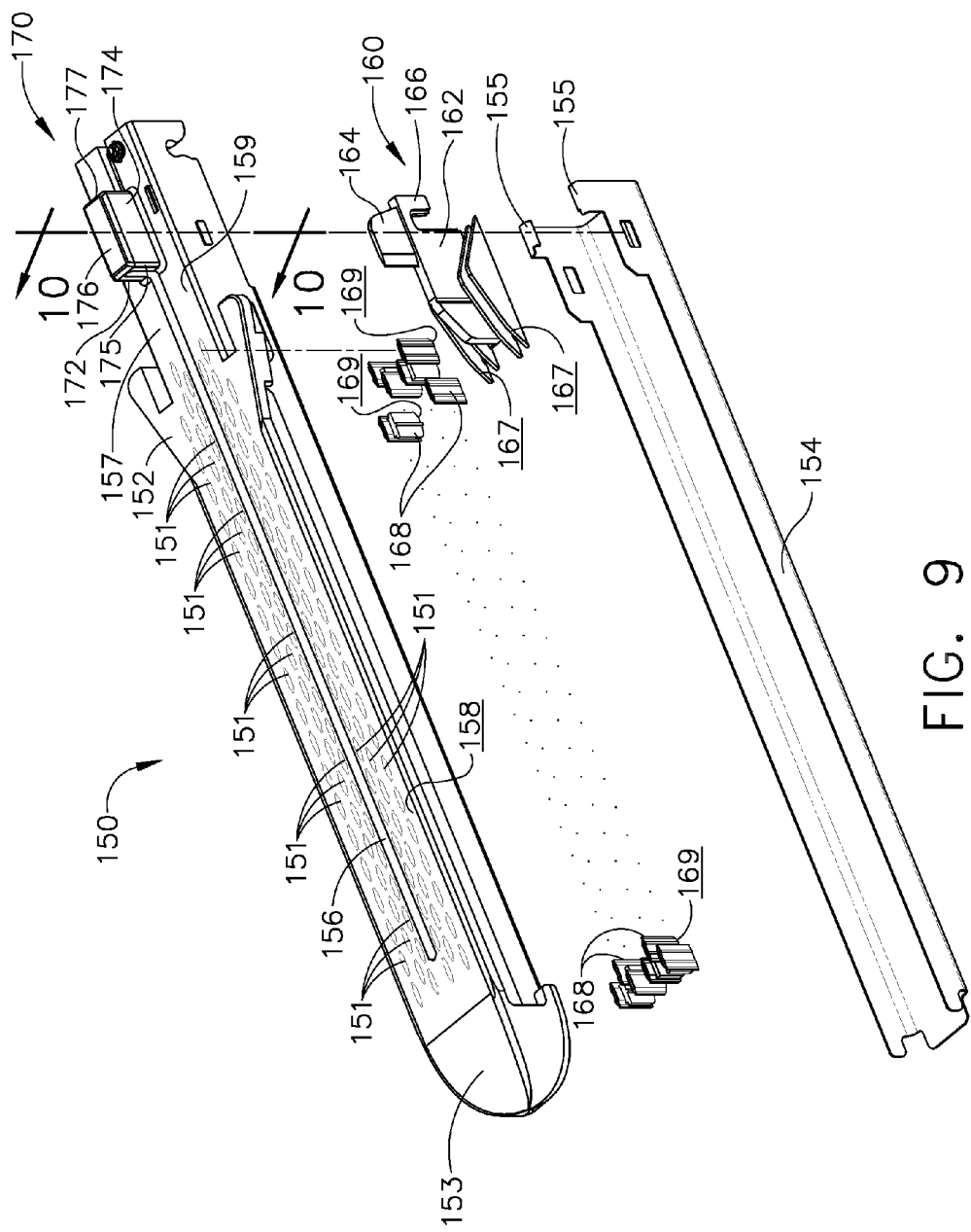
FIG. 9 is an exploded view of the staple cartridge assembly of FIG. 8.
Figure 10:
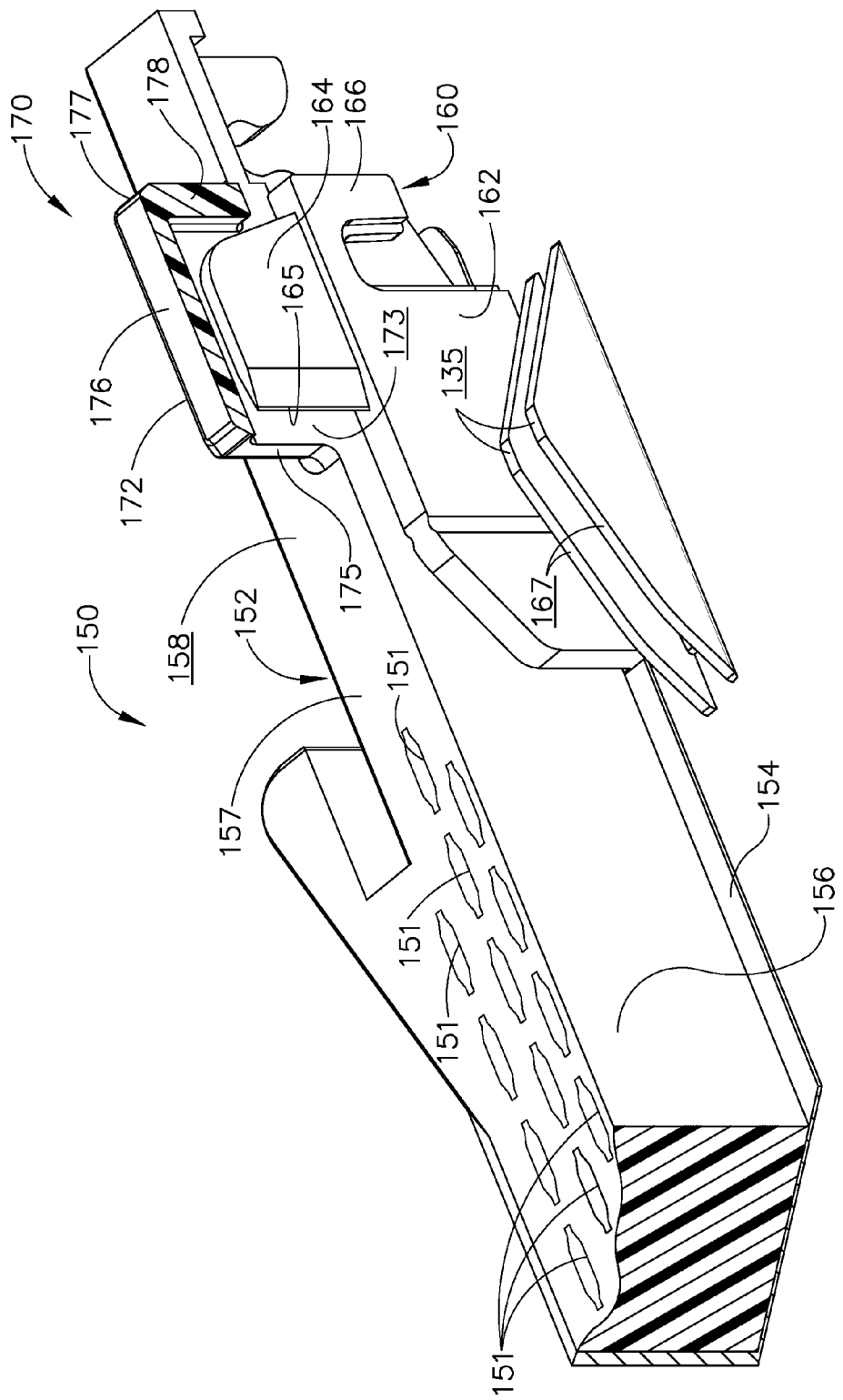
FIG. 10 is a cross-sectional view of the staple cartridge assembly of FIG. 8 taken along line 10-10 in FIG. 9.

As indicated above, referring once again to FIGS. 1-3, staple cartridge channel 122 can be configured to support and/or retain a staple cartridge, such as staple cartridge 150, for example, within end-effector 120, wherein the staple cartridge can include one or more staples (not illustrated) removably stored therein. In various embodiments, referring to FIGS. 8-10, staple cartridge 150 can include one or more staple cavities 151 which can be configured to store staples in any suitable arrangement, such as in at least two laterally-spaced longitudinal rows, for example. In at least one embodiment, referring to FIGS. 9 and 10, staple cartridge 150 can include staple cartridge body 152 and pan 154, wherein staple cartridge body 152 and/or pan 154 can be configured to define a channel, or path, for slidably receiving a staple sled and/or cutting member therein. In at least one embodiment, pan 154 can include flexible arms 155, for example, which can be configured to engage staple cartridge body 152 in a snap-fit and/or press-fit arrangement. Referring to FIGS. 10-12, staple cartridge 150 can further include staple sled assembly 160 which can include staple sled portion 162 and, in addition, cutting member 164. In various embodiments, cutting member 164 can include cutting edge 165 and lock arm 166, for example, wherein lock arm 166 can be configured to be press-fit and/or snap-fit into aperture 163 in staple sled 162 when cutting member 164 is assembled to staple sled portion 162. In other various embodiments, staple sled portion 162 can be integrally molded to cutting member 164.

Figure 8:
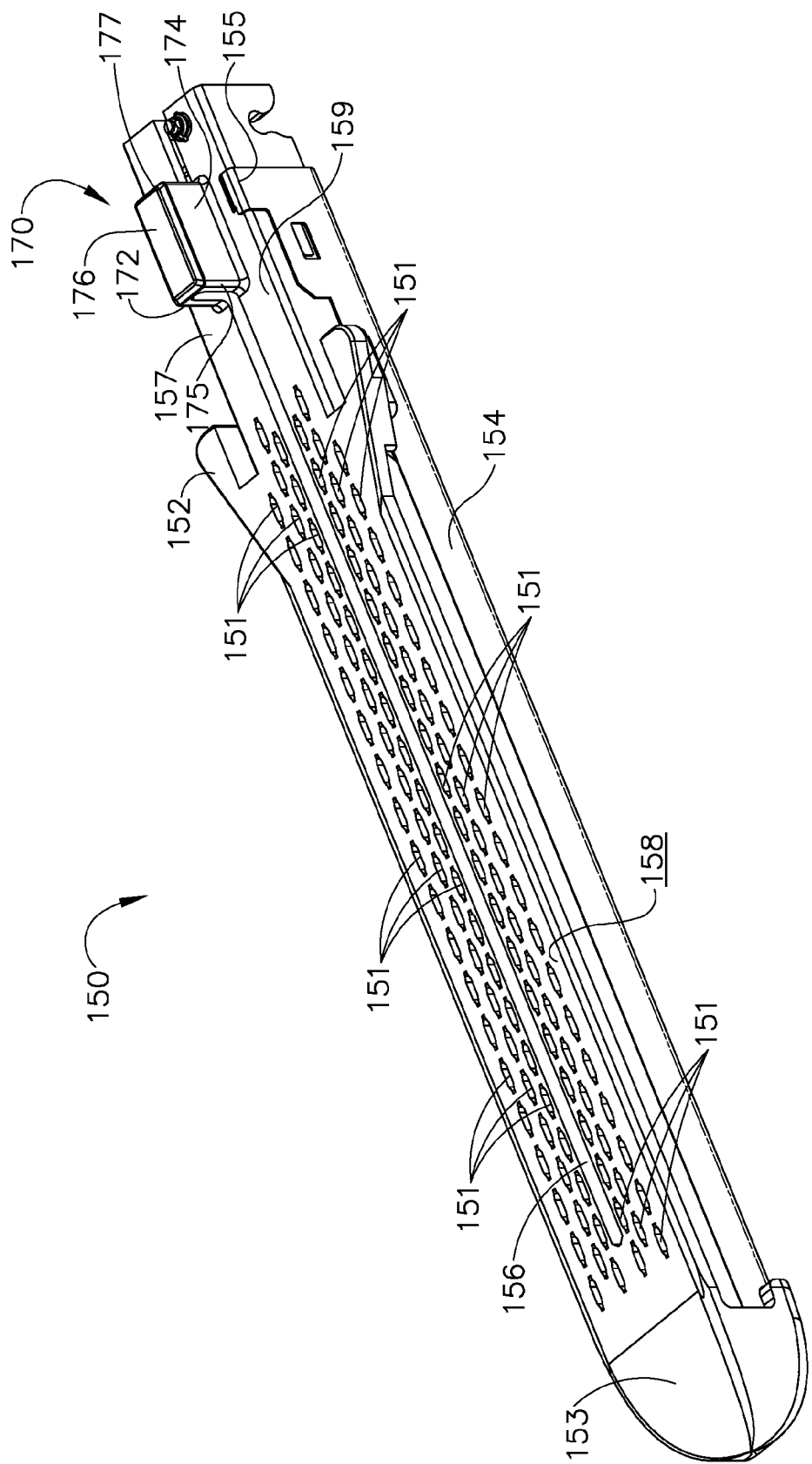
FIG. 8 is a perspective view of a staple cartridge assembly of the surgical stapling instrument of FIG. 1.

Further to the above, referring to FIGS. 8-10, staple cartridge body 152 can include a slot, such as slot 156, for example, which can be configured to receive at least a portion of cutting member 164 therein, and/or any other portion of staple sled assembly 160 and pusher bar assembly 200 (discussed below), wherein slot 156 can be configured to permit cutting member 164 to be moved between first and second positions within staple cartridge 150. In various embodiments, slot 156 can be configured to permit cutting member 164 to be moved between a proximal position (FIG. 10) and a distal position in order to incise tissue positioned intermediate staple cartridge 150 and anvil 130, for example. Referring again to FIGS. 10-12, staple sled portion 162 can include cam, ramp, or actuator, surfaces 167 which can be configured to engage staple drivers positioned within staple cartridge 150. In various embodiments, referring to FIG. 9, staple cartridge 150 can include staple drivers 168 which can be lifted, or slid, upwardly within staple cavities 151 by sled portion 162 such that the upward movement of staple drivers 168 can eject, or deploy, staples at least partially positioned within staple cavities 151. While staple drives 168 can be, in fact, lifted vertically upwardly, the term upward, and the like, can mean that staple drivers 168, for example, are moved toward the top surface, or deck, 158 of the staple cartridge and/or toward anvil 130, for example. In certain embodiments, as illustrated in FIG. 9, each staple driver 168 can include one or more sloped surfaces 169 oriented at the same angle as a cam surface 167, and/or any other suitable angle, which can provide a relatively flat, or at least substantially flat, sliding contact surface between staple sled 162 and staple drivers 168. In various embodiments, a staple driver can be configured to deploy only one staple, while, in certain embodiments, a staple driver can be configured to simultaneously deploy two or more staples located in adjacent rows, for example. Other devices are disclosed in U.S. patent application Ser. No. 12/030,424, entitled SURGICAL STAPLING INSTRUMENT WITH IMPROVED FIRING TRIGGER ARRANGEMENT, which was filed on Feb. 13, 2008, the entire disclosure of which is incorporated by reference herein.

In various embodiments, as described above, a surgical stapling instrument can include a cutting member/staple sled assembly configured to incise tissue and deploy staples from a staple cartridge. In certain embodiments, though, a surgical stapling instrument may not require, or include, a cutting member. In at least one such embodiment, a staple cartridge can include a staple sled positioned therein and/or a surgical instrument can be configured to move a staple sled into a staple cartridge in order to staple tissue, for example, without otherwise dissecting it. In certain other embodiments, a staple cartridge can include a staple sled positioned therein where a surgical instrument can include a cutting member movable into, or relative to, the staple cartridge. In at least one such embodiment, the cutting member can be advanced into contact with the staple sled such that the cutting member and staple sled can be advanced together. Thereafter, the cutting member can be sufficiently retracted to allow the staple cartridge to be detached from the surgical instrument and replaced with a new staple cartridge having a new staple sled. Such embodiments may be useful when a staple sled may become worn or deformed during use. Other embodiments are envisioned where a staple cartridge can include a cutting member positioned therein where a surgical instrument can include a staple sled movable into, or relative to, the staple cartridge. In at least one such embodiment, similar to the above, the staple sled can be advanced into contact with the cutting member such that the cutting member and staple sled can be advanced together. Thereafter, the staple sled can be sufficiently retracted to allow the staple cartridge to be detached from the surgical instrument and replaced with a new staple cartridge having a new cutting member. Such embodiments may be useful when a cutting member may become worn or deformed during use. In various embodiments, as described in greater detail below, the staple cartridge can include a protective housing or cover configured to prevent, or at least reduce the possibility of, a surgeon or other clinician from touching the cutting member positioned within the staple cartridge while handling the staple cartridge, for example.

Figure 3:
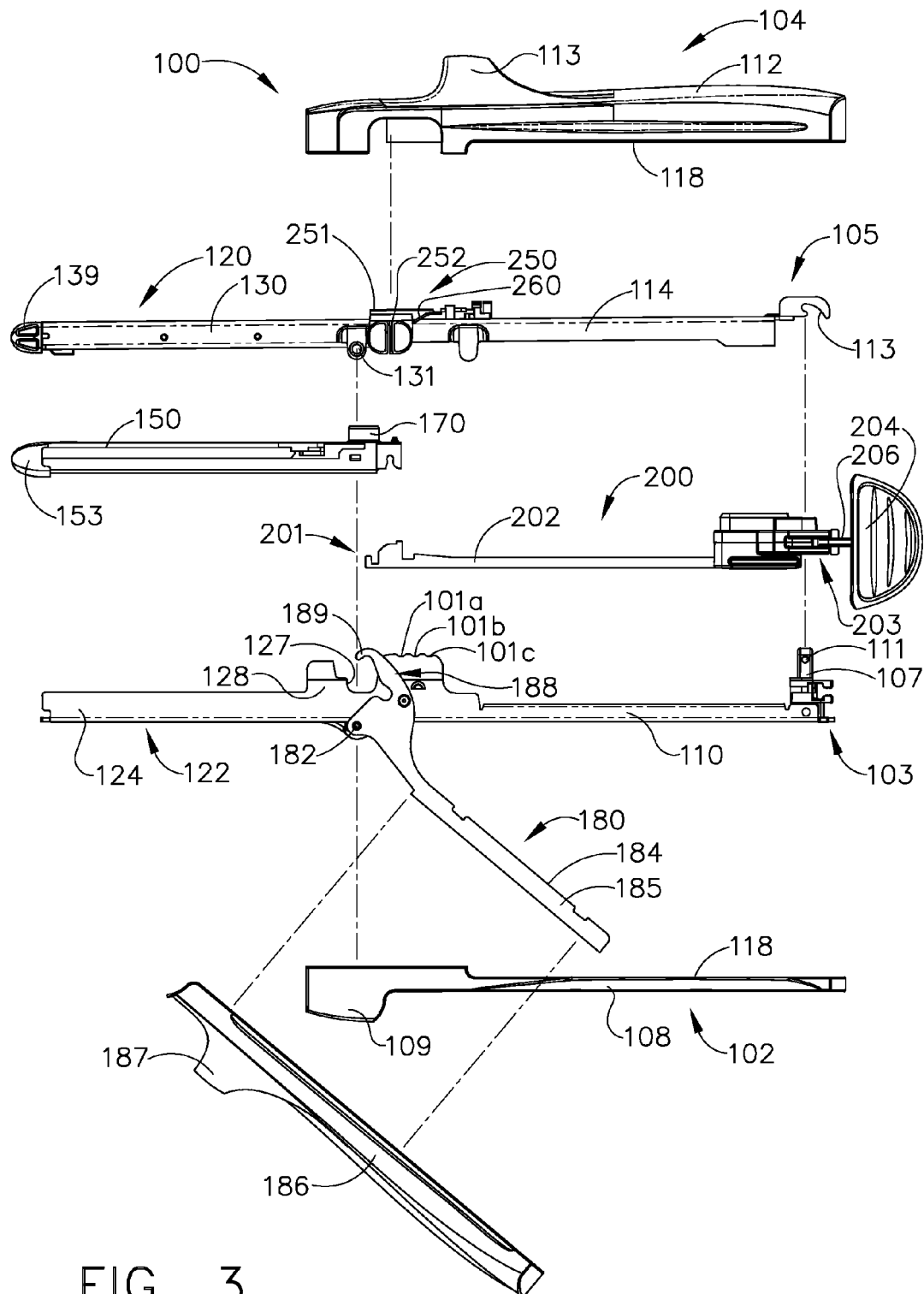
FIG. 3 is an exploded elevational view of the surgical stapling instrument of FIG. 1.

In various embodiments, further to the above, staple cartridge channel 122 and/or staple cartridge 150, for example, can include one or more co-operating projections and/or recesses, for example, which can be configured to removably retain staple cartridge 150 within staple cartridge channel 122. Once staple cartridge 150 has been inserted into staple cartridge channel 122, in various embodiments, the first handle portion 102 can be assembled to the second handle portion 104. In other various embodiments, the staple cartridge may be inserted into the staple cartridge channel after the first and second handle portions have been assembled together. In either event, referring to FIGS. 1-7, first handle portion 102 and second handle portion 104 can include proximal ends 103 and 105, respectively, which can be assembled together such that the first and second handle portions can be rotatably or pivotably coupled to one another. In various embodiments, referring to FIGS. 2 and 3, first handle portion 102 can include one or more pins, or projections, 111 extending therefrom which can be configured to be slidably received within one or more grooves, channels, or slots 115 in second handle portion 104. In certain embodiments, slots 115 can be defined in second handle frame 114 and projections 111 can extend from a proximal end post 107 extending from first handle frame 110, for example. In order to assemble first handle portion 102 and second handle portion 104, referring to FIG. 4, the open ends of slots 115 can be aligned with projections 111 such that second handle portion 104, for example, can be translated relative to first handle portion 102 and projections 111 can be slid within slots 115. In at least one embodiment, as illustrated in FIGS. 2 and 3, the open ends of slots 115 can be located proximally with respect to their closed ends. In at least one such embodiment, proximal end 105 of second handle portion 104 can be positioned distally with respect to proximal end 103 of first handle portion 102 such that second handle portion 104 can be moved proximally in order to position projections 111 within slots 115. In various other circumstances, first handle portion 102 can be positioned proximally with respect to second handle portion 104 and slid distally in order to position projections 111 within slots 115.

Figure 5:
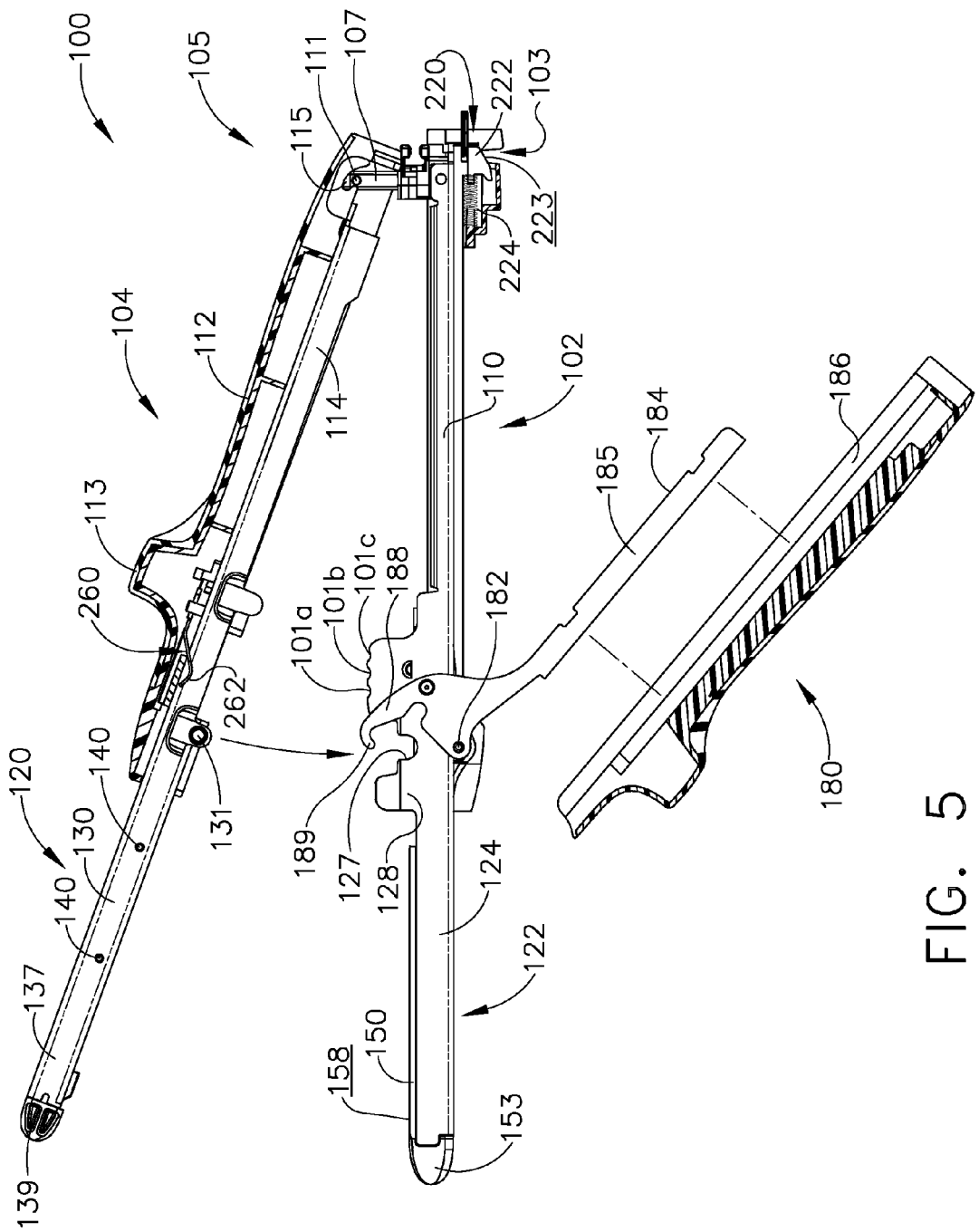
FIG. 5 is a partial cross-sectional view of the surgical stapling instrument of FIG. 1 illustrating the proximal end of the first portion of FIG. 4 being locked to the proximal end of the second portion of FIG. 4 and illustrating the second portion being rotated toward the first portion.
Figure 6:
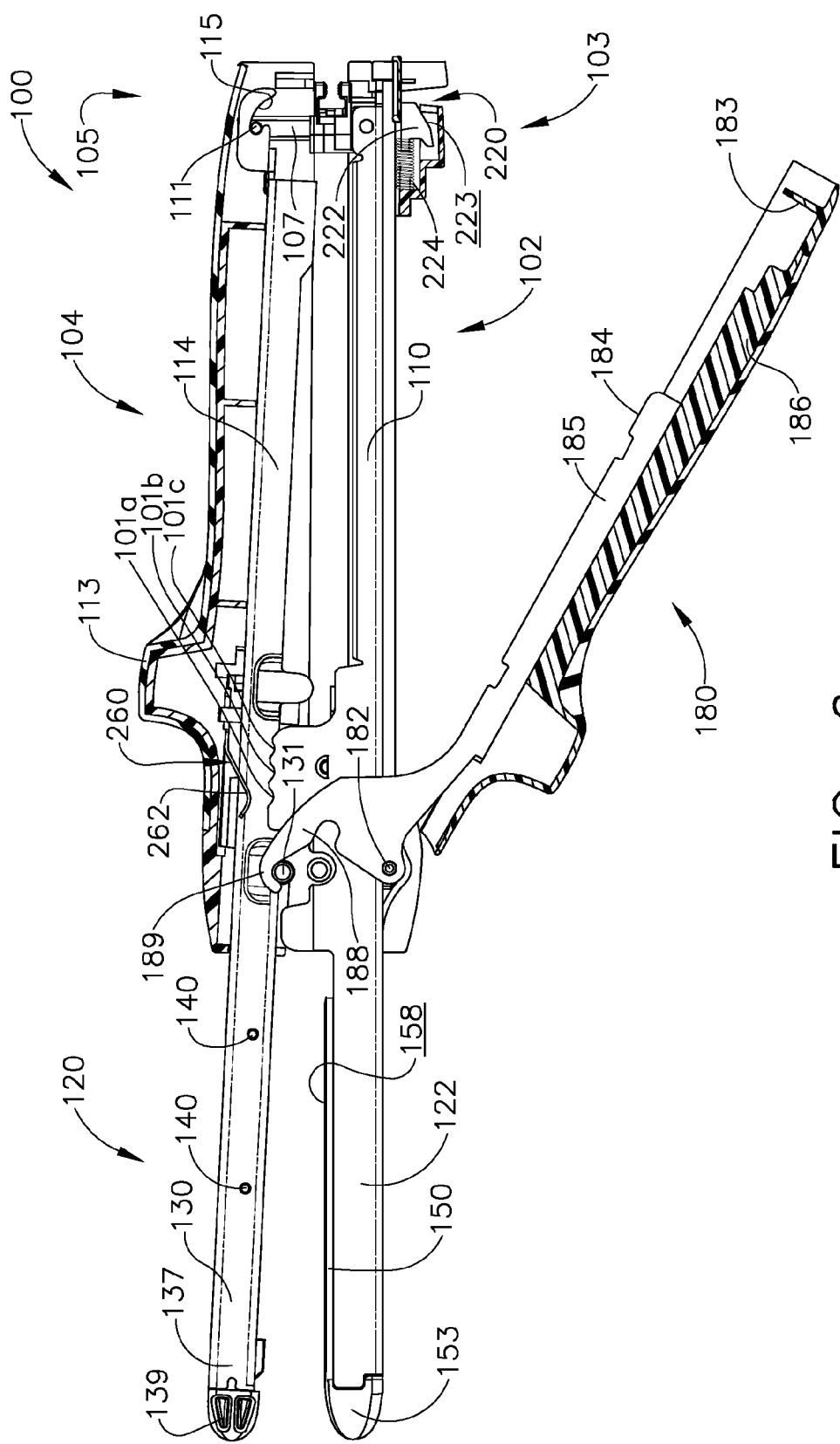
FIG. 6 is a partial cross-sectional view of the surgical stapling instrument of FIG. 1 illustrating a latch rotatably mounted to the first portion, wherein the latch is engaged with the second portion and wherein the latch has been rotated into a partially-closed position.

In various embodiments, referring to FIG. 5, second handle portion 104 can be rotated toward first handle portion 102 such that anvil 130 can be moved into position relative to staple cartridge 150 and/or staple cartridge channel 122. In certain embodiments, first handle portion 102 can be rotated toward second handle portion 104 and/or the first and second handle portions can be rotated toward each other. In any event, projections 111 and slots 115, when engaged with one another, can comprise a pivot about which one or both of the first and second handle portions can be moved relative to each other. In various embodiments, second handle portion 104 can be moved relative to first handle portion 102 such that anvil 130 is moved into close opposition to staple cartridge 150. In certain embodiments, referring to FIG. 6, second handle portion 104 can be moved relative to first handle portion 102 such that latch projections 131 extending from second handle portion 104 can be aligned with and/or inserted into recesses 127 within first handle portion 102. In various embodiments, referring primarily to FIGS. 2 and 3, first handle portion 102 can further include latching mechanism 180 rotatably mounted thereto which can be utilized to engage latch projections 131 extending from second handle portion 104 and secure the first and second handle portions together. Although not illustrated, other embodiments are envisioned in which a latching mechanism is rotatably mounted to the second handle portion and latch projections can extend from the first handle portion. In any event, in at least one embodiment, latching mechanism 180 can be mounted to first frame 110 by one or more pivot pins 182 which can be configured to define an axis about which latch 180 can be rotated.

Figure 4:
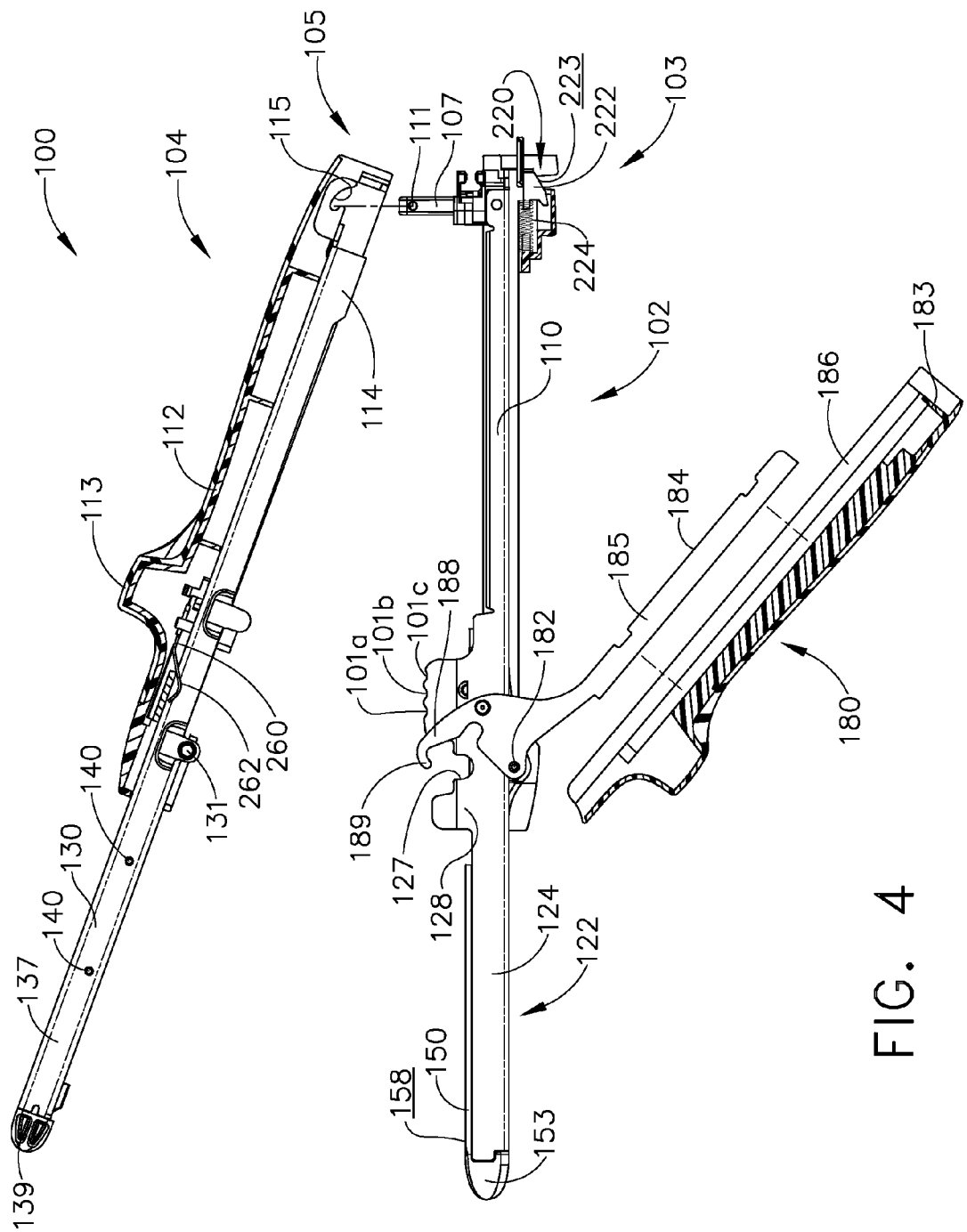
FIG. 4 is a partial cross-sectional view of the surgical stapling instrument of FIG. 1 illustrating first and second portions being assembled together.
Figure 7:
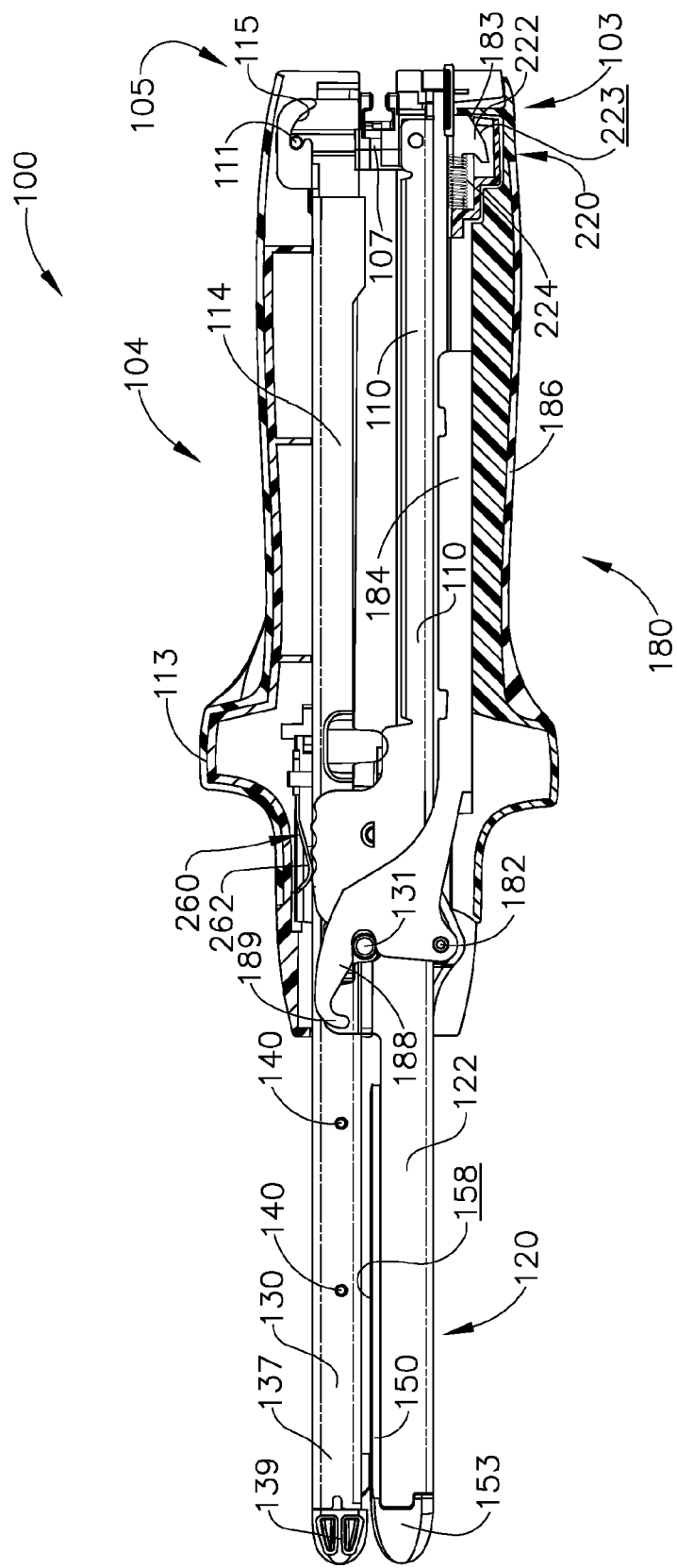
FIG. 7 is a partial cross-sectional view of the surgical stapling instrument of FIG. 1 illustrating the latch of FIG. 6 in a closed position.

In certain embodiments, referring now to FIGS. 4 and 5, latching mechanism 180 can include latch frame 184 and, in addition, latch cover 186 assembled to latch frame 184. In other various embodiments, the latch cover and the latch frame can comprise an integral unit or, in certain embodiments, the latching mechanism may not even include a cover. In certain embodiments, latch frame 184 can be channel-shaped and can include a pair of opposed, elongated side walls 185 which are spaced apart by a distance sufficient to span first frame portion 110. In at least one embodiment, latch cover 186 can be made of plastic, lightweight materials, and/or any other suitable materials, for example, while latch frame 184 can be made of stainless steel and/or any other suitable material, for example. In certain embodiments, when latching mechanism 180 is closed, as illustrated in FIG. 7, latch cover 186 can be aligned with first handle cover 108. Latch cover 186 can include contoured portion 187 which can be configured to assist a surgeon in manipulating surgical instrument 100 wherein, in at least one embodiment, contoured portion 187 can be aligned with, or at least substantially aligned with, protrusion 109 extending from first handle cover 108. Latching mechanism 180 can further include one or more latch arms 188 extending therefrom which can be configured to engage one or more latch projections 131 extending from second handle portion 104 and pull and/or secure projections 131 within recesses 127 as illustrated in FIG. 7. In at least one embodiment, at least one of latch arms 188 can be integrally-formed with latch frame 184. In certain embodiments, referring to FIG. 6, at least one of latch arms 188 can include a distal hook 189 which can be configured to wrap around at least a portion of projections 131 so as to encompass or surround, or at least partially encompass or surround, projections 131. In at least one embodiment, latch arms 188 can act as an over-center latch to maintain latching mechanism 180 in its latched, or closed, position.

In use, in various circumstances, one of the first handle portion 102 and the second handle portion 104 can be positioned on a first side of tissue within a surgical site and the other handle portion can be rotated into position on the opposite side of the tissue. In such embodiments, staple cartridge 150 can be positioned on one side of the tissue and anvil 130 can be positioned on the other side of the tissue. Thereafter, as also outlined above, latching mechanism 180 can be actuated such that it can be moved between an open position and a closed position in order to latch second handle portion 104 to first handle portion 102 and apply a clamping force to the tissue positioned between staple cartridge 150 and anvil 130. In certain circumstances, latching mechanism 180 can be moved between an open position (FIG. 5), a partially-closed, or intermediate, position (FIG. 6), and a closed position (FIG. 7). In at least one such embodiment, referring to FIGS. 5 and 6, latching mechanism 180 can be moved between an open position in which latch arms 188 are not engaged with projections 131 and a partially-closed position in which latch arms 188 are engaged with projections 131 such that, although anvil 130 has been at least partially brought into opposition to staple cartridge 150, a sufficient gap can remain between anvil 130 and staple cartridge 150 which can allow end-effector 120 to be repositioned relative to the tissue, for example. Once the anvil 130 and staple cartridge 150 have been sufficiently positioned relative to the tissue, latching mechanism 180 can be moved between its partially-closed position and a closed position, as illustrated in FIG. 7.

In various embodiments, further to the above, a surgical stapling instrument can further include a biasing member which can be configured to bias the first handle portion of a stapling instrument away from a second handle portion. In at least one embodiment, as described in greater detail further below, a spring, and/or any suitably resilient material, can be positioned intermediate the first and second handle portions such that the anvil and staple cartridge of the stapling instrument can be biased away from each other. In certain embodiments, the spring can be configured to at least partially separate the first and second handle portions such that a gap exists between the anvil and the staple cartridge, wherein the gap can be sufficient to allow tissue to be positioned therebetween. In use, a surgeon can position such a surgical stapling instrument without having to separate and hold the first and second handle portions apart from each other. Such an instrument may be especially useful when the stapling instrument is in a partially-closed configuration and the surgeon is manipulating the instrument within a surgical site. After the surgeon is satisfied with the positioning of the stapling instrument, the surgeon can compress and/or disengage the spring and place the stapling instrument in a closed configuration.

In various circumstances, as outlined above, the distal end of first handle portion 102 can be moved relative to the distal end of second handle portion 104, especially when latching mechanism 180 is not engaged with, or only partially engaged with, projections 131 of second handle portion 104. In such circumstances, projections 111 and slots 115 at the proximal ends of the first and second handle portions can be configured to retain at least the proximal ends of the first and second handle portions together when the distal ends of the first and second handle portions are being moved relative to each other, for example. Stated another way, projections 111 and slots 115 can cooperate to prevent, or at least inhibit, first handle portion 102 from becoming completely detached from second handle portion 104. In certain embodiments, a first handle portion can include a first lock portion and a second handle portion can include a second lock portion, wherein the first and second lock portions can be configured to be engaged with one another and prevent the first handle portion from becoming completely detached from the second handle portion. In at least one embodiment, projections 111 can comprise the first lock portion and slots 115 can comprise the second lock portion. Previous stapling instruments lacked such lock portions and instead relied on a sole latching mechanism to keep the first and second handle portions together. In circumstances where the latching mechanisms of these previous stapling instruments were not fully engaged with both of the first and second handle portions, the first and second handle portions could become completely detached from one another, thereby requiring a surgeon, for example, to reposition and reassemble the handle portions. In certain circumstances, a complete detachment of the first and second handle portions of these previous staples could expose at least a portion of a cutting member.

In various embodiments, as outlined above, latching mechanism 180 can be configured to be moved between an open position, a partially-closed position, and a closed position. When latching mechanism 180 is in its open position, as also outlined above, projections 111 can be inserted into and/or removed from slots 115. When latching mechanism 180 is in its partially-closed position, referring to FIG. 6, latch arms 188 can be configured to engage latch projections 131 such that projections 111 cannot be removed from slots 115. In at least one such embodiment, latch arms 188 and latch projections 131 can be configured to prevent, or at least inhibit, second handle portion 104 from being moved distally with respect to first handle portion 102 and, as a result, prevent, or at least inhibit, projections 111 from being disengaged from slots 115. Correspondingly, latch arms 188 and latch projections 131 can be configured to prevent first handle portion 102 from being moved proximally with respect to second handle portion 104. Similar to the above, in various embodiments, latch arms 188 and latch projections 131 can also be configured to prevent, or at least inhibit, projections 111 from being removed from slots 115 when latching mechanism 180 is in its closed position (FIG. 7). In certain embodiments, further to the above, latch projections 131 can extend from second handle portion 104 at a location which is intermediate its proximal and distal ends. In at least one such embodiment, projections 111 and slots 115 can be configured to hold the first and second handle portions together at their proximal ends while latching mechanism 180 can be utilized to hold the first and second handle portions together at an intermediate location. In any event, in certain embodiments, the first and second handle portions cannot be disengaged from one another unless latching mechanism 180 is moved into its fully open position. In at least one such embodiment, projections 111 and slots 115 cannot be disengaged from one another when latching mechanism 180 is in a closed and/or partially-closed position.

Once anvil 130 and staple cartridge 150 have been sufficiently positioned, the tissue positioned intermediate anvil 130 and staple cartridge 150 can be stapled and/or incised. In various embodiments, referring to FIG. 3, surgical stapling instrument 100 can further include pusher bar assembly 200 which can be configured to advance and/or retract staple sled assembly 160 within staple cartridge 150, for example. In at least one embodiment, pusher bar assembly 200 can include pusher bar 202 and firing actuator 204, wherein firing actuator 204 can be configured to move pusher bar 202 and staple sled assembly 160 distally to deploy staples from staple cartridge 150 and deform the staples against anvil 130 as described above. In at least one embodiment, referring to FIGS. 11 and 12, staple sled 162 can include a groove, channel, or slot 161 which can be configured to receive, and can be operably connected to, a distal end 201 (FIG. 3) of pusher bar 202. In certain embodiments, staple sled assembly 160 can be operably engaged with pusher bar 202 when staple cartridge 150 is inserted into staple cartridge channel 122. In at least one embodiment, distal end 201 and slot 161 can include cooperating features which can allow distal end 201 and slot 161 to be assembled in a transverse direction but prevent, or at least inhibit, distal end 201 and slot 161 from being disassembled from one another in a proximal direction and/or distal direction. In other embodiments, pusher bar 202 can be advanced distally before contacting and engaging staple sled assembly 160. In at least one such embodiment, the staple sled assembly 160 can remain stationary until contacted by pusher bar 202. In any event, as outlined above, actuator 204 can be operably connected to pusher bar 202 such that a pushing and/or pulling force can be applied to actuator 204 and transmitted to pusher bar 202. In certain embodiments, as described in greater detail below, actuator 204 can be pivotably connected to a proximal end 203 of pusher bar 202 such that actuator 204 can be selectively rotated between at least first and second positions.

Figure 13:
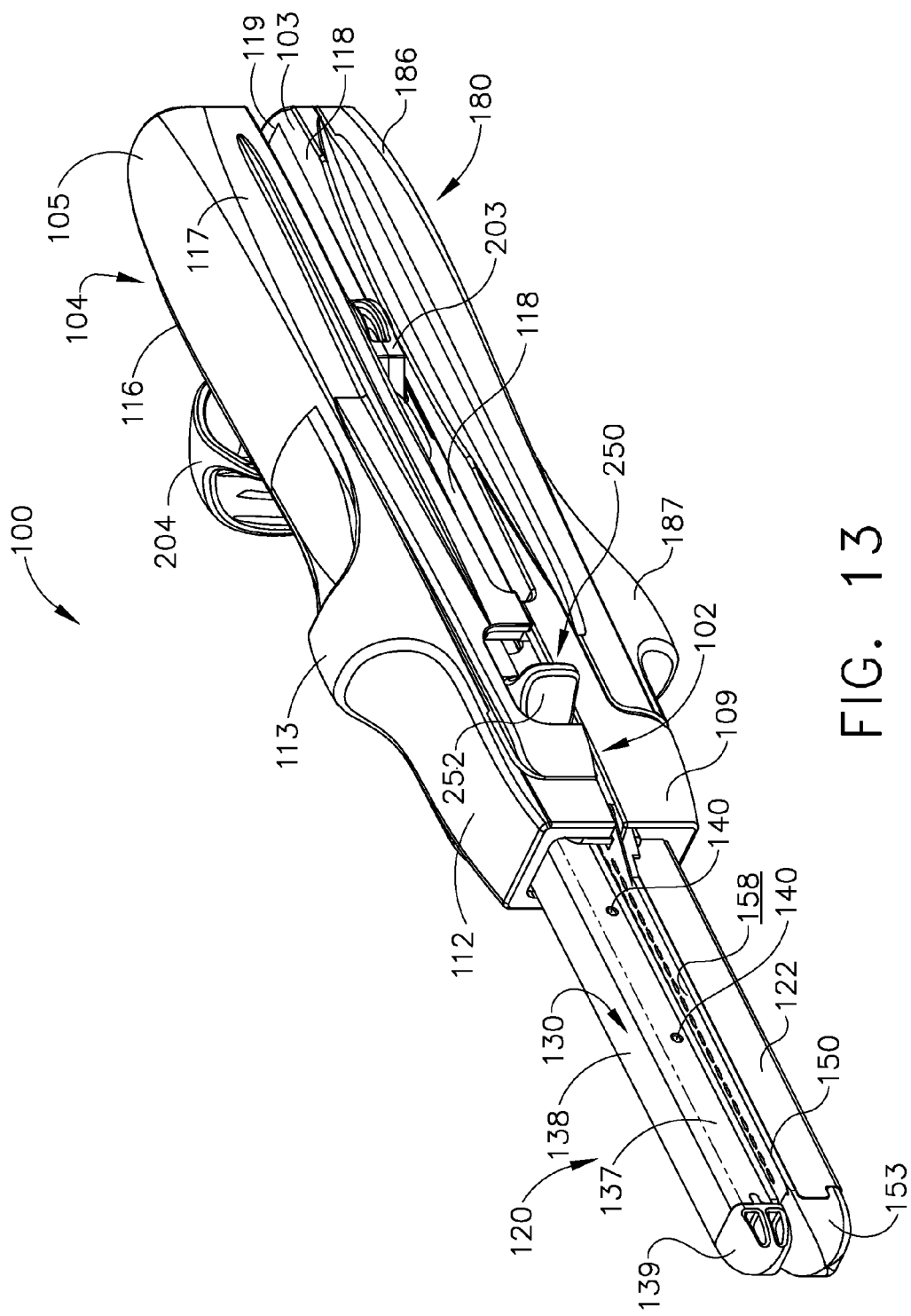
FIG. 13 is a perspective view of the surgical stapling instrument of FIG. 1 illustrating a firing actuator moved distally along a first side of the surgical stapling instrument.
Figure 14:
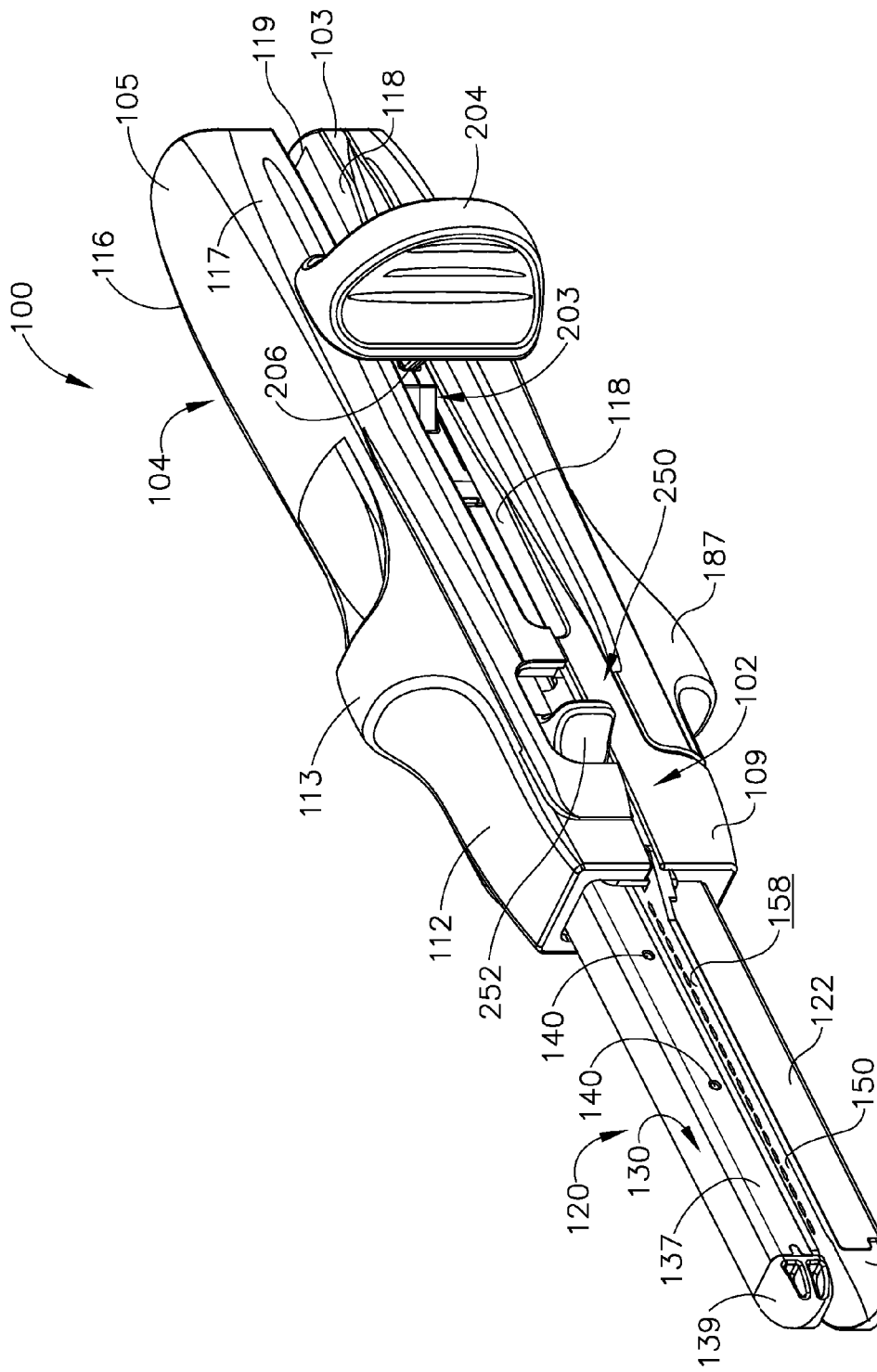
FIG. 14 is a perspective view of the surgical stapling instrument of FIG. 1 illustrating the firing actuator of FIG. 13 moved distally along a second side of the surgical stapling instrument.

Further to the above, referring to FIGS. 1, 13, and 14, actuator 204 can be movable between a first position on a first side 116 of surgical stapling instrument 100 (FIG. 13), a second position on a second side 117 (FIG. 14), and an intermediate position (FIG. 1) located at the proximal ends 103 and 105 of the first and second handle portions 102 and 104. Once actuator 204 has been rotated into position on one of the first and second sides 116, 117, actuator 204 can be advanced distally. In various circumstances, as a result, a surgeon may select whether to move actuator 204 distally along first side 116 or second side 117. Such circumstances may arise when it is more likely that actuator 204 may impinge on tissue surrounding the surgical site, for example, when actuator 204 is moved distally along one side of the surgical instrument as compared to the other. In various embodiments, referring to FIGS. 2 and 3, actuator 204 can include arm 206 extending therefrom where arm 206 can be pivotably mounted to proximal end 203 of pusher bar 202. In certain embodiments, referring once again to FIGS. 1, 13, and 14, surgical instrument 100 can include a first slot (not illustrated) extending along first side 116 and a second slot 118 extending along second side 117, wherein the first and second slots can be configured to slidably receive at least a portion of actuator 204. In at least one embodiment, the sidewalls of the first and second slots can confine, or at least assist in confining, the movement of actuator 204 such that it can be moved along a predetermined path. Referring to FIG. 14, second slot 118, for example, can be defined between first handle portion 102 and second handle portion 104 such that, when actuator 204 is moved distally along second side 117, arm 206 of actuator 204 can be slid intermediate the first and second handle portions. Similar to the above, the first slot can also be defined intermediate the first and second handle portions. In various embodiments, referring again to FIGS. 13 and 14, surgical instrument 100 can further include intermediate slot 119 which can also be configured to allow arm 206, and/or any other suitable portion of actuator 204, to slide therein. In at least one such embodiment, intermediate slot 119 can connect the first and second slots such that, when actuator 204 is positioned in its intermediate position, actuator 204 can be moved into either one of its first and second positions. In certain embodiments, the first slot, second slot 117, and intermediate slot 119 can be parallel, or at least substantially parallel, to one another and/or lie in the same plane, although other embodiments are envisioned in which one or more of the slots is not parallel to the others and/or lies in a different plane. Furthermore, although the first and second sides of the illustrated embodiment are located on opposite sides of surgical instrument 100, other embodiments are envisioned where the first and second slots, for example, are located on adjacent sides and/or sides which are not directly opposite to each other. Furthermore, other embodiments are envisioned in which the sides of a stapling instrument are not readily discernable, such as instruments having round and/or arcuate portions.

In various embodiments, further to the above, surgical stapling instrument 100 can further include a locking mechanism which can prevent, or at least inhibit, actuator 204 and, correspondingly, staple sled assembly 160, from being advanced prematurely. In at least one embodiment, the locking mechanism can be configured to prevent, or at least inhibit, actuator 204 from being advanced distally prior to latching mechanism 180 being moved into a closed, or an at least partially-closed, position. In certain embodiments, generally referring to FIG. 5, surgical stapling instrument 100 can further including locking mechanism 220 which can be engaged with actuator 204 and can remain engaged with actuator 204 while latching mechanism 180 is in a fully open position (FIG. 5) and/or an at least substantially-open position. In various embodiments, locking mechanism 220 can include lock 222 which can be biased into engagement with actuator 204 by a biasing force applied thereto by lock spring 224, for example. In at least one such embodiment, actuator 204 can include one or more grooves, channels, or slots (not illustrated) which can be configured to receive at least a portion of lock 222. In use, locking mechanism 220 can hold actuator 204 in position until latching mechanism 180 is moved into its fully closed position (FIG. 7) and/or an at least substantially closed position. In such circumstances, in at least one embodiment, latching mechanism 180 can be configured to engage locking mechanism 220 and disengage lock 222 from actuator 204. In at least one such embodiment, referring to FIGS. 5-7, latching mechanism 180 can further include cam 183 which can be configured to engage cam surface 223 on lock 222 when latching mechanism 180 is moved into its closed position and, as a result, slide, and/or otherwise move, lock 222 away from actuator 204. In various embodiments, cam 183 can comprise a wall, rib, and/or ridge extending from latch cover 186 and/or latch frame 184. In any event, once lock 222 has been sufficiently disengaged from actuator 204, in at least one embodiment, actuator 204 can be moved from its intermediate position, illustrated in FIG. 1, into one of its first and second positions, as illustrated in FIGS. 13 and 14.

Figure 15:
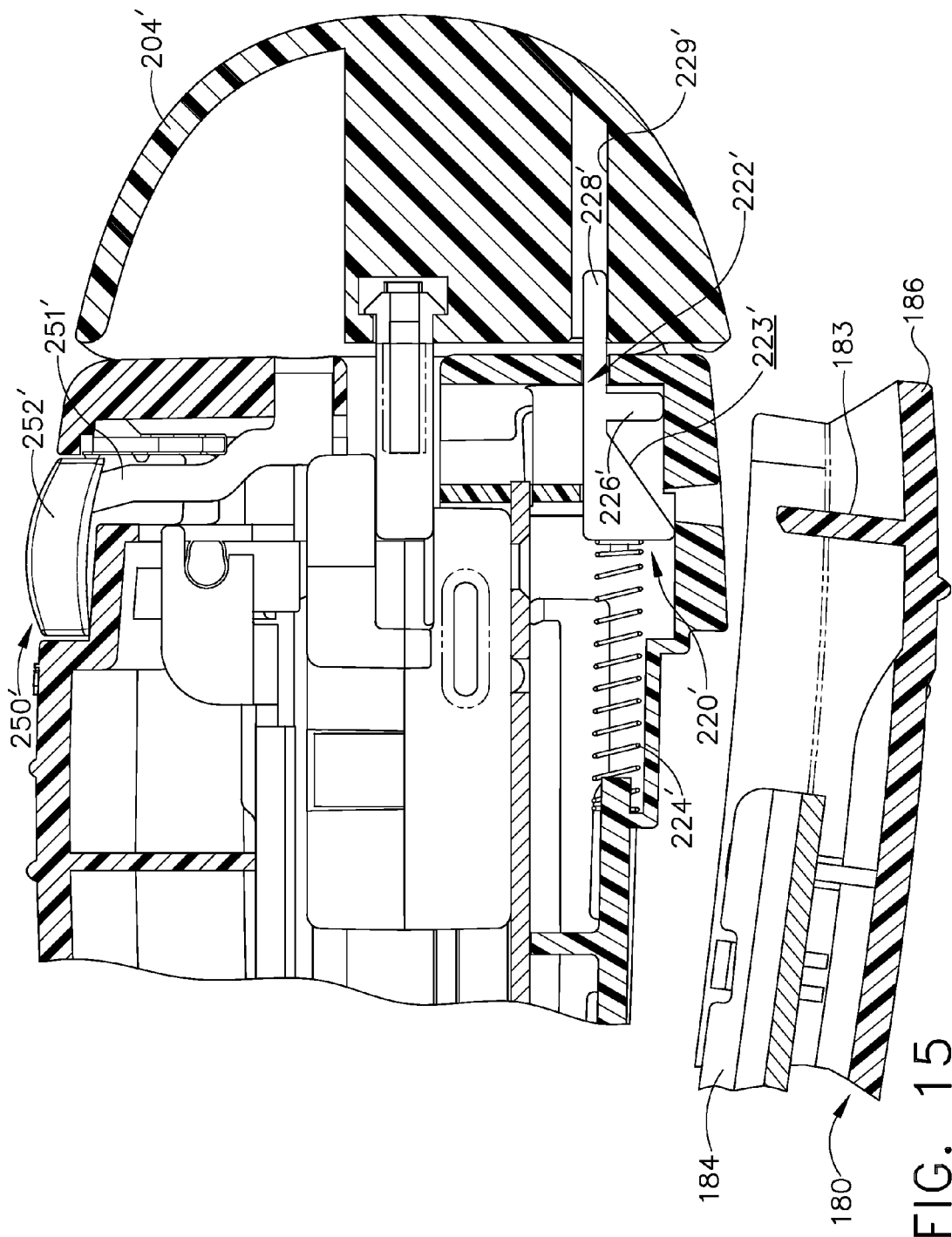
FIG. 15 is a cross-sectional view of a surgical stapling instrument in accordance with at least one alternative embodiment of the present invention illustrating a latch in a partially-closed position and a locking mechanism engaged with a firing actuator.
Figure 16:
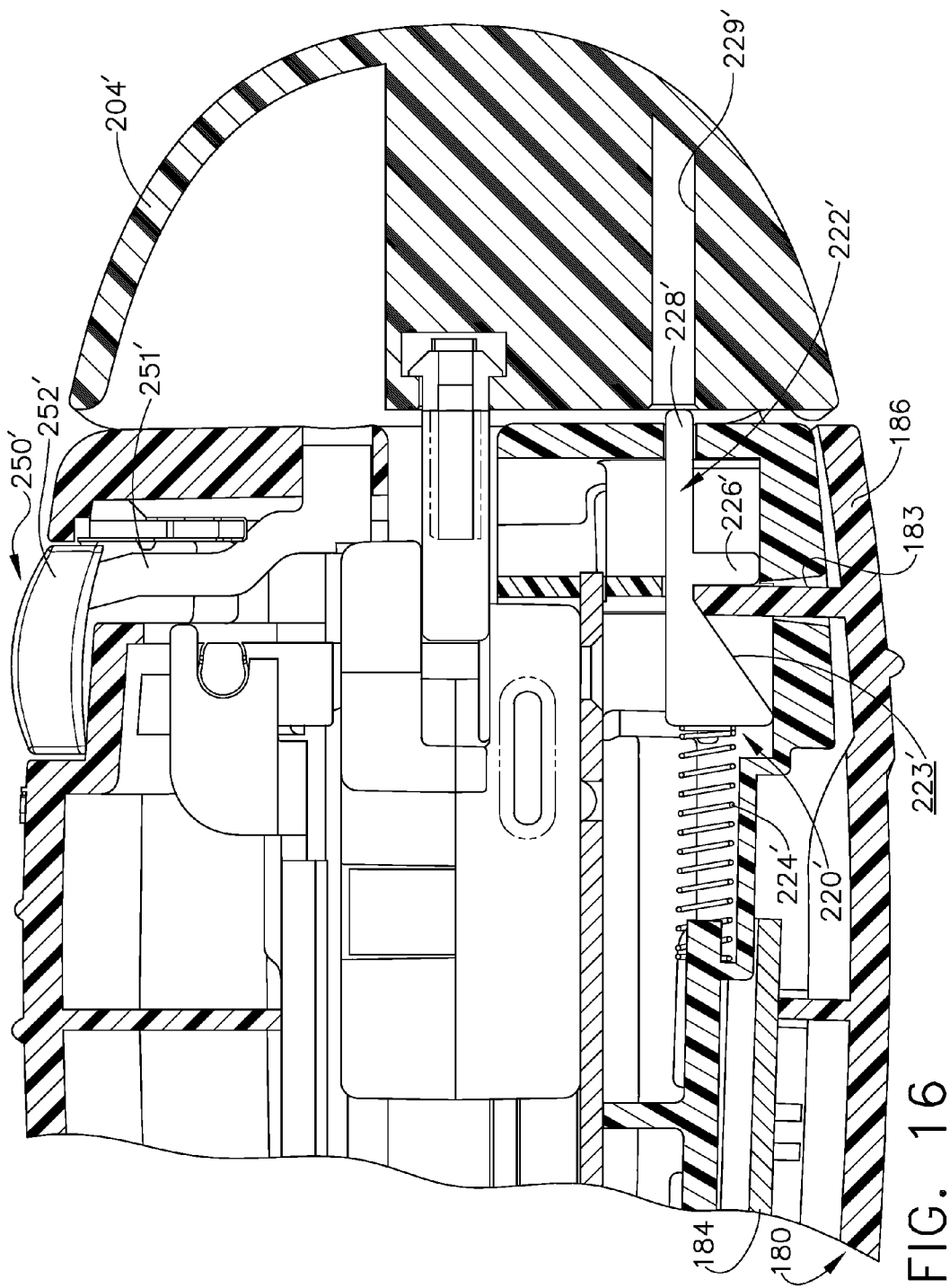
FIG. 16 is a cross-sectional view of the surgical stapling instrument of FIG. 15 wherein the latch has been moved into a closed position and has disengaged the locking mechanism from the firing actuator.

As described above, locking mechanism 220 can be configured to prevent, or at least inhibit, drive bar 202 from being advanced distally prior to latching mechanism 180 being moved into a predetermined position, such as, for example, a closed position and/or partially-closed position. Advantageously, locking mechanism 220 may also prevent, or at least inhibit, staple sled assembly 160 from being advanced prior to the first handle portion 102 and the second handle portion 104 being assembled together. In effect, locking mechanism 220 can prevent tissue positioned intermediate anvil 130 and staple cartridge 150 from being cut and/or stapled prior to anvil 130 and staple cartridge 150 being properly positioned relative to the tissue. Also, in effect, locking mechanism 220 can prevent staples from being deployed into the tissue prior to an appropriate clamping force being applied to the tissue. In any event, when latching mechanism 180 is returned to its fully open position, and/or a partially-open position, cam 183 can be moved away from lock 222 such that lock spring 124 can bias lock 222 into engagement with actuator 204 once again. In various other embodiments, referring to FIGS. 15 and 16, locking mechanism 220' can include a lock 222' comprising a cam surface 223' and, in addition, a stop 226' which can limit the relative movement of lock 222'. In at least one embodiment, cam 183, for example, can be configured to contact cam surface 223' and, owing to the contoured, beveled, and/or angled surface of cam surface 223', cam 183 can be configured to drive lock 222' distally as illustrated in FIG. 16. Lock 222' can be driven distally such that pin 228', which extends from lock 222', can be moved between a first position (FIG. 15) in which it is positioned within aperture 229' in actuator 204' and a second position (FIG. 16) in which pin 228' has been sufficiently removed from aperture 229'. In various embodiments, stop 226' can be configured such that, as lock 222' is driven distally, stop 226' can come into contact with cam 183 once lock 222' has been sufficiently displaced. In such embodiments, stop 226' can be configured to control the second, or displaced, position of lock 222'. Similar to the above, as actuator 180 is moved out of its closed position and cam 183 is disengaged from locking mechanism 220', lock spring 224' can move lock 222' into engagement with actuator 204' once again.

In various embodiments, as described above, a firing actuator can be utilized to move a pusher bar, staple sled, and/or cutting member between first and second positions. As also described above, pusher bar assembly 200, for example, can be utilized to move a staple sled assembly, such as staple sled assembly 160, for example, between a proximal position (FIG. 10) and a distal position. In certain embodiments, a staple cartridge, such as staple cartridge 150, for example, can include a staple sled assembly 160 contained therein, wherein staple sled assembly 160 can be positioned in a distal position, as illustrated in FIG. 10, when the staple cartridge is assembled to or inserted into staple cartridge channel 122. In at least one such embodiment, referring to FIGS. 8-10, staple cartridge 150 can include further housing 170 which can be configured to cover at least a portion of cutting member 164 when staple sled assembly 160 is in its distal position, for example. In various embodiments, housing 170 can be configured to protect a surgeon, for example, when handling the staple cartridge, when inserting the staple cartridge into the surgical stapler, and/or assembling two or more portions of the surgical stapler together, for example. In at least one such embodiment, at least an upper portion of cutting edge 165 can extend above deck, or top surface, 158 of staple cartridge 150 and, absent a protective housing, such as housing 170, for example, the upper portion of cutting edge 165 may be exposed.

In various embodiments, as described above, cutting member 165 can be at least partially positioned within slot, or channel, 156 and, as illustrated in FIG. 10, at least the upper, or top, portion of cutting member 164 can extend above deck 158. In at least one embodiment, referring to FIGS. 8-10, housing 170 can include a first wall, or portion, 172 extending from a first portion 157 of staple cartridge body 152, a second wall, or portion, 174 extending from a second portion 159 of staple cartridge body 152, and a top wall, or portion, 176 extending between first wall 172 and second wall 174. In certain embodiments, a housing may comprise only one support wall, or support portion, extending from a staple cartridge body and, in addition, a top wall, or top portion, extending therefrom. In other embodiments, a housing may comprise one or more side walls, or portions, and no top wall. In at least one such embodiment, the side walls of the housing can be configured such that they extend above the top of the cutting member, or at least extend above a cutting edge of the cutting member, for example. In any event, as illustrated in FIG. 10, at least a portion of cutting member 164 can be positioned underneath top wall 176 and/or between side walls 172 and 174 when staple sled assembly 160 is in its proximal position. In certain embodiments, cutting member 164 can be entirely positioned underneath top wall 176, and/or entirely positioned within housing 170. In at least one embodiment, cutting member 164 can be positioned underneath top wall 176 such that cutting surface 165 does not extend beyond the distal edge 175 and/or the proximal edge 177 of top wall 176. In at least one embodiment, housing 170 can include a rear wall 178 which can be configured to limit the proximal movement of cutting member 164 and/or any other portion of staple sled assembly 160. In various embodiments, at least a portion of housing 170, for example, can be integrally-formed with staple cartridge body 152. In at least one such embodiment, first wall 172, second wall 174, top wall 176, and/or rear wall 178 can be formed when staple cartridge body 152 is injection molded, for example. In certain embodiments, at least a portion of housing 170 can be assembled to staple cartridge body 152 via a snap-fit arrangement, press-fit arrangement, and/or any other suitable manner.

In various embodiments, further to the above, cutting member 164 can be defined by a planar, or an at least substantially planar, body having a knife edge extending along at least one side of the cutting member body. In at least one such embodiment, first wall 172 and/or second wall 174 can be configured and arranged such that they can include planar, or at least substantially planar, interior surfaces 173 which are parallel, or at least substantially parallel, to the side surfaces of cutting member 164. In certain embodiments, cutting member 164 can be closely received between the interior surfaces 173 of walls 172 and 174. In at least one such embodiment, the distance between walls 172 and 174 may be the same as, or at least substantially the same as, the width of slot 156. In any event, a housing can be configured such that at least a portion of the housing extends over at least a portion of slot 156, for example. In certain embodiments, housing 170 can completely enclose or surround a cutting member 164 and/or cutting surface 165. In at least one embodiment, although not illustrated, a housing can include a break-away and/or incisable portion which can be at least partially detached, separated, and/or otherwise deformed in order to permit a cutting member to exit the housing. In at least one such embodiment, the tissue cutting surface can be configured to contact the housing to break and/or incise a housing wall, for example. In various embodiments, the housing wall can include a thin portion, a reduced-thickness portion, score mark, and/or any other configuration to facilitate the deformation and/or incision of the housing wall. In certain embodiments, a cutting member can include one or more additional cutting surfaces and/or anvils, for example, which can be configured to deform and/or incise the housing. In at least one embodiment, the housing can include a movable and/or flexible portion, such as a hinged member and/or flexible flap, for example, which can be configured to sufficiently move and/or flex to allow the cutting member to pass thereby. In any event, embodiments are envisioned in which the cutting member can have any suitable configuration for incising tissue and the protective housing can have any suitable configuration for at least partially enclosing or surrounding the cutting member. Furthermore, although a cutting member can comprise a sharpened edge as described above, other suitable cutting members are envisioned, such as those supplied with an electrical current sufficient to dissect tissue, for example.

As described above, housing 170 can be configured to at least partially cover, enclose, and/or surround a cutting member when it is in its proximal position. In various embodiments, the cutting member can be advanced distally to incise tissue, for example, and then retracted proximally in order to position the cutting member within housing 170 once again. In such embodiments, the cutting member can be at least partially covered by housing 170 when the staple cartridge is assembled to and removed from a surgical stapling instrument. In certain embodiments, a new, or unspent, staple cartridge can be inserted into the staple cartridge channel to replace the at least partially spent staple cartridge. In at least one such embodiment, the new staple cartridge can include a new cutting member and/or staple sled assembly positioned therein, although embodiments are envisioned in which the previously-used cutting member and/or staple sled assembly can be sufficiently withdrawn from the spent staple cartridge and advanced into the new staple cartridge in order to be reused once again. In embodiments where a new cutting member and/or staple sled assembly is provided with each new staple cartridge, a sharp cutting edge, for example, can be utilized with each staple cartridge.

In various embodiments, although not illustrated, a staple cartridge can include two or more housings configured to at least partially cover a cutting member when it is in two or more positions. In at least one embodiment, a staple cartridge can include a proximal housing configured to at least partially cover the cutting member when it is in a proximal position, for example, and, in addition, a distal housing configured to at least partially cover the cutting member when it is in a distal position, for example. In at least one such embodiment, the cutting member can be positioned within the proximal housing when the staple cartridge is assembled to a surgical stapling instrument and, in certain embodiments, the cutting member can be advanced into the distal housing after it has transected tissue positioned within the end-effector, for example. In such embodiments, as a result, the cutting member can be at least partially positioned within the distal housing when the staple cartridge is removed from the surgical stapler. Such embodiments may be particularly useful when a vessel, for example, is positioned intermediate the proximal housing and the distal housing of the staple cartridge. In various embodiments, although not illustrated, a cutting member can be moved proximally from a distal position to a proximal position, and/or any other suitable position.

Figure 17:
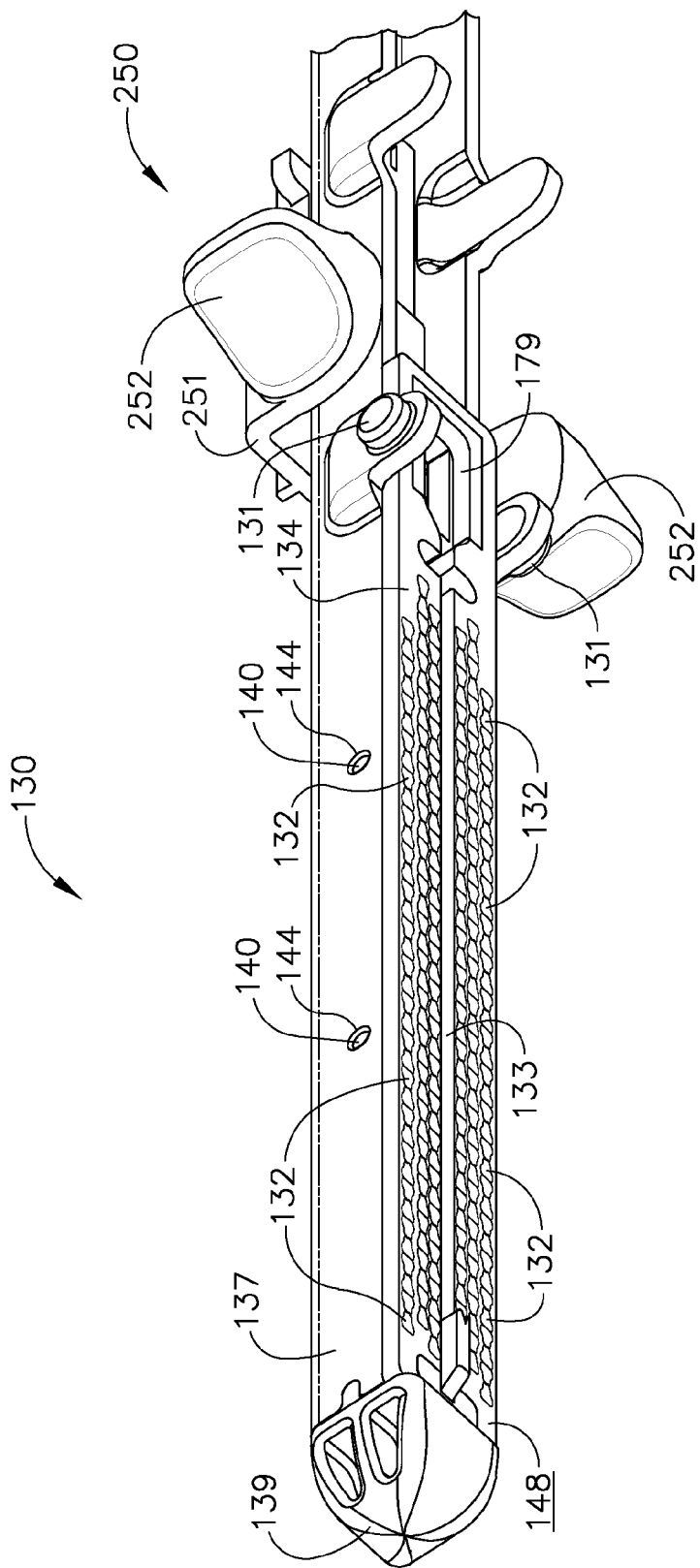
FIG. 17 is a perspective view of an anvil assembly of the surgical stapling instrument of FIG. 1.

In various embodiments, further to the above, anvil 130 can include one or more apertures, slots, or recesses 179 (FIG. 17) which can be configured to receive at least a portion of housing 170 when anvil 130 is brought into close opposition to staple cartridge 150, for example. In at least one embodiment, sufficient clearance can be present between housing 170 and recess 179 such that anvil 130 and staple cartridge 150 can be moved relative to each other without interference, or at least substantial interference, therebetween. In embodiments having more than one cutting member housing as outlined above, an opposing anvil can have more than one corresponding aperture for receiving the housings. In various embodiments, an anvil can include a movable cutting member and at least one housing for at least partially covering, enclosing, and/or surrounding the cutting member. In certain embodiments, although not illustrated, both an anvil and a staple cartridge can comprise at least one movable cutting member and/or at least one housing configured to at least partially cover, surround, or enclose the cutting members when they are in a proximal position, for example.

Figure 18:
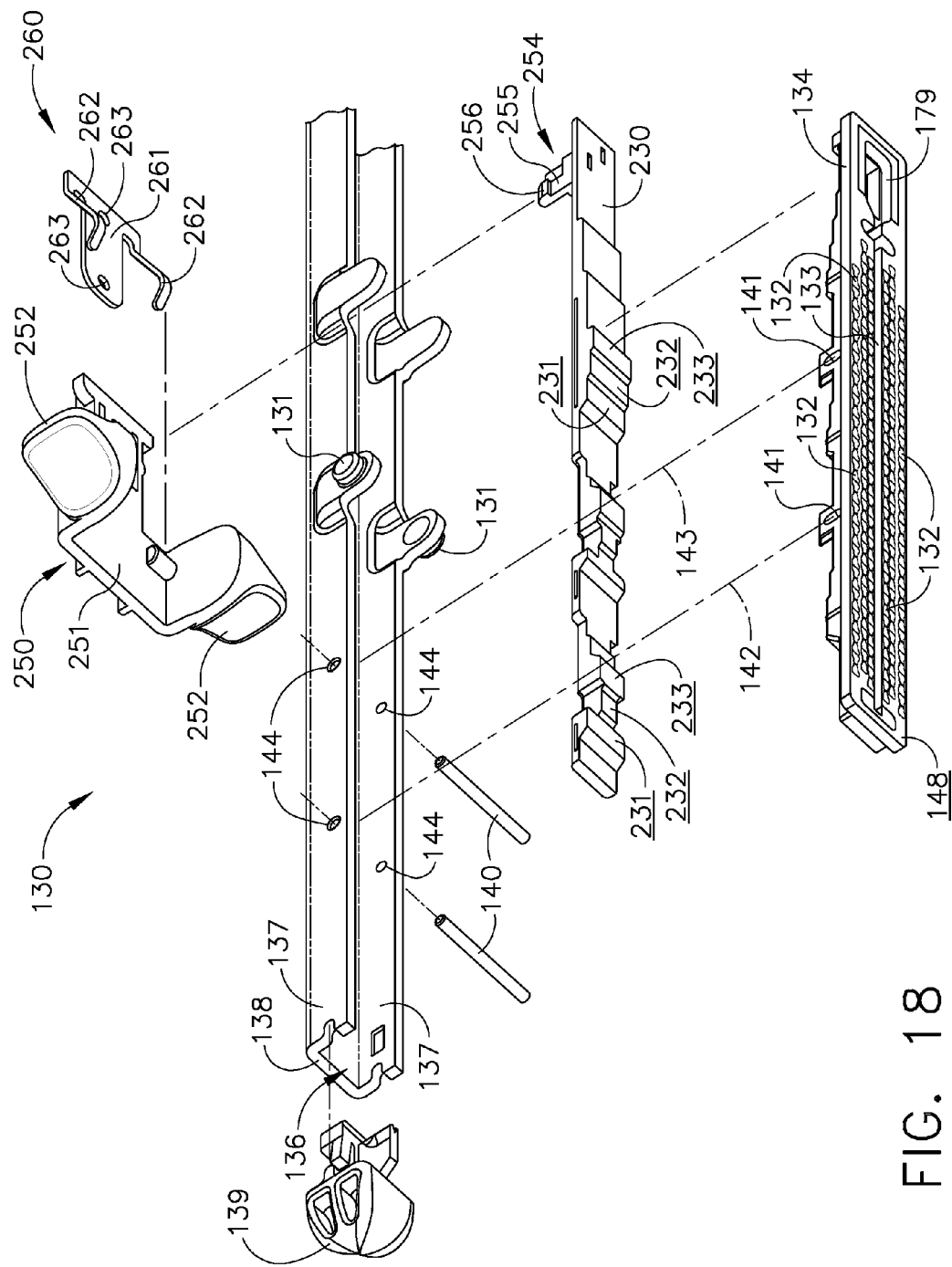
FIG. 18 is an exploded perspective view of the anvil assembly of FIG. 17.
Figure 19:
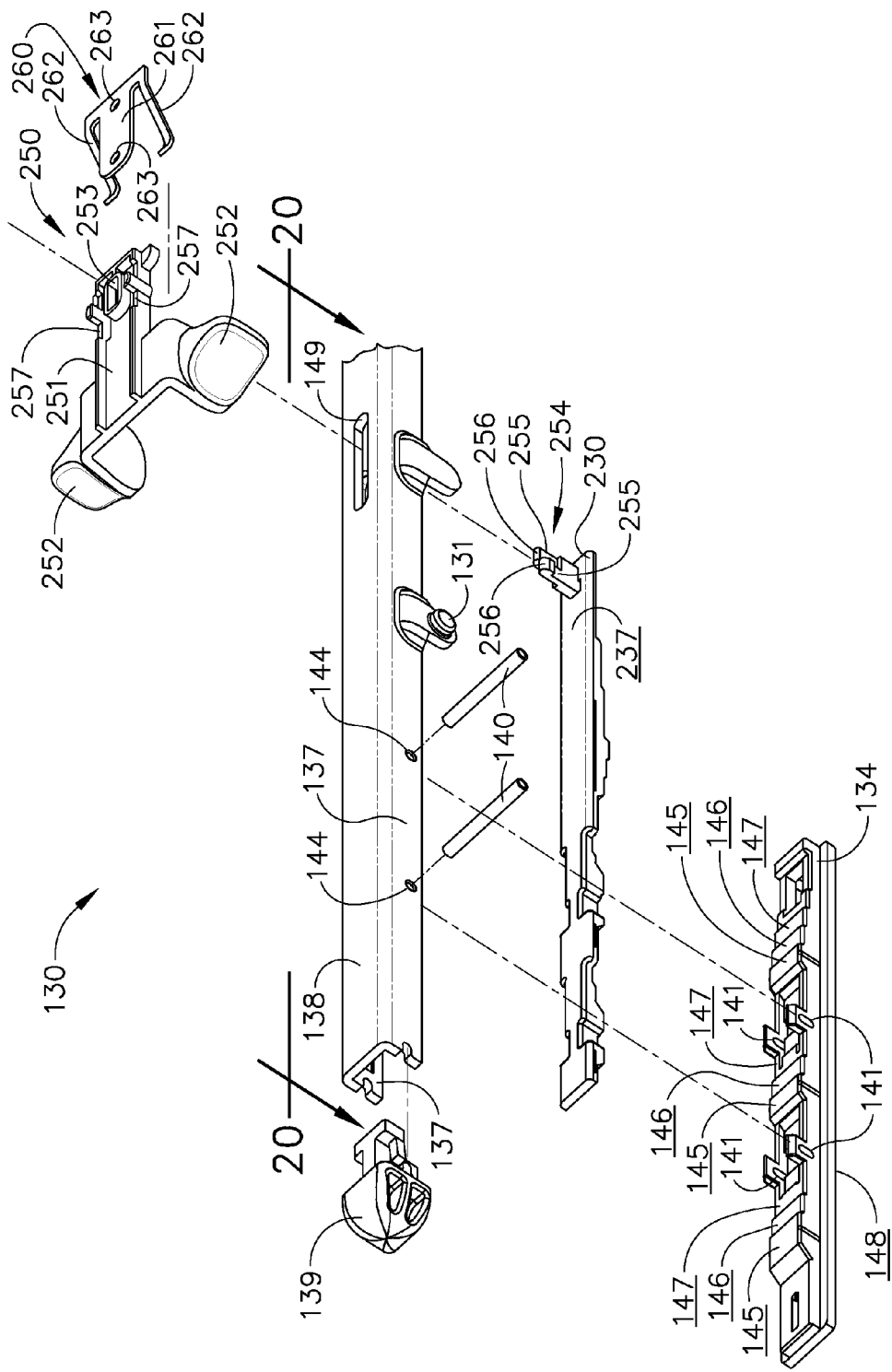
FIG. 19 is another exploded perspective view of the anvil assembly of FIG. 17.
Figure 24:
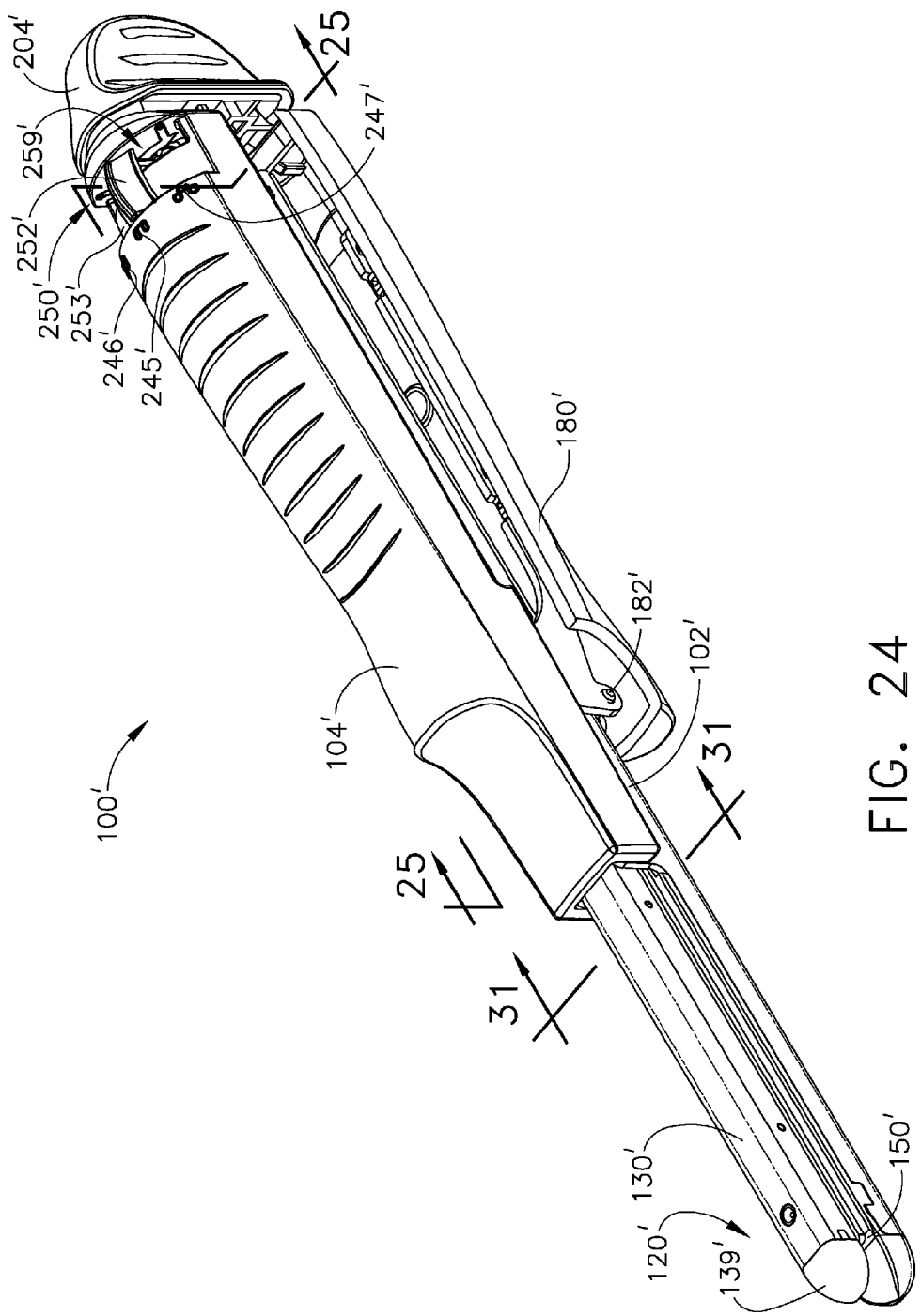
FIG. 24 is a perspective view of a surgical stapling instrument in accordance with at least one alternative embodiment of the present invention.
Figure 28:
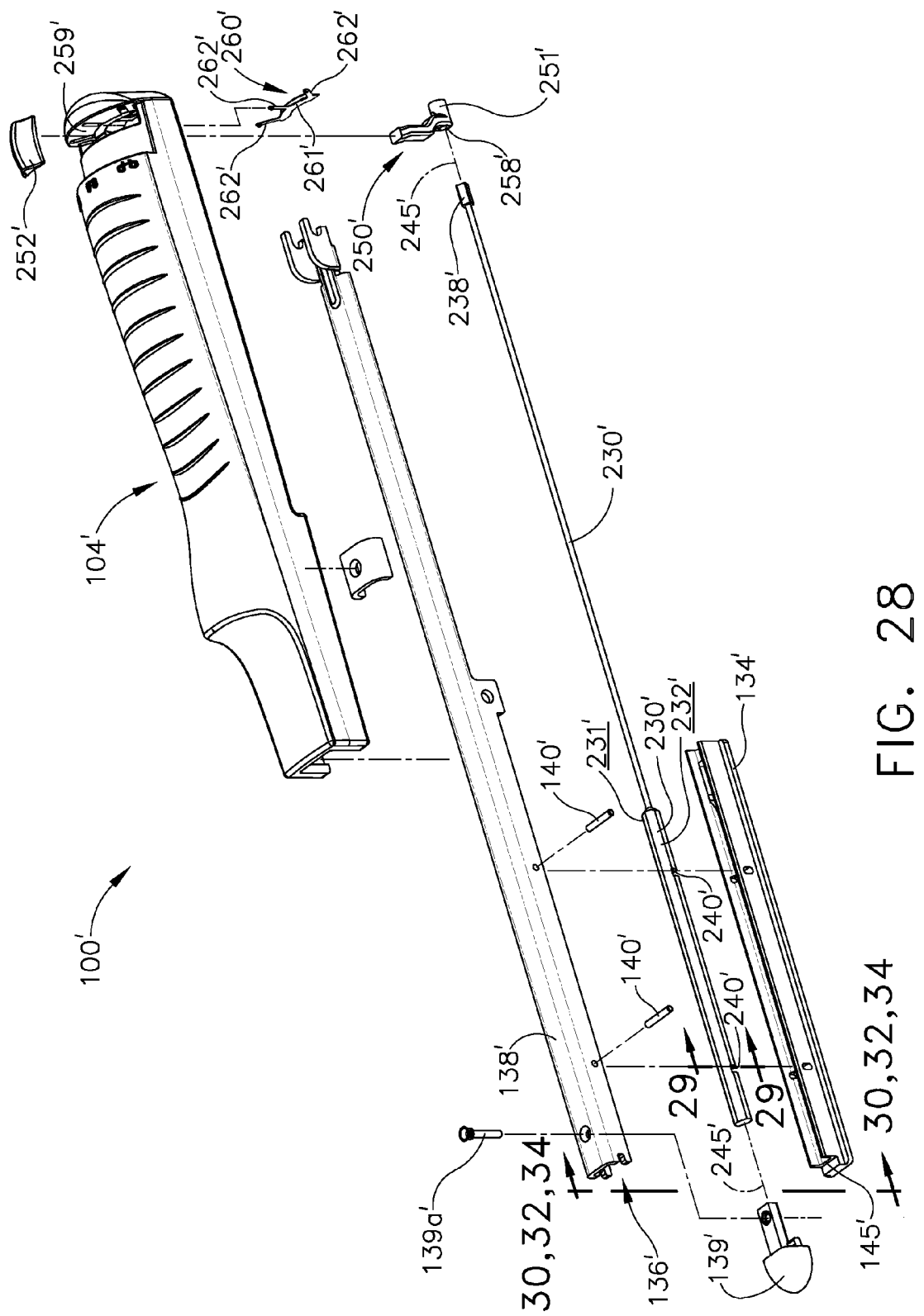
FIG. 28 is an exploded view of portions of the surgical stapling instrument of FIG. 24 illustrating a rotatable anvil adjustment member in a first orientation.
Figure 29:
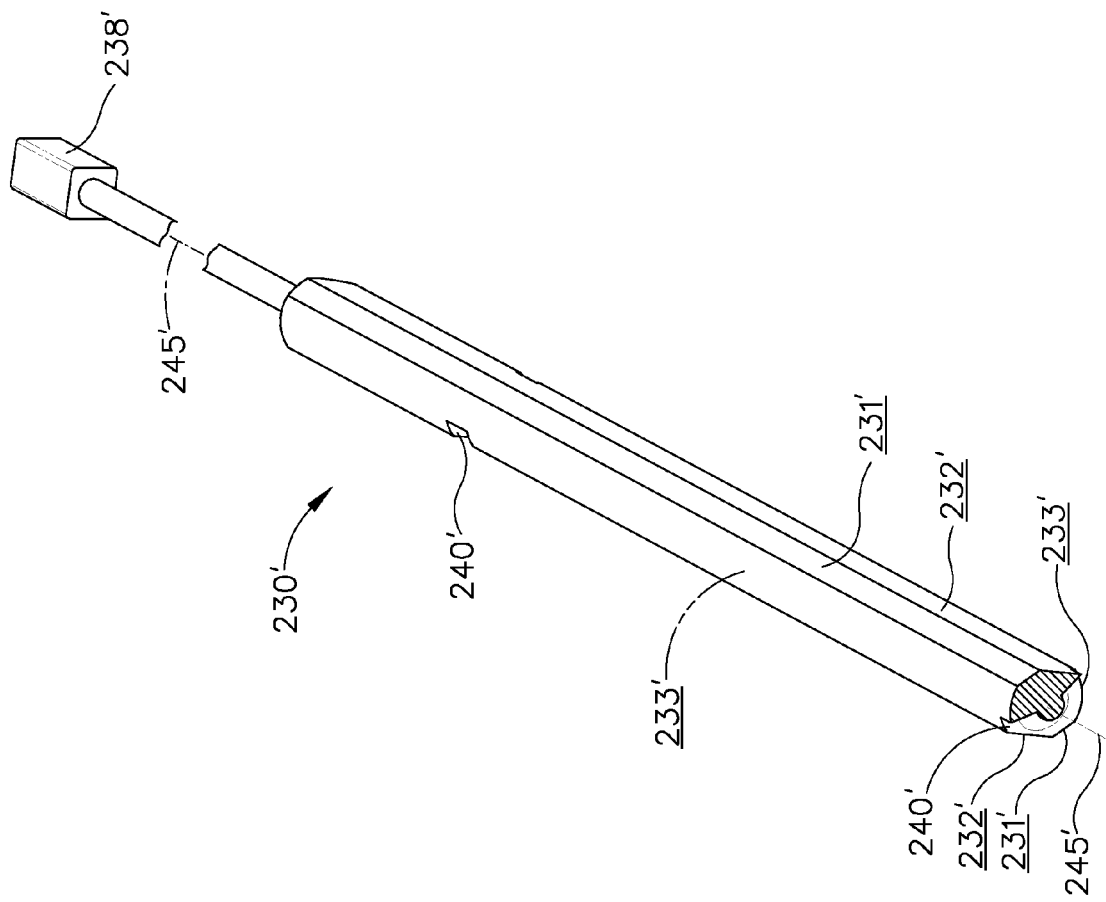
FIG. 29 is a perspective view of the rotatable anvil adjustment member of FIG. 28.
Figure 36:
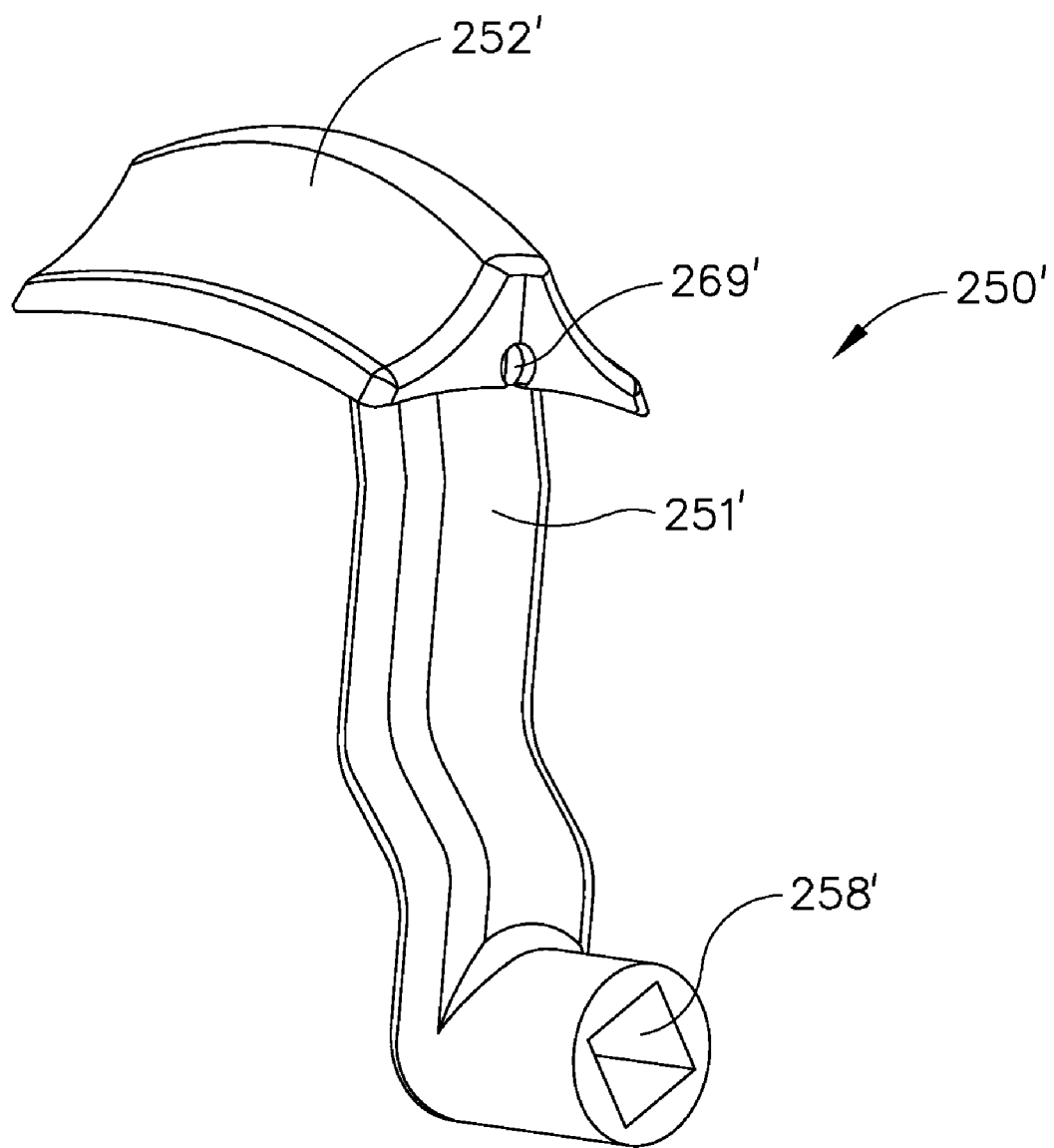
FIG. 36 is a perspective view of an actuator for rotating the anvil adjustment member of FIG. 28.

As outlined above, pusher bar assembly 200 can be advanced distally in order to move staple sled assembly 160 within staple cartridge assembly 150. In various embodiments, as also outlined above, the wedge-like cam surfaces 167 of staple sled 162 can be moved into engagement with the sloped surfaces 169 on staple drivers 168 to sequentially, and/or simultaneously, drive staples from staple cartridge 150 against anvil 130 and form the staples into any suitable configuration, such as B-shaped configurations, for example. In at least one such embodiment, referring to FIG. 17, anvil 130 can include one or more staple forming surfaces, such as staple pockets 132, for example, which can be configured to deform the staples. In certain embodiments, anvil 130 can further include a slot, channel, or groove 133 which can be configured to slidably receive at least a portion of staple sled 162, cutting member 164, and/or pusher bar 202, for example. In at least one embodiment, although not illustrated, an anvil can include an anvil plate which can be securely and/or immovably positioned within an anvil channel defined within the anvil. In various other embodiments, as illustrated in FIGS. 18 and 19 and described in greater detail below, anvil 130 can include an anvil plate 134 movably positioned within anvil channel 136. In certain embodiments, anvil channel 136 can include opposite side walls 137 and, in addition, a base 138 extending between side walls 137. In at least one embodiment, anvil 130 can further include a distal nose portion 139, for example, assembled thereto wherein nose portion 139 can be configured to be press-fit and/or snap-fit into anvil channel 136, for example, such that nose portion 139 can be securely retained therein. In certain embodiments, nose portion 139 can be comprised of a soft and/or pliable material, such as rubber, for example, and can comprise any suitable shape which can facilitate the insertion of anvil 130 into a surgical site, for example. In some embodiments, referring to FIG. 28, a nose portion, such as nose portion 139' can be retained to an anvil by one or more fasteners 139a'. Similarly, referring to FIG. 1, a staple cartridge channel and/or staple cartridge, such as staple cartridge 150, for example, can include a nose portion, such as nose portion 153, for example, which can facilitate the insertion of staple cartridge 150 into a surgical site, for example As indicated above, staples can be deployed from a staple cartridge and deformed against an anvil. In various circumstances, the distance between the staple forming surfaces on anvil 130 and staple sled 162 can determine the amount in which the staples are deformed. For example, if the distance between anvil pockets 132 on anvil 130 and top surfaces 135 on staple sled 162 (FIGS. 10-12) is relatively large, the staples will be deformed a lesser amount as compared to when the distance between anvil pockets 132 and sled surfaces 135 is relatively small. Correspondingly, if the distance between anvil pockets 132 and sled surfaces 135 is relatively small, the staples will be deformed a greater amount as compared to when the distance between anvil pockets 132 and sled surfaces 135 is relatively large. Often, the distance between anvil pockets 132 and sled surfaces 135 is referred to as the forming height of the staples. Sometimes the forming height of the staples can be measured between the top surface, or deck, of the staple cartridge and the staple forming surfaces on the anvil. For the purpose of this application, however, any reference to a staple forming height, or the like, can include one or both manners of measurement, where appropriate, and/or any other suitable manner of measurement. In any event, as described in greater detail below, a surgical stapling instrument, such as stapling instrument 100, for example, can include means for adjusting the staple forming height.

In various embodiments, further to the above, an anvil can include one or more forming surfaces which can be moved toward and/or away from a staple cartridge in order to set the forming height of the staples. In at least one embodiment, referring to FIGS. 17-23, anvil 130 can include anvil plate 134 which can be movably and/or slidably positioned within anvil channel 136. In certain embodiments, anvil 130 can further include one or more retention, or guide, pins 140, wherein anvil plate 134 can include one or more retention, or guide, slots 141 configured to slidably receive at least a portion of pins 140. In at least one such embodiment, pins 140 and/or slots 141 can be configured to define a predetermined path along which anvil plate 134 can be moved. Referring to FIG. 18, pins 140 and slots 141 can be structured and arranged such that anvil plate 134 can be moved along a linear, or at least substantially linear, path, wherein the linear path can be at least partially defined by axes 142 and 143, for example. Other embodiments are envisioned in which an anvil plate can be moved along a non-linear path, such as a curved and/or curvi-linear path, for example. In certain embodiments, at least a portion of pins 140 can be retained within apertures 144 in side walls 137 wherein, in at least one embodiment, pins 140 can be press-fit within apertures 144. In any event, as described herein, pins 140 can guide anvil plate 134 as it is moved toward and/or away from staple cartridge 150, for example.

In various embodiments, further to the above, a surgical stapling instrument, such as stapling instrument 100, for example, can include one or more adjustment members configured to position a portion of an anvil, such as anvil plate 134, for example, relative to other portions of an anvil assembly and/or an opposing staple cartridge. In certain embodiments, referring to FIGS. 18 and 19, stapling instrument 100 can include anvil plate adjustment member 230 which can be configured to limit the range of motion of anvil plate 134. In at least one such embodiment, referring to FIGS. 20 and 21, adjusting member 230 can be positioned intermediate anvil plate 134 in a first position in which first surface, or step, 231 of adjusting member 230 is positioned intermediate base 138 of anvil channel 136 and first positioning surface 145 on anvil plate 134. In such a first position, first step 231 can define the amount of relative movement possible, or permitted, between anvil plate 134 and anvil channel 136. For example, when anvil 130 is clamped against tissue as described above, anvil plate 134 can contact the tissue and slide upwardly toward base 138 until first positioning surface 145 contacts first step 231. Once surface 145 and step 231 are in contact, adjusting member 230 can prevent, or at least inhibit, anvil plate 134 from moving further toward base 138. In at least one such embodiment, as a result, adjusting member 230 can act as a stop such that the distance between base 138 and tissue-contacting surface 148 on anvil plate 134 can be defined by a first distance 234. While base 138 is used as a reference datum in the present example, other portions of anvil 130 and/or an opposing staple cartridge, for example, could be used as reference datums. When adjusting member 230 is in its first position, as described above, second surface, or step, 232 of adjusting member 230 can be positioned intermediate base 138 and second positioning surface 146 on anvil plate 134, and, in addition, third surface, or step, 233 can be positioned intermediate base 138 and third positioning surface 147. Referring to FIG. 20, adjustment member 230 can include two or more sets of steps, 231, 232, and/or 233 and anvil plate 134 can include two or more sets of positioning surfaces 145, 146, and/or 147. While first step 231 and first positioning surface 145 are described above as being configured to control the position of anvil plate 134, the second and third steps (232, 233) of adjustment member 230 and the second and third positioning surfaces (146, 147) of anvil plate 134, respectively, can also be configured to control the position of anvil plate 134. For the sake of brevity, though, the present example will be described in reference to the first surface, or step 231, as being the surface which controls the position of anvil plate 134, although the reader will understand that the steps 232 and 233 can control the position of anvil plate 134 as well.

In certain embodiments, the first position of adjustment member 230 can provide for a relatively small, or short, staple forming height. In other embodiments, although not illustrated, the first position of an adjustment member can provide for an intermediate, a relatively large, and/or any other suitable staple forming height. In the event that the forming height associated with the first position of the adjustment member is suitable, a surgeon can proceed to use the surgical stapling instrument to staple and/or incise tissue as described above. In the event, however, that the staple forming height is unsuitable, a surgeon, or other clinician, can move adjustment member 230 such that adjustment member 230 can permit anvil plate 134 to slide upwardly a different distance when anvil plate 134 contacts tissue positioned intermediate anvil 130 and staple cartridge 150. In at least one such circumstance, the distance in which anvil plate 134 is permitted to slide upwardly can be larger, thereby providing a larger forming height for the staples. Correspondingly, in other circumstances, the adjustment member can be moved such that anvil plate 134 can slide upwardly a shorter distance when anvil plate 134 contacts the tissue, for example, thereby providing a shorter staple forming height. While the term "upward", and the like, can mean vertically upward, the term is not so limited; rather, "upward" can mean any direction which is toward the base of the anvil and/or away from a staple cartridge, for example. In any event, adjustment member 230 can be moved between its first position, illustrated in FIG. 21, and a second position, illustrated in FIG. 22, in order to increase the staple forming height. As indicated by arrow "P" in FIG. 22, adjustment member 230 can be slid proximally in order to move adjustment member 230 between its first and second positions, although embodiments are envisioned where an adjustment member can be slid distally and/or any other suitable direction in order to adjust adjustment member 230. Once adjustment member 230 has been moved into its second position, referring to FIG. 22, first surface, or step, 231 can be positioned intermediate base 138 and second positioning surface 146 of anvil plate 134. In such a second position, first step 231 can once again define the amount of relative movement permitted between anvil plate 134 and anvil channel 136. In at least one embodiment, similar to the above, adjusting member 230 can act as a stop such that the distance between base 138 and tissue-contacting surface 148 on anvil plate 134 can be defined by a second distance 235.

Further to the above, adjustment member 230 can be moved between its second position, illustrated in FIG. 22, and a third position, illustrated in FIG. 23, in order to once again increase the staple forming height. As indicated by arrow "P" in FIG. 23, adjustment member 230 can be slid proximally in order to move adjustment member 230 between its second and third positions. Once adjustment member 230 has been moved into its third position, referring to FIG. 23, first surface, or step, 231 can be positioned intermediate base 138 and third positioning surface 147. In such a third position, first step 231 can once again define the amount of relative movement between anvil plate 134 and anvil channel 136. In at least one embodiment, similar to the above, adjusting member 230 can act as a stop such that the distance between base 138 and tissue-contacting surface 148 on anvil plate 134 can be defined by a third distance 236. While adjustment member 230 can be selectively moved between three positions as described above to provide three different staple forming heights, other embodiments are envisioned which comprise an adjustment member which can be moved between more than three positions to provide more than three different staple forming heights. For example, an adjustment member can be movable between four positions in order to provide four staple forming heights. Further embodiments are envisioned which comprise an adjustment member which can be moved between two positions to provide two staple forming heights. Furthermore, while surfaces, or steps, 231, 232, and 233 of adjustment member 230 are arranged in a descending order, other arrangements are envisioned in which the surfaces, or steps, are arranged in an ascending order. Other arrangements are envisioned in which the surfaces, or steps, are not necessarily arranged in either an ascending or a descending order. Similarly, positioning surfaces 145, 146, and 147 of anvil plate 134 can be arranged in an ascending order, a descending order (FIG. 20), and/or any other suitable order. Furthermore, while adjustment member 230 can be slid along an axis, other embodiments are envisioned where an adjustment member can be moved along any suitable path such as curved and/or curvi-linear paths, for example.

As described above, referring to FIG. 21, adjustment member 230 can comprise three surfaces, or steps, 231, 232, and 233 while anvil plate 134 can comprise three corresponding adjustment surfaces 145, 146, and 147. When adjustment member 230 is in its first position, for example, first surface 231 can be positioned such that it abuts or is adjacent to first adjustment surface 145, second surface 232 can be positioned such that it abuts or is adjacent to second adjustment surface 146, and third surface 233 can be positioned such that it abuts or is adjacent to third adjustment surface 147. As adjustment member 230 is slid relative to anvil plate 134, as described above and referring to FIGS. 22 and 23, surfaces 231, 232, and 233 of adjustment member 230 can be sequentially indexed relative to surfaces 145, 146, and 147 of anvil plate 134. In at least one such embodiment, an adjustment member can have the same number of steps as the number of positioning surfaces on an anvil plate. Other embodiments are envisioned where an adjustment member has more steps than positioning surfaces on the anvil plate. In at least one such embodiment, an anvil plate can include one positioning surface wherein the steps of an adjustment member can be selectively utilized to limit the upward movement of the anvil plate, for example. In various embodiments, referring generally to adjustment member 230 and anvil plate 134, an anvil plate may include one positioning surface, such as positioning surface 145, for example, where steps 231, 232, and 233 of adjustment member 230, for example, can be selectively positioned intermediate base 138 and positioning surface 145. In such embodiments, first step 231 can have a first thickness or height which can stop, or limit, the upward movement of anvil plate 134 so as to define a first staple forming height, second step 232 can have a second thickness or height which can stop, or limit, the upward movement of anvil plate 134 so as to define a second staple forming height, and, in addition, third step 233 can have a third thickness or height which can stop, or limit, the upward movement of anvil plate 134 so as to define a third staple forming height. In at least one embodiment, the thickness or height of steps 231, 232, and/or 233 can be measured between a back surface 237 of adjustment member 230 and a surface on the steps (231, 232, 233) which will contact anvil plate 134. In various embodiments, the difference in height, or thickness, between first step 231 and second step 232 can be the same, or at least substantially the same, as the difference in height, or thickness, between second step 232 and third step 233. In at least one such embodiment, as a result, the step heights can increase at a linear rate, or an at least substantially linear rate. In alternative embodiments, the difference in height, or thickness, between the first and second steps can be different than the difference in height, or thickness, between the second and the third steps. In at least one such embodiment, the first, second, and third steps may not increase or decrease in height, or thickness, at a linear rate; rather, although not illustrated, the steps may increase or decrease in height, or thickness, in a non-linear and/or geometric rate.

As described above, an adjustment member, such as adjustment member 230, for example, can be movable between two or more positions. In various embodiments, a surgical stapling instrument can include an actuator configured to move the adjustment member. In at least one embodiment, referring to FIGS. 17-20, surgical stapling instrument 100 can include actuator 250 which can be operably attached to adjustment member 230 such that a force can be applied to actuator 250 and transmitted to adjustment member 230. In certain embodiments, actuator 250 can include grasping portions, or handles, 252 which can be configured to be grasped by a surgeon, for example, in order to advance or retract adjustment member 230 within anvil 130 as described above. In certain embodiments, grasping portions 252 can extend from actuator body 251, wherein actuator body 251 can include one or more apertures, slots, or cavities 253 which can be configured to receive at least a portion of adjustment member 230. In at least one such embodiment, referring to FIG. 19, adjustment member 230 can include lock 254 extending therefrom, wherein at least a portion of lock 254 can be received within aperture 253 so as to retain actuator body 251 to adjustment member 230. In various embodiments, lock 254 can include one or more resilient, or flexible, legs 255 which can be deflected when they are inserted into aperture 253 but resiliently return, or at least partially return, to their unflexed position after feet 256 of legs 255 are sufficiently pushed through aperture 253. In at least one such embodiment, feet 256 can prevent, or at least inhibit, actuator body 251 from being detached from adjustment member 230.

In various embodiments, further to the above, surgical stapling instrument 100 can further include a detent mechanism which can be configured to hold, or releasably hold, actuator 250 and/or adjustment member 230 in position. In at least one embodiment, referring to FIG. 19, detent member 260 can be attached to actuator 250 wherein, in at least some embodiments, actuator body 251 can include one or more channels, grooves, or recesses 257 which can be configured to receive and/or retain a detent body 261 of detent member 260 therein. In at least one embodiment, detent body 261 can include one or more apertures 263, and/or any other suitable channels, slots, or grooves, which can be configured to receive one or more fasteners for securing detent body 261 to actuator 251, for example. Detent member 260 can further include detent legs 262 which can be configured to engage one or more recesses, apertures, or grooves 101 (FIGS. 2-7) in a first frame portion 110, for example. More particularly, referring to FIGS. 2 and 3, each side flange 128 can include one or more recesses 101 (101a, 101b, and 101c) defined therein wherein detent legs 262 can be biased into engagement with the top surfaces of side flanges 128 such that detent legs 262 can be slid into, and slid out of, recesses 101. In the illustrated embodiment, each side flange can include three recesses 101 which can be configured to removably hold actuator 250 in a first, distal position, a second, intermediate position, and a third, proximal position, wherein the first, second, and third positions of actuator 250 can respectively correspond with the first, second, and third positions of adjustment member 230 described above. For example, when actuator 250 is in its first, distal position, detent legs 262 of detent member 260 can be positioned within recess 101a so as to removably retain actuator 250 and adjustment member 230 in their first positions. Upon the application of a sufficient force, actuator 250 can be moved proximally into its second position such that detent legs 162 are positioned within recess 101b and actuator 250 and adjustment member 230 are retained in their second positions. Similarly, upon the application of a sufficient force, actuator 250 can be moved proximally into its third position such that detent legs 162 are positioned within recess 101c and actuator 250 and adjustment member 230 are retained in their third positions. In various embodiments, detent legs 162 can be configured such that actuator 250 can be returned to its first and/or second positions.

As described above, adjustment member 230 can be moved along a pre-determined path between two or more positions by actuator 250. In various embodiments, surgical stapling instrument 100, for example, can include one or more guides for controlling or limiting the movement of adjustment member 230 and/or actuator 250. In some embodiments, adjustment member 230 can be closely received between side walls 137 of anvil 130 such that side walls 137 can guide adjustment member 230. In at least one such embodiment, side walls 137 can be configured to control or limit the lateral or side-to-side movement of adjustment member 230. In various embodiments, detent legs 162 of detent member 160 can comprise resilient members which can be configured to apply an upward biasing or pulling force on adjustment member 230 so as to position adjustment member 230 against, or at least adjacent to, base 138 and intermediate side walls 137. In certain embodiments, referring to FIG. 19, base 138 of anvil 130 can further include guide slot 149 which can be configured to receive at least a portion of adjustment member 230 and/or actuator 250 therein such that guide slot 149 can limit the movement of adjustment member 230 and actuator 250. In at least one such embodiment, lock 254 of adjustment member 230 can be configured to extend through guide slot 149 such that, when lock 254 is inserted into aperture 253 of actuator 250 as described above, base 138 of anvil 130 can be captured intermediate adjustment member 230 and actuator 250. In certain embodiments, guide slot 149 can be configured to limit the movement of lock 254 such that adjustment member 230 can be prevented, or at least inhibited, from being moved distally when adjustment member 230 is in its first, or distal-most, position and/or, similarly, prevented, or at least inhibited, from being moved proximally when adjustment member 230 is in its third, or proximal-most, position.

Figure 37:
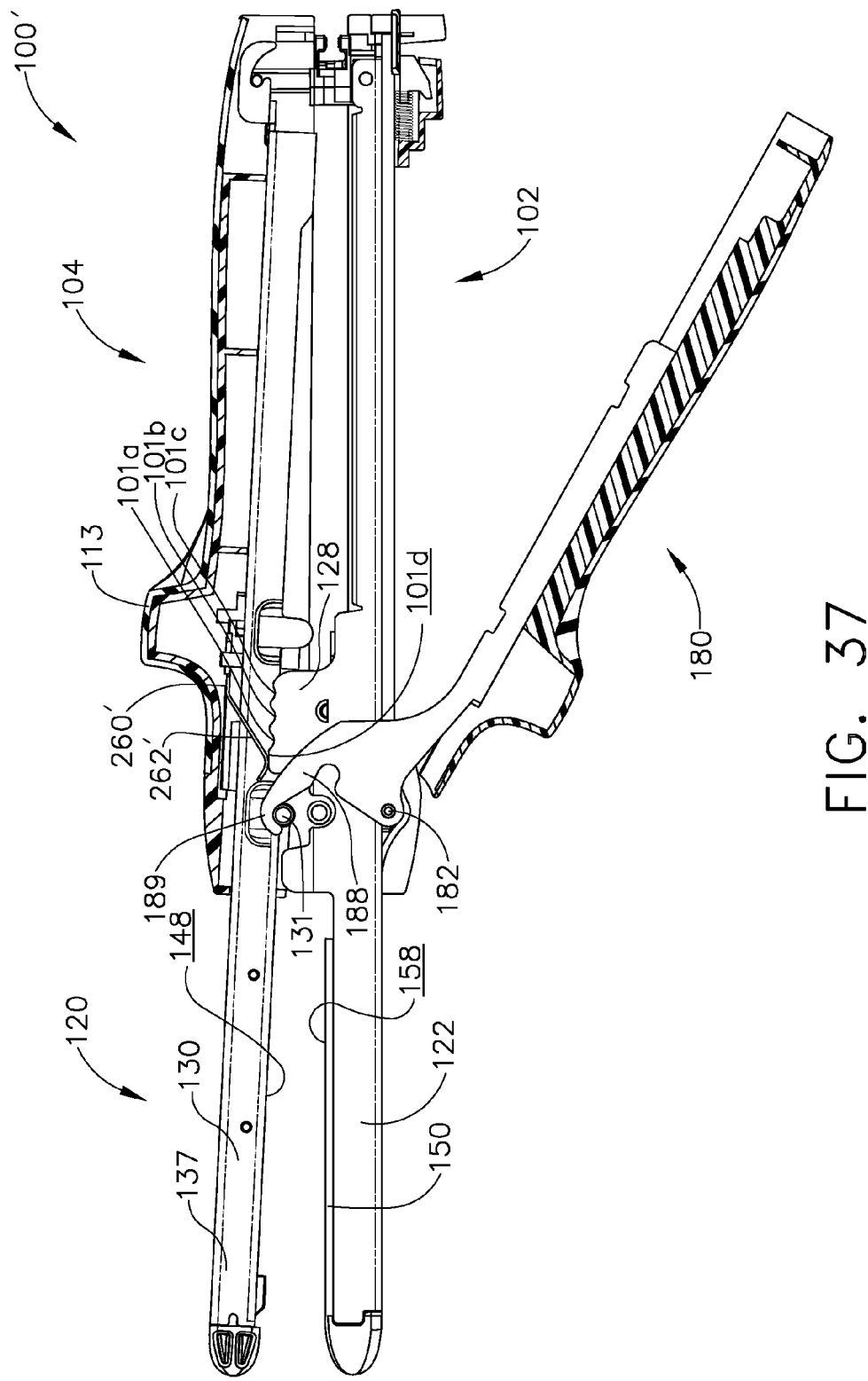
FIG. 37 is a partial cross-sectional view of a surgical stapling instrument including a spring configured to bias the distal end of a first handle portion away from the distal end of a second handle portion when the stapling instrument is in a partially-closed configuration.

In various embodiments, further to the above, a detent member, similar to detent member 260, for example, can be utilized to bias first handle portion 102 and second handle portion 104 away from one another. In at least one embodiment, referring to FIG. 37, surgical stapling instrument 100' can include a detent member 260' configured to position first handle portion 102 and second handle portion 104 such that a gap exists between anvil 130 and staple cartridge 150. Such a feature, as outlined above, can allow a surgeon to easily manipulate the surgical instrument without having to hold the first and second handle portions apart from one another. In certain embodiments, detent member 260' can be sufficiently mounted to second handle portion 104 such that detent legs 262' extending from detent member 260' can contact flanges 128 and, when compressed, apply a biasing force to the first and second handle portions. As seen in FIG. 37, legs 262' can contact surfaces 101d on flanges 128. In order to compress detent legs 262', latch mechanism 180 can be moved into a partially-closed position such that latch arms 188 can engage, and at least partially surround, latch projections 131. In this configuration, a surgeon can manipulate the instrument and, when satisfied with its position, move latch mechanism 180 into a closed position and further compress detent legs 262'. Similar to the above, detent member 260' can be affixed, or otherwise operably engaged with, actuator 250 such that, when actuator 250 is moved between its first, second, and third positions as described above, legs 262' can engage recesses 101a, 101b, and 101c, respectively. In at least one such embodiment, as a result, actuator 250 can have a pre-staged position in which actuator 250 is positioned distally with respect to its first position and, in addition, surfaces 101d can comprise pre-stage surfaces against which legs 262' can be positioned when actuator 250 is in its pre-staged position.

As outlined above, an adjustment member can be slid, or translated, between first and second positions so as to adjust the forming height of staples deployed by a surgical stapling instrument. In various embodiments, although not illustrated, an adjustment member can be configured to positively displace an anvil plate toward and/or away from an opposing staple cartridge, for example. In at least one such embodiment, a surgical stapling instrument can include one or more biasing members, such as springs, for example, configured to position the anvil plate against the adjustment member such that, when the adjustment member is moved between its first and second positions, the adjustment member can displace the anvil plate between first and second positions in order to set first and second staple forming heights. In various embodiments, as a result of the above, an adjustment member can be configured to cam a portion of an anvil into position. In at least one such embodiment, an adjustment member can be slid along an axis in order to positively displace an anvil plate. In other embodiments, a rotatable adjustment member can be configured to positively displace an anvil plate toward and/or away from a staple cartridge, for example.

Figure 25:
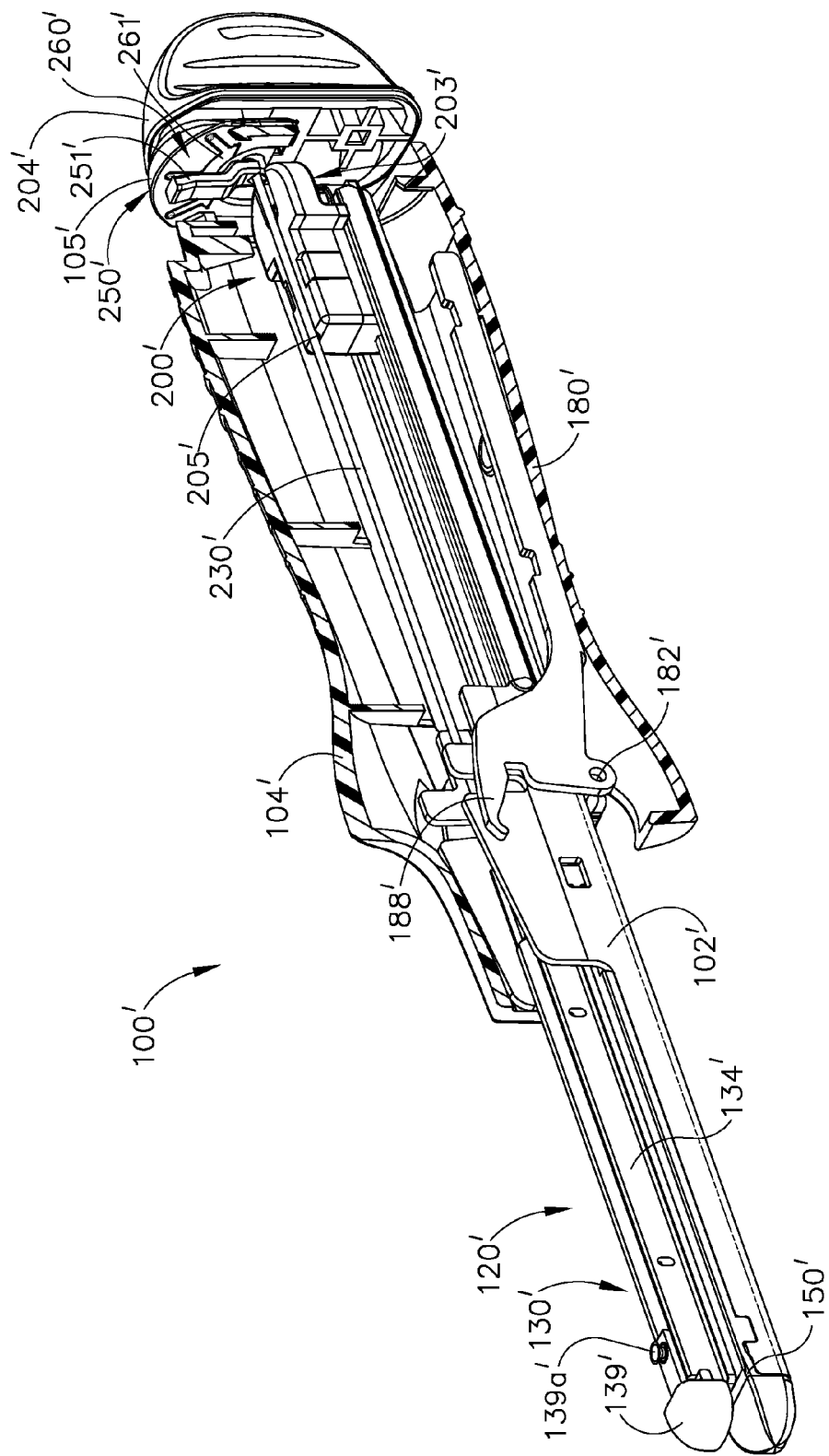
FIG. 25 is a cross-sectional view of the surgical stapling instrument of FIG. 24 taken along line 25-25 in FIG. 24.

Further to the above, as described in greater detail below, an adjustment member can be rotated to adjust the staple forming height. Referring to FIGS. 24-36, surgical instrument 100' can include, similar to the above, a first handle portion 102', a second handle portion 104', and a latching mechanism 180' which can be utilized to clamp tissue intermediate anvil 130' and staple cartridge 150'. Referring to FIG. 25, also similar to the above, latching mechanism 180' can be pivotably coupled to first portion 102' by one or more pivot pins 182', wherein latching mechanism 180' can include one or more latch arms 188' which can be configured to engage second portion 104' and latch the first and second handle portions together. Also similar to the above, referring to FIGS. 25 and 27, surgical instrument 100' can further include pusher bar assembly 200' which can be configured to advance a cutting member and/or staple sled within end-effector 120'. In at least one such embodiment, pusher bar assembly 200' can include a proximal end 203' and an actuator 204', wherein actuator 204' can be rotatably mounted to proximal end 203' and selectively positioned on first and second sides of stapling instrument 100'. In various embodiments, surgical stapling instrument 100' can comprise the same, or similar, features to those described in connection with surgical stapling instrument 100 and can be operated in the same manner, or a similar manner, as instrument 100 and, as a result, such details are not repeated herein.

Figure 27:
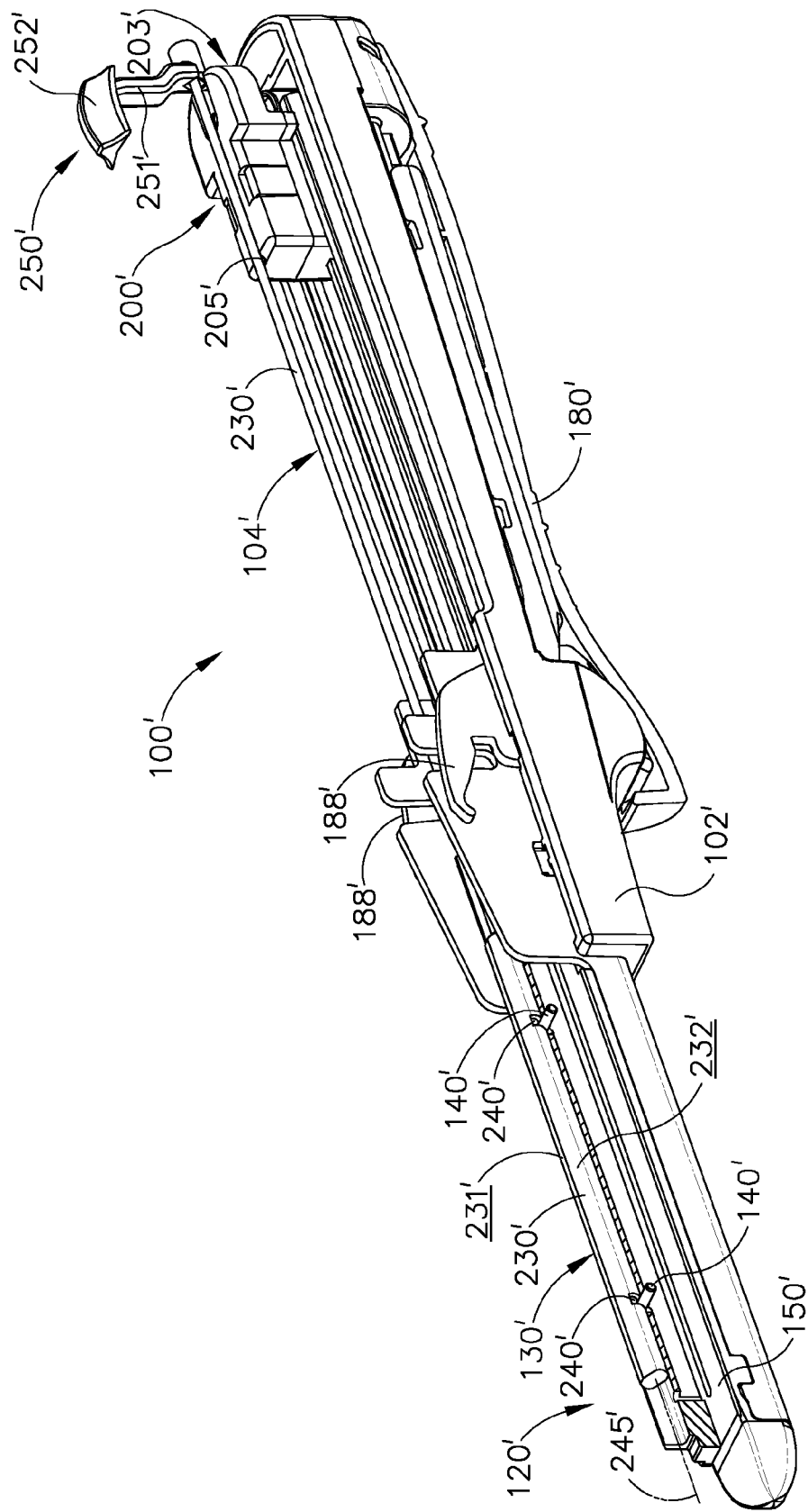
FIG. 27 is a perspective view of the surgical stapling instrument of FIG. 24 with some components removed and others shown in cross-section.

In various embodiments, referring to FIG. 27, surgical instrument 100' can include a rotatable adjustment member 230' which can be selectively positioned in at least first and second positions so as to provide different staple forming heights. In certain embodiments, surgical instrument 100' can include an actuator 250' which can be operably connected to adjustment member 230' such that actuator 250' can move adjustment member 230' between at least its first and second positions. In at least one embodiment, referring to FIG. 28, actuator 250' can include actuator body 251' and grasping portion, or handle, 252'. Actuator body 251' can include an aperture 258' which can be configured to receive a proximal end 238' of adjustment member 230' such that rotational motion, torque, and/or forces can be transmitted between actuator 250' and adjustment member 230'. In at least one such embodiment, referring to FIG. 36, aperture 258' can comprise a non-circular profile and/or a profile which includes one or more flat drive surfaces configured to transmit rotational motion between actuator body 251' and actuator 230'. In certain embodiments, aperture 258' can be sized and configured to closely receive proximal end 238' of actuator 230'. In at least one embodiment, aperture 258' can be configured to receive proximal end 238' in a press-fit and/or snap-fit arrangement. In various embodiments, referring again to FIG. 28, handle portion 104' can include one or more slots 259' which can be configured to permit at least a portion of actuator body 251' to extend therethrough such that grasping portion 252' can be assembled to actuator body 251' with at least a portion of handle portion 104' positioned therebetween. In at least one such embodiment, second handle portion 104' can further include recess 253' which can be configured such that at least a portion, if not all, of grasping portion 252' is positioned within recess 253'. In certain embodiments, recess 253' can be configured such that grasping portion 252' does not extend above the top surface of second handle portion 104' although, in other embodiments, an upper portion of grasping portion 252' can extend above second handle portion 104, as illustrated in FIG. 30, such that grasping portion 252' can be easily accessed by a surgeon.

In various embodiments, as outlined above, an adjustment member can be rotatable between at least first and second positions in order to adjust the forming height of staples deployed by a surgical stapler. In certain embodiments, referring to FIG. 28, a surgical stapling instrument can include an adjustment member rotatably positioned within an anvil wherein the adjustment member can be configured to limit the relative movement of a movable anvil portion. In at least one such embodiment, surgical stapling instrument 100' can include an anvil plate 134' which can be slidably retained within anvil channel 136' by retention, or guide, pins 140', wherein guide pins 140' can be configured to allow anvil plate 134' to slide upwardly when anvil plate 134' comes into contact with tissue as described above. Referring to FIGS. 27, 30, and 31, adjustment member 230' can be positionable in a first position, or orientation, such that it can limit the upward movement of anvil plate 134' within anvil channel 136' and dictate the staple forming height of the staples. In at least one such embodiment, referring to FIGS. 30 and 31, adjustment member 230' can include opposing first surfaces 231' which can be positioned intermediate base 138' of anvil channel 136' and positioning surface 145' of anvil plate 134' such that, when positioning surface 145' contacts one of first surfaces 231', tissue-contacting surface 148' of anvil plate 134' can be positioned a first distance 234' away from a datum surface 129' on anvil 130', for example. Correspondingly, forming surfaces 132' can be positioned a first distance away from a staple cartridge such that, when staples are deployed from the staple cartridge, the staples can be deformed to a first staple height. Further to the above, a first diameter 241' can be defined between first surfaces 231' wherein the first diameter 241' can define the maximum upward position of anvil plate 134' within anvil channel 136'.

As indicated above, adjustment member 230' can be rotated in order to adjust the forming height of the staples. In various embodiments, adjustment member 230' can be rotated between its first position, or orientation, (FIGS. 30 and 31) and a second position, or orientation (FIGS. 32 and 33). In at least one embodiment, referring to FIGS. 32 and 33, handle 252' can be rotated in a direction indicated by arrow "A" in order to move adjustment member 230' between its first and second positions. Similar to the above, when actuator 230' is in its second position, or orientation, actuator 230' can limit the upward movement of anvil plate 134' within anvil channel 136' and dictate the staple forming height of the staples. In at least one such embodiment, referring to FIGS. 32 and 33, adjustment member 230' can include opposing second surfaces 232' which can be positioned intermediate base 138' and positioning surface 145' such that, when positioning surface 145' contacts one of second surfaces 232', tissue-contacting surface 148' of anvil plate 134' can be positioned a second distance 235' away from datum surface 129', for example. Correspondingly, forming surfaces 132' can be positioned a second distance away from a staple cartridge such that, when staples are deployed from the staple cartridge, the staples can be deformed to a second staple height. In various embodiments, similar to the above, a second diameter 242' can be defined between second surfaces 232', wherein second diameter 242' can define the maximum upward position of anvil plate 134' within anvil channel 136'. Although first surfaces 231' and second surfaces 232' can be defined by flat, or at least substantially flat, surfaces, other embodiments are envisioned in which the first and second surfaces 231' and 232' can include at least partially arcuate, or curved, contours. In any event, referring to FIG. 27, adjustment member 230' may include one or more clearance slots 240' which can be configured to provide clearance between actuator 230' and retention pins 140'. Clearance slots 240' can be configured to provide clearance between actuator 230' and retention pins 140' when actuator 230' is in its first position, second position, and/or any other suitable position.

In various embodiments, further to the above, adjustment member 230' can be rotated between its first position, or orientation, (FIGS. 30 and 31) and a third position, or orientation (FIGS. 34 and 35). In at least one embodiment, referring to FIGS. 34 and 35, handle 252' can be rotated in a direction indicated by arrow "B" in order to move adjustment member 230' between its first and third positions. Similar to the above, when actuator 230' is in its third position, or orientation, actuator 230' can limit the upward movement of anvil plate 134' within anvil channel 136' and dictate the staple forming height of the staples. In at least one such embodiment, referring to FIGS. 34 and 35, adjustment member 230' can include opposing third surfaces 233' which can be positioned intermediate base 138' and positioning surface 145' such that, when positioning surface 145' contacts one of third surfaces 233', tissue-contacting surface 148' of anvil plate 134' can be positioned a third distance 236' away from datum surface 129', for example. Correspondingly, forming surfaces 132' can be positioned a third distance away from a staple cartridge such that, when staples are deployed from the staple cartridge, the staples can be deformed to a third staple height. In various embodiments, similar to the above, a third diameter 243' can be defined between third surfaces 233', wherein third diameter 243' can define the maximum upward position of anvil plate 134' within anvil channel 136'. Referring once again to FIGS. 34 and 35, third surfaces 233' can be defined by an at least partially arcuate contour, although other embodiments are envisioned in which third surfaces 233' can include flat, or at least substantially flat, contours. In at least one embodiment, adjustment member 230' can be configured such that the largest distance, or diameter, between the arcuate third surfaces 233' can be utilized to define the third staple height.

As described above, referring to FIGS. 30 and 31, adjustment member 230' can be positioned in a first position, or orientation, to set a first forming height for the staples deployed by surgical stapling instrument 100'. As also described above, referring to FIGS. 32 and 33, actuator 250' can be utilized to move adjustment member 230' into its second position, or orientation, to set a second forming height for the staples. To do this, in at least one embodiment, a force can be applied to handle 252' which can cause handle 252', and adjustment member 230' attached thereto, to rotate in a direction indicated by arrow "A". In at least one embodiment, adjustment member 230' and/or actuator 250' can be sufficiently retained such that, when adjustment member 230' is rotated, adjustment member 230' can be rotated about an axis, such as axis 245' (FIG. 27), for example. In at least one embodiment, referring to FIG. 25, the proximal end 203' of pusher bar assembly 200' can include one or more grooves, channels, or recesses 205' which can be configured to receive and/or retain at least a portion of adjustment member 230' and/or actuator 250' therein. In any event, as illustrated in FIGS. 30-33, the second position, or orientation, of adjustment member 230' can allow anvil plate 134' to slide a larger distance within anvil channel 136' as compared to when adjustment member 230' is in its first position. In at least one embodiment, as a result, the second staple forming height can be larger than the first staple forming height. As also described above, referring to FIGS. 34 and 35, actuator 250' can be utilized to move adjustment member 230' into its third position, or orientation, to set a third forming height for the staples. To do this, in at least one embodiment, a force can be applied to handle 252' which can cause handle 252', and adjustment member 230' attached thereto, to rotate in a direction indicated by arrow "B". As illustrated in FIGS. 30, 31, 34, and 35, the third position, or orientation, of adjustment member 230' can allow anvil plate 134' to slide a smaller distance within anvil channel 136' as compared to when adjustment member 230' is in its first position. In at least one embodiment, as a result, the first and second staple forming heights can be larger than the third staple forming height. In at least one such embodiment, the first position of adjustment member 230', and actuator 250', can represent an intermediate position, wherein adjustment member 230' can be selectively moved into its second and third positions directly from its first position. In effect, the first position of adjustment member 230' can represent an intermediate staple height, wherein the second and third staple positions of adjustment member 230' can represent taller and shorter staple heights, respectively. In certain embodiments, referring to FIG. 24, surgical stapling instrument 100' can include one or more indicia thereon which can be configured to convey the staple forming heights, or at least relative forming heights, that can be selected. For example, second handle portion 104' can include a first indicium 245' which can indicate an intermediate, or first, staple height, a second indicium 246' which can indicate a taller, or second, staple height, and, in addition, a third indicium 247' which can indicate a shorter, or third, staple height.

In various embodiments, further to the above, one or more of first surfaces 231', second surfaces 232', and third surfaces 233' can comprise or define, or at least partially comprise or define, a perimeter, or circumference, of adjustment member 230'. As discussed above, owing to the first, second, and third diameters (241', 242', and 243') defined by the first, second, and third surfaces (231', 232', and 233'), respectively, the perimeter, or circumference, of adjustment member 230' may be non-circular. In certain embodiments, though, the perimeter, or circumference of adjustment member 230', may be symmetrical, substantially symmetrical, and/or non-symmetrical. In various embodiments, further to the above, an adjustment member can comprise a cam rotatably positioned intermediate base 138' of anvil 130' and adjustment surface 145' of anvil plate 134', for example. In at least one such embodiment, one or more of first surfaces 231', second surfaces 232', and third surfaces 233', for example, can comprise or define a cam profile which, similar to the above, can be configured to either positively position anvil plate 134' and/or provide a stop against which anvil plate 134' can be positioned. In any event, although not illustrated, various embodiments are envisioned in which an adjustment member can be slid and rotated in order to set two or more staple forming heights for staples deployed by a surgical stapling instrument. In at least one such embodiment, an adjustment member can comprise a cam profile which can be defined along the length of the adjustment member wherein longitudinal and/or rotational movement can be utilized to move the cam profile between at least first and second positions.

Figure 26:
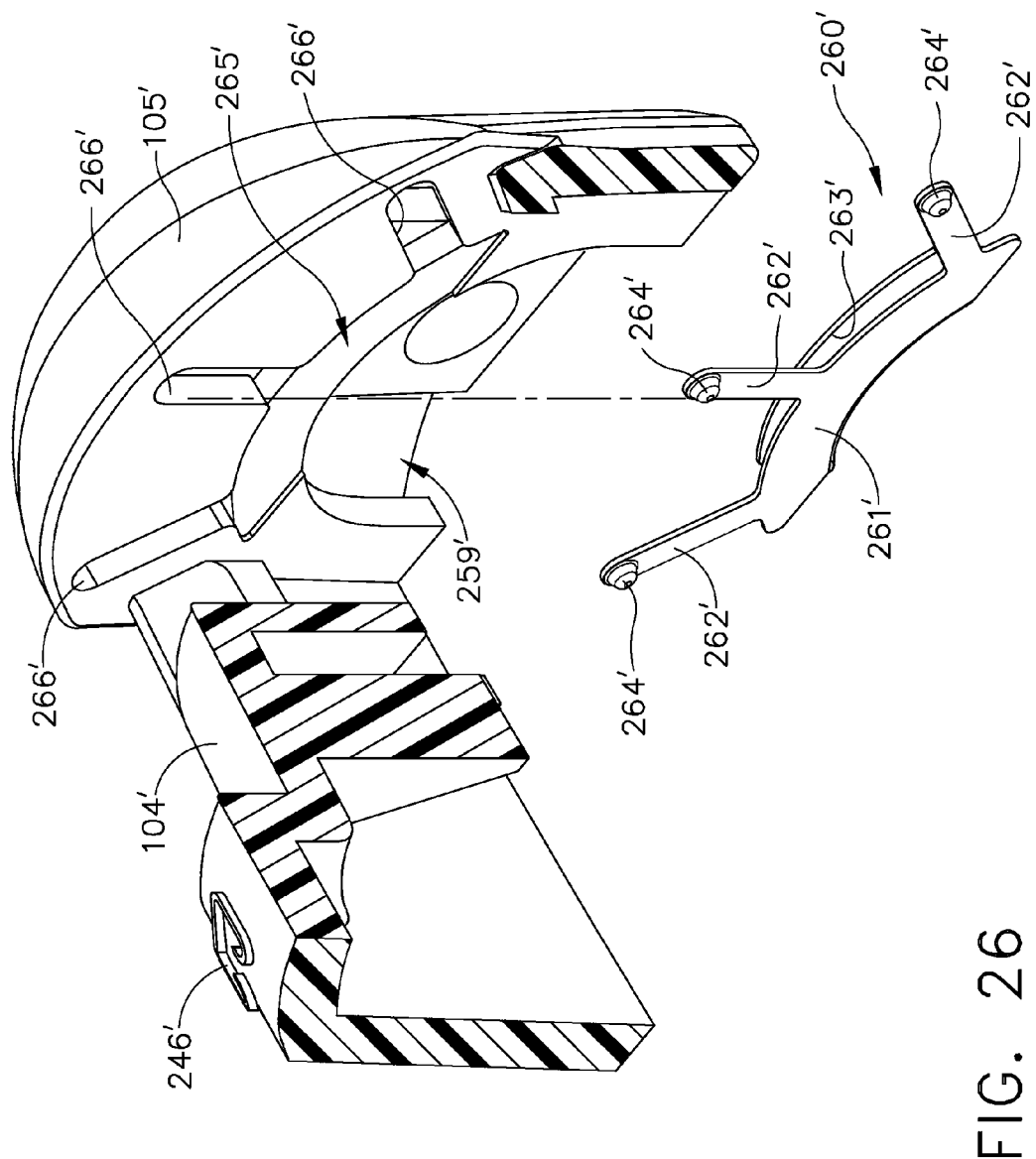
FIG. 26 is a partial exploded view of the proximal end of the surgical stapling instrument of FIG. 24 including a detent mechanism for releasably holding a rotatable anvil adjustment member in position.

In various embodiments, similar to the above, surgical instrument 100' can further include a detent mechanism configured to hold, or at least releasably hold, actuator 250' in position. In at least one embodiment, referring to FIGS. 25 and 26, surgical instrument 100' can further include detent member 260' comprising detent body 261' and one or more detent legs 262'. Referring to FIG. 26, detent body 261' can include one or more grooves, recesses, or channels 263' which can be configured to receive at least a portion of proximal end 105' of second handle portion 104' therein such that detent member 260' can be retained in position. In at least one such embodiment, proximal end 105' can further include one or more grooves, channels, or recesses 265' which can be configured to closely receive detent member 260'. In certain embodiments, at least a portion of detent body 261', such as channel 263', for example, can be press-fit, snap-fit, and/or otherwise suitably retained in recess 265'. As also illustrated in FIG. 26, each detent leg 262' of detent member 260' can include one or more projections 264' extending therefrom which can be configured to engage actuator body 251' and releasably hold actuator 250' in position. In at least one embodiment, referring to FIG. 36, actuator body 251' can include one or more recesses, or holes, 269' which can be configured to receive a projection 264'. When a projection 264' is positioned within recess 269', the projection can be configured to hold actuator 250' in its first position, for example, until a sufficient force is applied to actuator 250' so as to cause the projection 264' to be displaced out of recess 269'. More particularly, the force applied to actuator 250' can be transmitted to the projection 264' and, owing to cooperating surfaces between the projection 264' and recess 269', the detent leg 262' associated with the projection 264' can be flexed or moved proximally to allow actuator body 251' to be moved relative thereto. In order to accommodate such proximal movement, referring to FIG. 25, recess 265' can include elongate portions 266' which can each be configured to receive at least a portion of legs 262' such that legs 262' can move relative to handle portion 104'. As actuator 250' is moved into either its second or third position, actuator body 251' can contact a projection 264' extending from another leg 262' and deflect the leg 262' proximally such that, once actuator 250' is in its second or third positions, the leg 262' can spring forward, or distally, such that the projection 264' can be secured within recess 269'. In at least one embodiment, further to the above, the interaction between projections 264' and the sidewalls of recess 269' can be such that actuator 250' can be securely held in one of its first, second, and third positions, for example, yet permit actuator 250' to be moved upon a sufficient application of force. In such embodiments, the detent member 260' can prevent, or at least inhibit, actuator 250' and, correspondingly, adjustment member 230' from being unintentionally displaced.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical stapler, comprising:
  a first handle portion including a staple cartridge channel configured to receive a staple cartridge;
  a second handle portion including an anvil;
  a first drive slot;
  a second drive slot, wherein at least one of said first and second drive slots defines a predetermined path;
  a drive member;
  an actuator operably engaged with said drive member, wherein said actuator is selectively movable into said first drive slot and said second drive slot, and wherein said actuator is configured to move said drive member along said predetermined path;
  an actuator lock selectively engageable with said actuator; and
  a latch rotatably coupled to one of said first handle portion and said second handle portion, wherein said latch is movable between an open position and a closed position, wherein said latch is configured to engage the other of said first handle portion and said second handle portion and move said anvil into position relative to said staple cartridge channel, and wherein said latch is configured to engage said actuator lock when said latch is moved into said closed position to disengage said actuator lock from said actuator.

2. The surgical stapler of claim 1, wherein said actuator is positionable in an intermediate drive slot connecting said first drive slot and said second drive slot.

3. The surgical stapler of claim 2, wherein said actuator lock is configured to hold said actuator in said intermediate drive slot when said latch is in said open position.

4. The surgical stapler of claim 2, wherein said actuator is configured be selectively rotated into one of said first drive slot and said second drive slot when said actuator is positioned within said intermediate drive slot, and wherein said actuator lock is configured to prevent said actuator from rotating into either of said first drive slot and said second drive slot when said actuator lock is engaged with said actuator.

5. The surgical stapler of claim 1, wherein actuator lock is configured to hold said actuator in a position intermediate said first drive slot and said second drive slot when said latch is in said open position.

6. The surgical stapler of claim 1, further comprising a lock spring configured to bias said actuator lock into engagement with said actuator.

7. The surgical stapler of claim 1, wherein said drive member includes at least one of a cutting member and a staple sled.

8. A surgical stapler, comprising:
  a first handle portion including:
    a proximal end;
    a distal end; and
    a staple cartridge channel configured to receive a staple cartridge;
  a second handle portion including:
    a proximal end;
    a distal end; and
    an anvil;
  a drive member;
  an actuator operably engaged with said drive member, wherein said actuator is configured to move said drive member distally along a predetermined path;
  an actuator lock selectively engageable with said actuator; and
  a latch rotatably coupled to one of said first handle portion and said second handle portion, wherein said latch is configured to engage the other of said first handle portion and said second handle portion and bring said anvil into position relative to said staple cartridge channel when said latch is moved between an open position and a closed position, and wherein said latch is configured to engage said actuator lock when said latch is moved into said closed position and disengage said actuator lock from said actuator.

9. The surgical stapler of claim 8, further comprising a lock spring configured to bias said actuator lock into engagement with said actuator.

10. The surgical stapler of claim 8, further comprising a first drive slot and a second drive slot, wherein said actuator is selectively movable into said first drive slot and said second drive slot, wherein at least one of said first drive slot and said second drive slot defines said predetermined path, and wherein said actuator lock is configured to prevent said actuator from moving into either of said first drive slot and said second drive slot when said actuator lock is engaged with said actuator.

11. The surgical stapler of claim 8, further comprising a first drive slot and a second drive slot, wherein said actuator is selectively movable into said first drive slot and said second drive slot, wherein at least one of said first drive slot and said second drive slot defines said predetermined path, and wherein actuator lock is configured to hold said actuator in a position intermediate said first drive slot and said second drive slot when said latch is in said open position.

12. The surgical stapler of claim 8, wherein said drive member includes at least one of a cutting member and a staple sled.

13. A surgical stapler, comprising:
a first handle portion including a staple cartridge channel configured to receive a staple cartridge;
a second handle portion including an anvil;
a drive member;
an actuator operably engageable with said drive member, wherein said actuator is configured to move said drive member along a predetermined path;
an actuator lock biased into engagement with said actuator; and
a latch rotatably coupled to one of said first handle portion and said second handle portion, wherein said latch is rotatable between an open position and a closed position, wherein said latch is configured to engage the other of said first handle portion and said second handle portion and position said anvil relative to said staple cartridge channel when said latch is moved between said open position and said closed position, and wherein said latch is configured to disengage said actuator lock from said actuator when said latch is moved between said open position and said closed position.

14. The surgical stapler of claim 13, further comprising a lock spring configured to bias said actuator lock into engagement with said actuator.

15. The surgical stapler of claim 13, further comprising a first drive slot and a second drive slot, wherein said actuator is selectively movable into said first drive slot and said second drive slot, wherein at least one of said first drive slot and said second drive slot defines said predetermined path, and wherein said actuator lock is configured to prevent said actuator from moving into either of said first drive slot and said second drive slot when said actuator lock is engaged with said actuator.

16. The surgical stapler of claim 13, further comprising a first drive slot and a second drive slot, wherein said actuator is selectively movable into said first drive slot and said second drive slot, wherein at least one of said first drive slot and said second drive slot defines said predetermined path, and wherein actuator lock is configured to hold said actuator in a position intermediate said first drive slot and said second drive slot when said latch is in said open position.

17. The surgical stapler of claim 13, wherein said drive member includes at least one of a cutting member and a staple sled.

18. A surgical stapler, comprising:
a first handle portion including a staple cartridge attachment portion configured to have a staple cartridge attached thereto;
a second handle portion comprising an anvil;
a drive member configured to be moved along a predetermined path;
a lock selectively engageable with said drive member; and
a latch rotatably coupled to one of said first handle portion and said second handle portion, wherein said latch is movable between a first position and a second position, wherein said latch is configured to engage the other of said first handle portion and said second handle portion and move said anvil and said staple cartridge attachment portion into position relative to one another, and wherein said latch is configured to operably disengage said lock from said drive member when said latch is moved into said second position.

19. The surgical stapler of claim 18, further comprising said staple cartridge.

20. The surgical stapler of claim 18, wherein said latch further comprises a cam configured to engage said lock and move said lock away from said drive member.

21. The surgical stapler of claim 18, wherein said drive member further comprises an actuator, wherein said actuator is movable toward said staple cartridge attachment portion to move said drive member along said predetermined path, and wherein said lock is configured to engage said actuator.

22. The surgical stapler of claim 21, further comprising a first drive slot and a second drive slot, wherein said actuator is selectively movable into said first drive slot and said second drive slot in order to move said drive member along said predetermined path, and wherein said lock is configured to prevent said actuator from moving into either of said first drive slot and said second drive slot when said lock is engaged with said actuator.

23. A surgical stapler, comprising:
a first handle portion including a staple cartridge attachment portion configured to have a staple cartridge attached thereto;
a second handle portion comprising an anvil;
a drive member configured to be moved between a first position and a second position;
a lock configurable in a locked condition and an unlocked condition, wherein said lock is configured to hold said drive member in said first position when said lock is in said locked condition; and
a latch rotatably coupled to one of said first handle portion and said second handle portion, wherein said latch is movable through a first range of closing motion and a second range of closing motion, wherein said latch is configured to engage the other of said first handle portion and said second handle portion and move said anvil and said staple cartridge attachment portion into position relative to one another when said latch is moved through said first range of closing motion, and wherein said latch is configured to place said lock in said unlocked condition when said latch is moved through said second range of closing motion.

24. The surgical stapler of claim 23, further comprising said staple cartridge.

25. The surgical stapler of claim 23, wherein said latch further comprises a cam configured to engage said lock and move said lock away from said drive member into said unlocked condition.

26. The surgical stapler of claim 23, wherein said drive member further comprises an actuator, wherein said actuator is movable toward said staple cartridge attachment portion to move said drive member between said first position and said second position, and wherein said lock is configured to engage said actuator when said lock is in said locked condition.

27. The surgical stapler of claim 26, further comprising a first drive slot and a second drive slot, wherein said actuator is selectively movable into said first drive slot and said second drive slot in order to move said drive member into said second position, and wherein said lock is configured to prevent said actuator from moving into either of said first drive slot and said second drive slot when said lock is engaged with said actuator.

28. A surgical stapler, comprising:
a first handle portion including a staple cartridge attachment portion configured to have a staple cartridge attached thereto;
a second handle portion comprising an anvil support portion configured to support an anvil;
a drive member configured to be moved toward said staple cartridge attachment portion;
a lock movably engageable with said drive member; and
a latch rotatably coupled to one of said first handle portion and said second handle portion, wherein said latch is movable through a closing motion into a fully-closed position, wherein said latch is configured to engage the other of said first handle portion and said second handle portion and move said anvil support portion and said staple cartridge attachment portion into position relative to one another when said latch is moved through said closing motion, and wherein said latch is configured to operably disengage said lock from said drive member when said latch is moved into said fully-closed position.

29. The surgical stapler of claim 28, further comprising said anvil.

30. The surgical stapler of claim 29, further comprising said staple cartridge.

31. The surgical stapler of claim 28, wherein said latch further comprises a cam configured to engage said lock and move said lock away from said drive member.

32. The surgical stapler of claim 28, wherein said drive member further comprises an actuator, wherein said actuator is movable toward said staple cartridge attachment portion to move said drive member toward said staple cartridge attachment portion, and wherein said lock is configured to engage said actuator.

33. The surgical stapler of claim 32, further comprising a first drive slot and a second drive slot, wherein said actuator is selectively movable into said first drive slot and said second drive slot in order to move said drive member toward said staple cartridge attachment portion, and wherein said lock is configured to prevent said actuator from moving into either of said first drive slot and said second drive slot when said lock is engaged with said actuator.

34. A surgical stapler, comprising:
a first handle portion including a staple cartridge attachment portion configured to have a staple cartridge attached thereto;
a second handle portion comprising an anvil;
a drive member configured to be moved between an unfired position and a fired position;
a lock configurable in a locked condition and an unlocked condition, wherein said lock is configured to hold said drive member in said unfired position when said lock is in said locked condition; and
a latch rotatably coupled to one of said first handle portion and said second handle portion, wherein said latch is movable through a closing motion into a closed position, wherein said latch is configured to engage the other of said first handle portion and said second handle portion and move said anvil relative to said staple cartridge attachment portion during said closing motion, and wherein said latch is configured to place said lock in said unlocked condition when said latch is moved into said closed position.

35. The surgical stapler of claim 34, further comprising said staple cartridge.

36. The surgical stapler of claim 34, wherein said latch further comprises a cam configured to engage said lock and move said lock away from said drive member into said unlocked condition.

37. The surgical stapler of claim 34, wherein said drive member further comprises an actuator, wherein said actuator is movable toward said staple cartridge attachment portion to move said drive member between said unfired position and said fired position, and wherein said lock is configured to engage said actuator when said lock is in said locked condition.

38. The surgical stapler of claim 37, further comprising a first drive slot and a second drive slot, wherein said actuator is selectively movable into said first drive slot and said second drive slot in order to move said drive member into said fired position, and wherein said lock is configured to prevent said actuator from moving into either of said first drive slot and said second drive slot when said lock is engaged with said actuator.

39. A surgical stapler, comprising:
a first handle portion including a staple cartridge attachment portion configured to have a staple cartridge attached thereto;
a second handle portion comprising an anvil support portion configured to support an anvil;
a drive member;
an actuator configured to move said drive member between an unfired position and a fired position;
an actuator lock movable between a locked condition in which said actuator lock is operably engaged with said actuator and an unlocked condition in which said actuator lock is operably disengaged from said actuator, wherein said actuator lock is configured to hold said drive member in said unfired position when said actuator lock is in said locked condition; and
a latch rotatably coupled to one of said first handle portion and said second handle portion, wherein said latch is movable through a closing motion into a closed position, wherein said latch is configured to engage the other of said first handle portion and said second handle portion and move said anvil support portion relative to said staple cartridge attachment portion during said closing motion, and wherein said latch is configured to place said actuator lock in said unlocked condition when said latch is moved into said closed position.

40. The surgical stapler of claim 39, further comprising said anvil.

41. The surgical stapler of claim 40, further comprising said staple cartridge.

42. The surgical stapler of claim 39, further comprising a first drive slot and a second drive slot, wherein said actuator is selectively movable into said first drive slot and said second drive slot in order to move said drive member into said fired position, and wherein said actuator lock is configured to prevent said actuator from moving into either of said first drive slot and said second drive slot when said actuator lock is engaged with said actuator.

43. The surgical stapler of claim 39, wherein said latch further comprises a cam configured to engage said lock and move said lock away from said drive member into said unlocked condition.

* * * * *